United States Patent
Yajima et al.

(10) Patent No.: US 9,870,726 B2
(45) Date of Patent: Jan. 16, 2018

(54) IMAGE DISPLAY APPARATUS, IMAGE DISPLAY METHOD, STORAGE MEDIUM, AND MONITORING SYSTEM

(71) Applicant: SONY CORPORATION, Tokyo (JP)

(72) Inventors: Masakazu Yajima, Chiba (JP); Yoichiro Sako, Tokyo (JP); Takayuki Hirabayashi, Tokyo (JP); Kouichirou Ono, Tokyo (JP); Masashi Takeda, Tokyo (JP); Akira Ono, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 54 days.

(21) Appl. No.: 14/767,822

(22) PCT Filed: Jan. 6, 2014

(86) PCT No.: PCT/JP2014/050004
§ 371 (c)(1),
(2) Date: Aug. 13, 2015

(87) PCT Pub. No.: WO2014/129212
PCT Pub. Date: Aug. 28, 2014

(65) Prior Publication Data
US 2016/0049108 A1    Feb. 18, 2016

(30) Foreign Application Priority Data

Feb. 22, 2013 (JP) .................. 2013-033759
May 27, 2013 (JP) .................. 2013-110582

(51) Int. Cl.
*G09G 5/00* (2006.01)
*G09G 3/20* (2006.01)
(Continued)

(52) U.S. Cl.
CPC .............. *G09G 3/20* (2013.01); *A61B 5/1118* (2013.01); *A61B 5/6807* (2013.01); *A61B 5/744* (2013.01);
(Continued)

(58) Field of Classification Search
CPC . G06F 1/163; G06F 1/28; G06F 3/011; G09G 3/20; A61B 5/1118; A61B 5/6807; A61B 5/744; A63F 13/00; H04N 5/7491
See application file for complete search history.

(56) References Cited

U.S. PATENT DOCUMENTS

| 5,494,468 A * | 2/1996 | Demarco, Jr. ......... A63B 31/11 441/64 |
| 5,815,126 A * | 9/1998 | Fan ...................... G02B 27/017 345/7 |
| 2011/0037349 A1* | 2/2011 | Sham ................... A43B 3/0015 310/339 |

FOREIGN PATENT DOCUMENTS

| JP | 7-11125 U | 2/1995 |
| JP | 07-281733 A | 10/1995 |

(Continued)

*Primary Examiner* — Towfiq Elahi
(74) *Attorney, Agent, or Firm* — Chip Law Group

(57) ABSTRACT

A head-mounted display, a smart phone, a tablet terminal, an electronic book, or the like monitors conditions of the side of a power generation apparatus that charges a battery.

An image display apparatus includes a power generation information acquisition means for obtaining power generation information on a power storage amount, a power generation amount, and the like of a secondary battery in each power generation apparatus, appropriately processes the obtained information, and displays it to a user via a display unit. The user can check the power generation amount of the power generation apparatus and the power storage amount of the secondary battery without stopping the use of the image display apparatus. When a power
(Continued)

storage amount of a battery in use is lowered, the user can properly judge with which of the power generation apparatuses the user should replace the battery.

13 Claims, 52 Drawing Sheets

(51) Int. Cl.
    *A63F 13/00* (2014.01)
    *G06F 1/28* (2006.01)
    *H04N 5/74* (2006.01)
    *A61B 5/11* (2006.01)
    *G06F 1/16* (2006.01)
    *G06F 3/01* (2006.01)
    *H02N 2/18* (2006.01)
    *G02B 27/01* (2006.01)
    *A61B 5/00* (2006.01)
    *G01M 9/00* (2006.01)
    *A61B 5/103* (2006.01)

(52) U.S. Cl.
    CPC .............. *A63F 13/00* (2013.01); *G06F 1/163* (2013.01); *G06F 1/28* (2013.01); *G06F 3/011* (2013.01); *H02N 2/18* (2013.01); *H04N 5/7491* (2013.01); *A61B 5/1038* (2013.01); *A61B 5/112* (2013.01); *A61B 5/4023* (2013.01); *A61B 5/4866* (2013.01); *A61B 2503/40* (2013.01); *G01M 9/00* (2013.01); *G02B 27/0176* (2013.01); *G09G 2330/02* (2013.01)

(56) References Cited

FOREIGN PATENT DOCUMENTS

| | | |
|---|---|---|
| JP | 2001-204293 A | 7/2001 |
| JP | 2001-215920 A | 8/2001 |
| JP | 2003-337551 A | 11/2003 |
| JP | 2005-046305 A | 2/2005 |
| JP | 2006-081402 A | 3/2006 |
| JP | 2007-330034 A | 12/2007 |
| JP | 2008-292980 A | 12/2008 |
| JP | 2008-301606 A | 12/2008 |
| JP | 2008-304268 A | 12/2008 |
| JP | 2010-015886 A | 1/2010 |
| JP | 2010-016321 A | 1/2010 |
| JP | 2010-032305 A | 2/2010 |
| JP | 2011-002753 A | 1/2011 |

* cited by examiner

Monitoring system 3600

IMAGE DISPLAY APPARATUS, IMAGE DISPLAY METHOD, STORAGE MEDIUM, AND MONITORING SYSTEM

TECHNICAL FIELD

The technology disclosed in this specification relates to an image display apparatus that is driven mainly by a battery, for example, a head-mounted display, a cellular phone such as a smart phone, a tablet terminal, an electronic book, and a portable music player, to an image display method, to a storage medium, and to a monitoring system that monitors conditions of the side of a power generation apparatus that charges a battery that can be used in the image display apparatus.

BACKGROUND ART

Compact information devices that can be carried and used by a user outside the home, for example, a cellular phone such as a smart phone, a tablet terminal, an electronic book, and a portable music player have been widely used. In recent years, information devices used by being mounted on a part of the body, for example, the head or arm of the user have been increased. For example, head-mounted displays and wristband type devices have been used. The head-mounted display is used by being mounted on the head or face of the user. An image display unit is disposed facing each of the left and right eyes (or a single eye). An enlarged virtual image of a displayed image is formed by a virtual image optical system. In this manner, it is possible to present an image with realistic sensation. It is also possible to present AR (Augmented Reality) information superimposed on a field of view of the user.

A compact information device of this type is basically configured to be driven by a storage element such as a secondary battery as a main power source, considering the use in an environment without a power supply outside the home. Moreover, the secondary battery has a limited operational time. Therefore, for charging it anywhere, many users carry a portable charger. In addition, in recent years, development of portable power generation apparatuses that obtain electrical power by power generation using environmental energy or the like anywhere has been progressed. Examples of an energy source in energy harvesting can include environmental electromagnetic waves, sunlight, vibrations, and heat.

If it is an information device used by being mounted on a part of a body of the user, by incorporating the power generation apparatus in the device, power generation can be automatically performed by the user, using human ordinary actions such as walking. For example, a power generation apparatus installed in a shoe worn by a user (e.g., see Patent Documents 1 and 2) uses the weight of the user as external weight, and hence can generate electrical power by walking or running in an ordinary life. Thus, a practical power generation apparatus can be provided. Using the obtained electrical power, the power generation apparatus of this type can drive a portable device or charge a secondary battery.

The user of the power generation apparatus has to check whether or not the secondary battery has a sufficient power storage amount. If the power storage amount is sufficient, the user can detach the storage battery from the power generation apparatus and replace a secondary battery in an information device used by the user with the storage battery or carry the storage battery as a spare battery.

By the way, if the user checks the power storage amount of the secondary battery and the power storage amount is insufficient, the action of checking and replacing the battery becomes in vain. If the information device incorporates the power generation apparatus, the information device can display a charging condition of the battery on a display and inform the user of this. In contrast, if the power generation apparatus is installed outside the information device (e.g., in shoes worn by the user), the information device does not include means for obtaining information on the power storage amount of the secondary battery in the power generation apparatus. Thus, the user should stop the use of the information device and check the power storage amount by viewing the power generation apparatus, which is cumbersome. If the information device is a type worn by the user, for example, a head-mounted display, it can be reasonable to place the power generation apparatus outside instead of incorporating the power generation apparatus in the information device in view of a weight burden on the user.

If the power generation apparatus is installed in each of the left and right shoes worn by the user or if a plurality of power generation apparatuses using energy harvesting or the like are dispersedly arranged in a surrounding environment of the user, checking the power storage amount of each of the power generation apparatuses and judge which of the secondary batteries of the power generation apparatuses should be used is troublesome for the user.

SUMMARY OF INVENTION

Problem to be Solved by the Invention

It is an object of the technology disclosed in this specification to provide an excellent image display apparatus that is driven mainly by a battery, for example, a head-mounted display, a cellular phone such as a smart phone, a tablet terminal, an electronic book, and a portable music player and can favorably monitor conditions of the side of a power generation apparatus that charges the battery, an image display method, a storage medium, and a monitoring system.

Means for Solving the Problem

The present application has been made in view of the problems described above. According to the technology of claim 1, there is provided an image display apparatus including:

an image display unit that displays an image;

a communication unit that communicates with a power generation apparatus; and a control unit that obtains first information on power generation from the power generation apparatus via the communication unit, converts the first information into second information based on a principle of the power generation apparatus for inducing electrical power, and controls the image display unit.

According to the technology of claim 2 of the present application, the image display unit of the image display apparatus according to claim 1 is configured to be mounted on a head or face.

According to the technology of claim 3 of the present application, the control unit of the image display apparatus according to claim 1 is configured to control the image display unit to combine a virtual image expressing at least either the first information or the second information with a real image showing the power generation apparatus and display the combined image.

According to the technology of claim 4 of the present application, the control unit of the image display apparatus according to claim 1 is configured to convert a power generation amount of the power generation apparatus included in the first information into the second information including a physical quantity used by the power generation apparatus for inducing electrical power.

According to the technology of claim 5 of the present application, the control unit of the image display apparatus according to claim 1 is configured to derive, based on at least either the first information or the second information, third information including control information for controlling the image display apparatus itself or an external device.

According to the technology of claim 6 of the present application, the control unit of the image display apparatus according to claim 1 is configured to derive, based on at least either the first information or the second information, third information including action-inducing information for inducing a user to take a predetermined action.

According to the technology of claim 7 of the present application, the power generation apparatus is installed in a shoe worn on at least either one of left and right feet of a human body and configured to generate electrical power according to an amount of exercise of the foot. The control unit of the image display apparatus according to claim 1 is configured to convert a power generation amount of the power generation apparatus into the amount of exercise of the foot as the second information.

According to the technology of claim 8 of the present application, the power generation apparatus is adapted to generate electrical power to a shoe worn on each of left and right feet of a human body according to an amount of exercise of each of the feet. The control unit of the image display apparatus according to claim 1 is configured to display, on a left-hand side of a screen, information on the amount of exercise of the left foot that is converted from a power generation amount of the power generation apparatus for the shoe of the left foot and display, on a left-hand side of the screen, information on the amount of exercise of the right foot that is converted from a power generation amount of the power generation apparatus for the shoe of the right foot.

According to the technology of claim 9 of the present application, the power generation apparatus is adapted to generate electrical power to a shoe worn on each of left and right feet of a human body according to an amount of exercise of each of the feet. The control unit of the image display apparatus according to claim 1 is configured to estimate a posture of the human body based on a difference between power generation amounts of the left and right power generation apparatuses or an acceleration of each of the feet that is obtained by converting each of the power generation amounts of the left and right power generation apparatuses as the second information, derive action-inducing information for inducing an action to correct a deviation of the posture of the human body as third information, and cause the image display unit to display the third information.

According to the technology of claim 10 of the present application, the control unit of the image display apparatus according to claim 1 is configured to convert a power generation amount of a first power generation apparatus attached to a collar of a companion animal, which serves as the first information, into an acceleration or a metabolic rate of the companion animal, which serves as the second information and convert a power generation amount of a second power generation apparatus attached to a lead with which a person pulls the companion animal, which serves as the first information, into an acceleration or a metabolic rate of the person, which serves as the second information, and cause the image display unit to display the second information.

According to the technology of claim 11 of the present application, the control unit of the image display apparatus according to claim 1 is configured to convert a power generation amount of each of the power generation apparatuses that are installed in a plurality of locations and generate electrical power using electromagnetic waves, radioactivity, or other environmental energy, which serves as the first information, into environmental-energy intensity in each of the locations, which serves as the second information, and cause the image display unit to display the environmental-energy intensity obtained from each of the power generation apparatuses in association with the corresponding location.

According to the technology of claim 12 of the present application, the power generation apparatus is installed in a foot fin mounted on at least one of left and right feet of a person who is diving and adapted to generate electrical power according to the number of kicks of the foot. The control unit of the image display apparatus according to claim 1 is configured to convert a power generation amount of the power generation apparatus into an amount of exercise of the foot, an acceleration, or a water flow, which serves as the second information, and cause the image display unit to display the second information.

According to the technology of claim 13 of the present application, the control unit of the image display apparatus according to claim 1 is configured to convert a power generation amount of each of the power generation apparatuses that are installed in a plurality of locations within a farm and generate electrical power according to sunlight intensity, which serves as the first information, into an amount of solar radiation in each of the locations, which serves as the second information, derive a growth level, a harvest period, or a harvest order of a farm product in each of the locations from the amount of solar radiation as third information, and cause the image display unit to display the second information or the third information in association with the corresponding location.

According to the technology of claim 14 of the present application, the control unit of the image display apparatus according to claim 1 is configured to convert a power generation amount of each of the power generation apparatuses that are installed in a plurality of locations in a manufacturing line within a factory and generate electrical power according to at least one of a temperature difference, mechanical vibrations, or radio waves, which serves as the first information, into a temperature, a vibration amount, or radio-wave intensity in each of the locations, which serves as the second information, derive, from the second information, a dangerous point in the manufacturing line as third information, and cause the image display unit to display the second information or the third information in association with the corresponding location.

According to the technology of claim 15 of the present application, the control unit of the image display apparatus according to claim 1 is configured to convert a power generation amount of each of the power generation apparatuses that are installed in a moving object present in a location difficult for the user to see and generate electrical power according to at least either sunlight or mechanical vibrations, which serves as the first information, into sunlight intensity or a vibration amount in each of the locations, which serves as the second information, and cause the image display unit to display the second information in association with the corresponding location.

According to the technology of claim 16 of the present application, the power generation apparatus is installed on a body of any of a player who is playing a competition, a judge, and a spectator, and adapted to generate electrical power using a physical quantity generated in the body. The control unit of the image display apparatus according to claim 1 is configured to derive a state of the player, the competition, or a playing field from a physical quantity obtained by converting a power generation amount of the power generation apparatus.

According to the technology of claim 17 of the present application, the control unit of the image display apparatus according to claim 1 is configured to derive, based on at least either the first information or the second information, third information including an image that is added to an image displayed on the image display unit.

According to the technology of claim 18 of the present application, there is provided an image display method including the steps of:

communicating with a power generation apparatus and obtaining first information on power generation in the power generation apparatus;

converting the first information into second information based on a principle of the power generation apparatus for inducing electrical power; and displaying the first image or second image.

According to the technology of claim 19 of the present application, there is provided a storage medium that stores a computer program described in a computer readable format to cause a computer to function as:

an image display unit that displays an image;

a communication unit that communicates with a power generation apparatus; and a control unit that obtains first information on power generation from the power generation apparatus via the communication unit, converts the first information into second information based on a principle of the power generation apparatus for inducing electrical power, and controls the image display unit.

The storage medium according to claim 19 of this application defines a storage medium that stores a computer program described in a computer in a computer readable format to realize predetermined processing in a computer. In other words, by installing the computer program stored in the storage medium according to claim 19 of this application into the computer, a cooperative action is exerted on the computer and the same actions and effects as those of the image display apparatus according to claim 1 of this application can be obtained.

According to the technology of claim 20 of the present application, there is provided a monitoring system including: a power generation apparatus that generates electrical power using a physical quantity generated in a location where the power generation apparatus is installed and transmits first information on power generation; and an image display apparatus that receives the first information, converts the first information into second information including the physical quantity, and displays an image for monitoring the location where the power generation apparatus is installed, using the physical quantity.

It should be noted that the "system" used herein refers to the aggregate of a plurality of apparatuses (or functional modules to achieve specific functions) logically collected, and whether the apparatuses or functional modules exist in a single casing or not is not taken into consideration.

Effect of the Invention

According to the technology disclosed herein, it is possible to provide an excellent image display apparatus that is driven mainly by a battery, for example, a head-mounted display, a cellular phone such as a smart phone, a tablet terminal, an electronic book, and a portable music player and can favorably monitor conditions of the side of a power generation apparatus that charges the battery, an image display method, a storage medium, and a monitoring system.

According to the technology disclosed herein, the image display apparatus includes means for obtaining information on a power storage amount, a power generation amount, and the like of a secondary battery in one or more power generation apparatuses provided outside this apparatus. Thus, the user of the image display apparatus can check the power storage amount of the secondary battery in the power generation apparatus without stopping the use of the image display apparatus. For example, when a power storage amount of a battery in use is lowered, the user can properly judge with which of the power generation apparatuses the user should replace the battery.

According to the technology disclosed herein, the image display apparatus displays the image in combination with various types of information generated or converted from the power generation amounts of the power generation apparatuses, and hence the user can know at a glance various types of information in the real world. For example, the image display apparatus can convert, based on the principle of the power generation unit for inducing electrical power, a power generation amount that is the first information obtained from the power generation apparatus into the second information for monitoring, such as user-monitoring information such as an amount of exercise of the user and environment-monitoring information such as ultraviolet intensity and radio-wave intensity, and presents it to the user. In addition, the image display apparatus can generate, based on the second information obtained by converting the first information (or the first information itself), the third information such as action-inducing information for inducing the user to take an action and control information for controlling the image display apparatus itself or other devices.

Still another objects, features, and advantages of the technology disclosed herein will be clearly described in more detail based on embodiments to be described later and attached drawings.

MODE(S) FOR CARRYING OUT THE INVENTION

Hereinafter, embodiments of the technology disclosed in this specification will be described in detail with reference to the drawings.

A. Configuration of Apparatus

Figure 1:
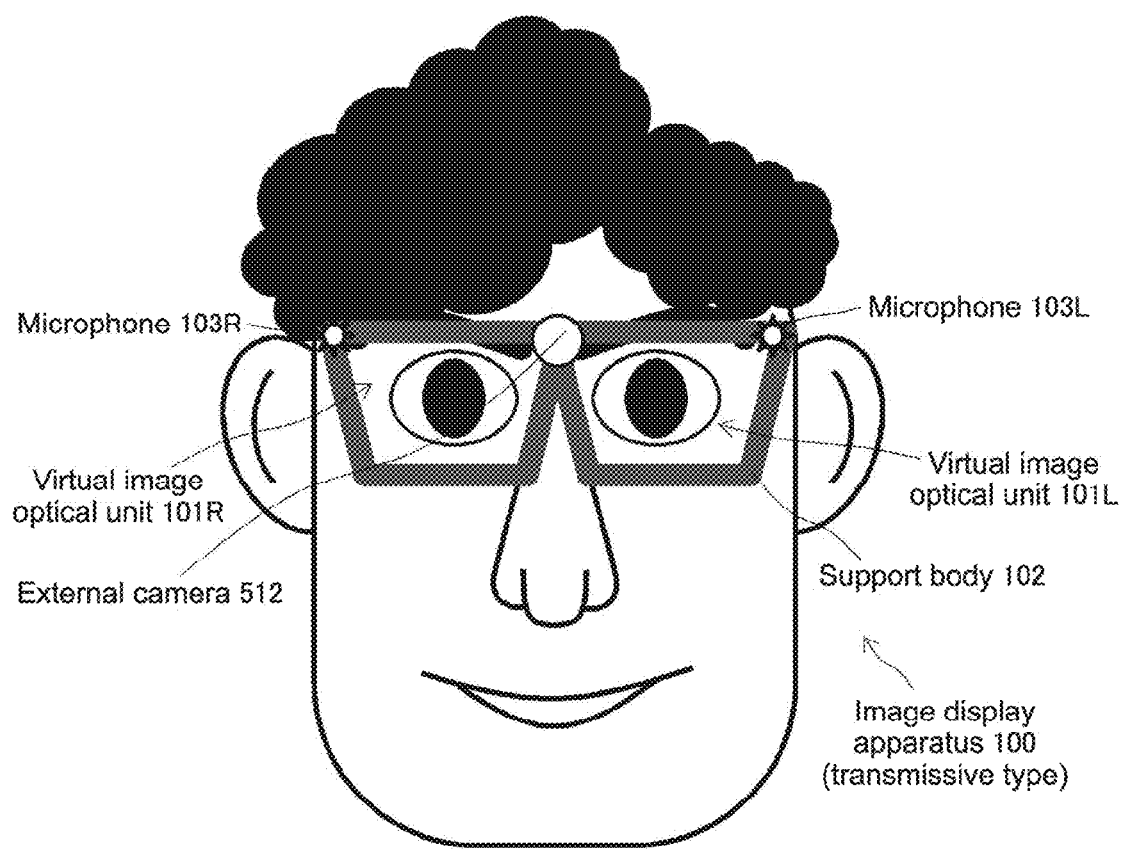
FIG. 1 is a diagram showing a user wearing a transmissive type head-mounted image display apparatus 100 as viewed from the front.

FIG. 1 shows an outer appearance configuration of an image display apparatus 100 according to an embodiment of the technology disclosed herein. The image display apparatus 100 is used by being mounted on the head or face of a user, and displays images for left and right eyes. The image display apparatus 100 shown in the figure is a transmissive type, i.e., a see-through type, with which the user can view (i.e., see through) a landscape in the real world through an image during display of images. Thus, it is possible to superimpose a virtual displayed image such as an AR image on the landscape in the real world (see, for example, Patent Document 3). Since the displayed image is not seen from the outside (i.e., by anyone else), it is easy to protect the privacy of the user when information is displayed.

The image display apparatus 100 shown in the figure has a structure similar to eye correction glasses. At positions of the main body of the image display apparatus 100, which are opposed to the left and right eyes of the user, virtual image optical units 101L and 101R formed of transparent light guide units or the like are disposed, respectively. Images (not shown) observed by the user are displayed on the inside of the virtual image optical units 101L and 101R. Each of the virtual image optical units 101L and 101R is supported by, for example, an eyeglass-frame-shaped support body 102.

At substantially the center of the eyeglass-frame-shaped support body 102, an external camera 512 for inputting images of surroundings (a field of view of the user) is provided. The external camera 512 can capture an image of a landscape in a user's line-of-sight direction, for example. For example, if the external camera 512 is formed of a plurality of cameras, the three-dimensional information on the images of surroundings can be obtained using parallax information. Additionally, even one camera can perform imaging while being moved using a SLAM (Simultaneous Localization and Mapping) image recognition, and calculate parallax information using a plurality of frame images temporally anterior and posterior (see, for example, Patent Document 5), to obtain three-dimensional information on the images of surroundings based on the calculated parallax information.

Additionally, in the vicinity of both left and right ends of the support body 102, microphones 103L and 103R are provided, respectively. With the microphones 103L and 103R being provided substantially symmetrically, only sounds (voice of the user) localized at the center are recognized, and can thus be separated from noise of surroundings and voices of other people. For example, this allows prevention of malfunctions when an operation by voice input is made.

Figure 2:
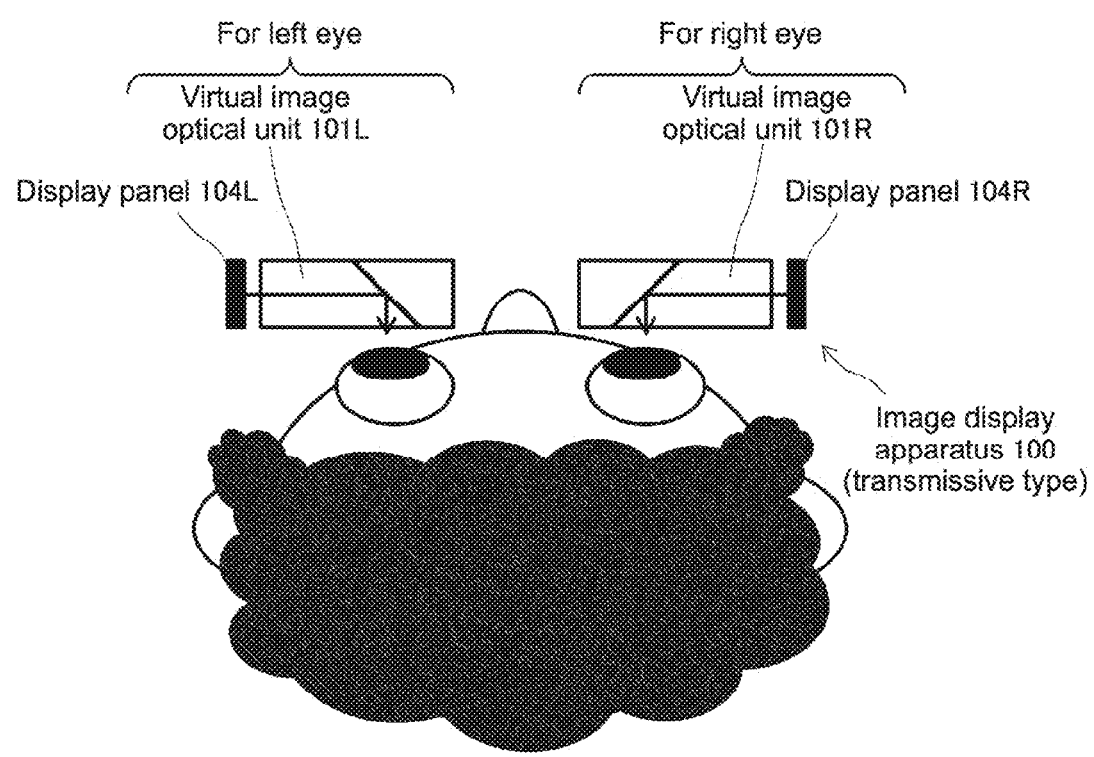
FIG. 2 is a diagram showing the user wearing the image display apparatus 100 shown in FIG. 1 as viewed from above.

FIG. 2 shows the image display apparatus 100 worn by the user as viewed from above. As shown in the figure, at both left and right ends of the image display apparatus 100, display panels 104L and 104R to display and output right-eye and left-eye images, respectively, are disposed. Each of the display panels 104L and 104R is formed of a microdisplay such as a liquid-crystal display and an organic EL device, a laser scanning display such as a retinal direct-drawing display, or the like. The left and right displayed images output from the display panels 104L and 104R are guided by the virtual image optical units 101L and 101R to the vicinity of the respective left and right eyes, and then enlarged virtual images thereof are formed on the pupils of the user.

Figure 3:
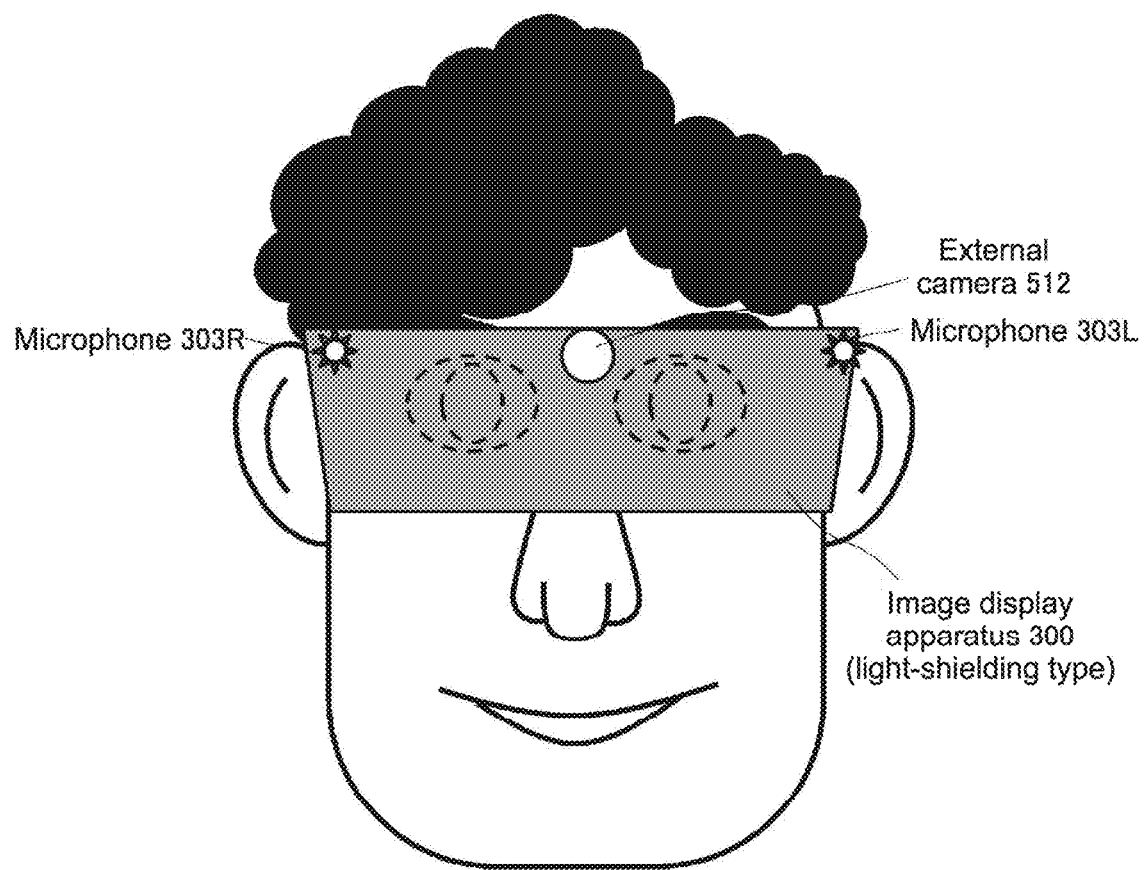
FIG. 3 is a diagram showing the user wearing a light-shielding type head-mounted image display apparatus 300 as viewed from the front.

FIG. 3 shows an outer appearance configuration of an image display apparatus 300 according to another embodiment of the technology disclosed herein. The image display apparatus 300 is used by being mounted on the head or face of the user. At positions inside of a main body thereof, which are opposed to the left and right eyes, there are provided display panels (not shown in FIG. 3) to be observed by the user. Each of the display panels is formed of a microdisplay such as a liquid-crystal display and an organic EL device or a laser scanning display such as a retinal direct-drawing display. The image display apparatus 300 has light-shielding property and can directly cover the eyes of the user when being mounted on the head, to give a sense of immersion to the user who is viewing images.

Unlike a see-through type, a user wearing the image display apparatus 300 cannot directly view a landscape in the real world. When an external camera 512 to capture an image of a landscape in a user's line-of-sight direction is provided and a captured image is displayed, the user can indirectly view (i.e., video see through) the landscape in the real world. As a matter of course, a virtual displayed image can be superimposed on a video see-through image. Since the displayed image is not seen from the outside (i.e., by anyone else), it is easy to protect the privacy of the user when information is displayed.

At substantially the center of the front of the main body of the image display apparatus 300, an external camera 512 for inputting images of surroundings (a field of view of the user) is provided. Additionally, in the vicinity of both left and right ends of the main body of the image display apparatus 300, microphones 303L and 303R are provided, respectively. With the microphones 303L and 303R being provided substantially symmetrically, only sounds (voice of the user) localized at the center are recognized, and can thus be separated from noise of surroundings and voices of other people. For example, this allows prevention of malfunctions when an operation by voice input is performed on the image display apparatus 300.

Figure 4:
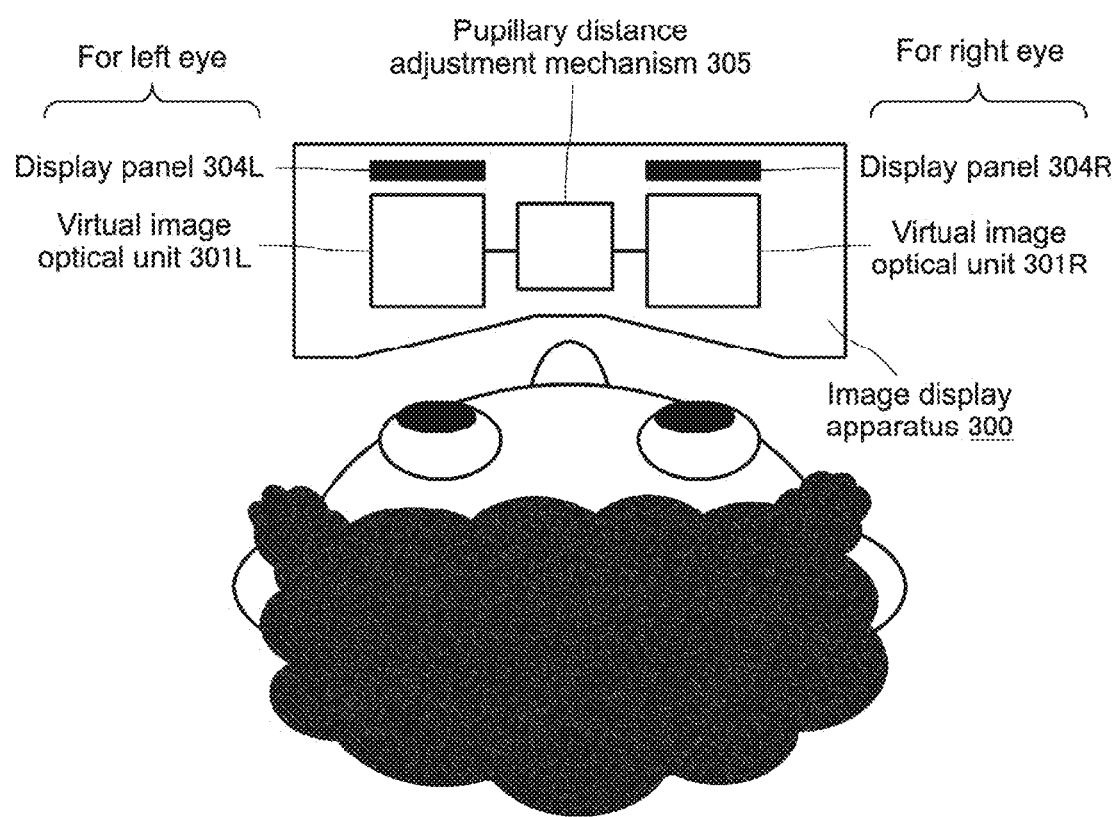
FIG. 4 is a diagram showing the user wearing the image display apparatus 300 shown in FIG. 3 as viewed from above.

FIG. 4 shows the user wearing the image display apparatus 300 shown in FIG. 3 as viewed from above. The image display apparatus 300 shown in the figure is formed of display panels 304L and 304R for the left and right eyes, respectively, on the side surface opposed to the face of the user. Each of the display panels 304L and 304R is formed of a microdisplay such as a liquid-crystal display and an organic EL device or a laser scanning display such as a retinal direct-drawing display. The displayed images of the display panels 304L and 304R pass through virtual image optical units 301L and 301R, respectively, to be observed by the user as enlarged virtual images. Further, since the height of eyes and a pupillary distance thereof are individually different between users, the left and right display systems and the eyes of the user wearing the image display apparatus 300 are required to be aligned. In the example shown in FIG. 4, a pupillary distance adjustment mechanism 305 is provided between the right-eye display panel and the left-eye display panel.

Figure 5:
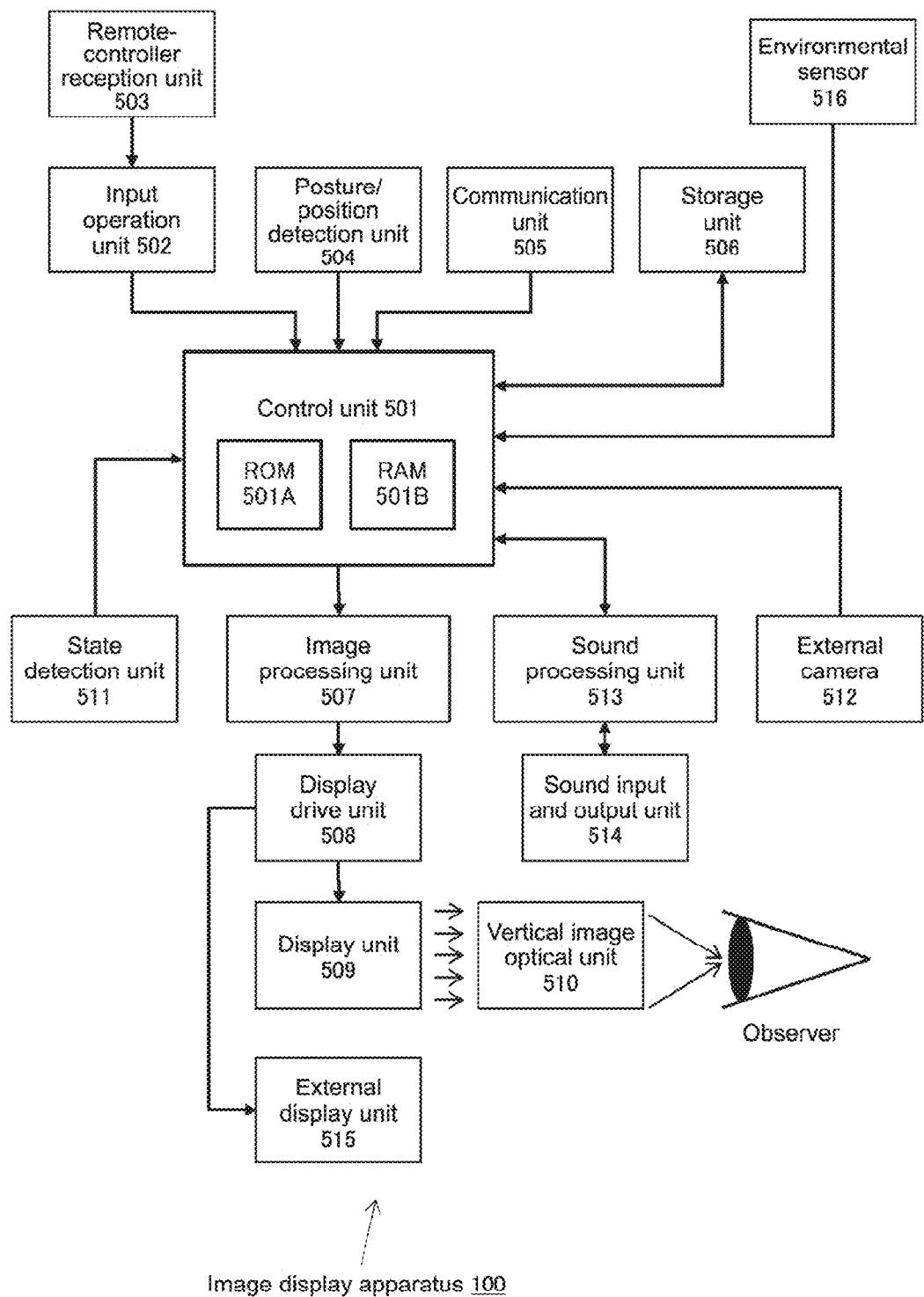
FIG. 5 is a diagram showing an internal configuration example of the image display apparatus 100.

FIG. 5 shows an internal configuration example of the image display apparatus 100. It should be understood that the other image display apparatus 300 also has a similar internal configuration. Hereinafter, the units will be described.

A control unit 501 includes a ROM (Read Only Memory) 501A and a RAM (Random Access Memory) 501B. The ROM 501A stores program codes and various types of data that are executed in the control unit 501. The control unit 501 executes a program loaded to the RAM 501B, to start display control of images and collectively control the whole operation of the image display apparatus 100. Examples of the program and data stored in the ROM 501A can include an image display control program, an image processing program for an image captured by the external camera 512, a program for processing for communication with an external device such as a server on the Internet (not shown), a power generation information-processing program for processing first information such as power generation amount and power storage amount obtained from a power generation apparatus (described later) installed outside the image display apparatus 100, a monitoring processing program for displaying monitoring information detected by various sensors (described later) mounted on the apparatus 100 and monitoring information that is converted from the power generation amount of the power generation apparatus or the like on a display unit 509 and an external display unit 515 (described later), a game program in which a CG (Computer Graphics) character such as an avatar appears, and identification information unique to the apparatus 100.

As will be described later, based on a principle of the power generation unit for inducing electrical power, the power generation information-processing program converts the power generation amount that is the first information obtained from the power generation apparatus into second information such as a physical quantity used for power generation, for example, an amount of exercise of the user, ultraviolet intensity, or radio-wave intensity. The physical quantity resulting from the conversion can be used as user-monitoring information for monitoring a motion or state of the user wearing the power generation apparatus or environment-monitoring information for monitoring an environment in a location where the power generation apparatus is installed. According to the power generation information-processing program, even if the power generation apparatus does not include sensors, the image display apparatus can obtain, based on the power generation amount or the like, the monitoring information equivalent to detection results of the sensors. According to the monitoring processing program, the second information calculated according to the power generation information-processing program is displayed as the user-monitoring information or the environment-monitoring information. It enables the user to perform monitoring.

In addition, according to the power generation information-processing program, based on the second information obtained by converting the first information (or the first information itself), action-inducing information for inducing the user to take an action for increasing the power generation amount or increasing or reducing the physical quantity used for power generation, control information for controlling the image display apparatus 100 itself or other devices, and the like are derived as third information. According to the monitoring processing program, the display of the action-inducing information is also performed. As will be described later, if the user takes an action according to the action-inducing information, the exercise capacity is improved. For example, the gravity balance in the left- and right-hand directions is corrected. Otherwise, if the user takes an action according to the action-inducing information, good influences of the environment on the user can be increased or adverse influences of the environment on the user can be reduced.

An input operation unit 502 includes at least one operation element such as a key, a button, and a switch, with which the user performs an input operation. The input operation unit 502 receives a user's instruction made via the operation element and outputs the instruction to the control unit 501. The input operation unit 502 similarly receives a user's instruction, which is a remote-controller command received by a remote-controller reception unit 503, and outputs the instruction to the control unit 501.

A posture/position detection unit 504 is a unit that detects a posture or position of the head of the user wearing the image processing apparatus 100. The posture/position detection unit 504 is formed of any one of a gyroscope, an acceleration sensor, a GPS (Global Positioning System) sensor, a geomagnetic sensor, a Doppler sensor, an infrared sensor, radio-wave intensity sensor, and the like, or a combination of two or more those sensors in consideration of their advantages and disadvantages.

A state detection unit 511 obtains state information on a state of the user wearing the image display apparatus 100 and outputs the state information to the control unit 501. As the state information, for example, the state detection unit 511 obtains an operating state of the user (whether the user wears the image display apparatus 100 or not), a behavioral state of the user (states of movement such as rest, walking, and running, an open or closed state of eyelids, line-of-sight direction, and dilation/contraction of pupils), a mental state (the degree of impression, excitation, or wakefulness, feelings, emotions, etc. on whether the user is immersed or concentrated in observation of displayed image), and a physiological state. Additionally, the state detection unit 511 may include, in order to obtain those pieces of state information from the user, various state sensors (not shown) such as a mounted sensor formed of a mechanical switch and the like, an internal camera to capture an image of the face of the user, a gyroscope, an acceleration sensor, a velocity sensor, a pressure sensor, a body temperature sensor, a perspiration sensor, an electromyogram sensor, an electrooculography sensor, a brain wave sensor, an exhalation sensor, a gas sensor, and an ion concentration sensor.

An environmental sensor 516 is formed of various sensors that measure information on the environment of the image display apparatus 100. The environmental sensor 516 includes, for example, an acceleration sensor, an electromagnetic wave sensor, a geomagnetic sensor, a water flow sensor, an airflow sensor, an optical sensor, a temperature sensor, and an illuminance sensor, which will be described later.

The external camera 512 is located at substantially the center of the front of the main body of the eyeglass-shaped image display apparatus 100, for example (see FIG. 1), and can capture images of surroundings. Additionally, the posture of the external camera 512 in pan, tilt, and roll directions can be controlled in accordance with the user's line-of-sight direction detected by the state detection unit 511, and thus an image in a user's own line of sight, that is, an image in the user's line-of-sight direction can be captured with use of the external camera 512. The external camera 512 more favorably includes a plurality of cameras such that the three-dimensional information on the images of surroundings can be obtained using parallax information. It is assumed that the user can adjust zooming of the external camera 512 via an operation of the input operation unit 502, dilation/contraction of the pupils that is recognized based on a captured image of an internal camera or the like, or an instruction voice input. The captured image of the external camera 512 can be output to a display unit 509 for display, and can also be stored in a storage unit 506.

A communication unit 505 performs processing for communication with an external device such as a server on the Internet (not shown) and the power generation apparatus (described later) and also performs modulation/demodulation and coding/decoding processing for communication signals. Additionally, the control unit 501 transmits data from the communication unit 505, the data being transmitted to an external device.

For example, the communication unit 505 receives, from the external device (not shown), an image signal to be output to the display unit 509 (described later) for display. Examples of the "external device" that serves as a image signal-transmitting source can include a receiver in digital broadcasting and a reproduction apparatus for commercial content such as a Blu-ray disc player. In this embodiment, the first information such as the power generation amount and the power storage amount is obtained from the power generation apparatus (described later) via the communication unit 505. Moreover, the control information derived from the first information such as the power generation amount is transmitted from the communication unit 505 to the external device serving as a control target. Examples of the "external device" that serves as the control target can include a game console that receives the control information from the image display apparatus 100 and controls the character, for example.

The communication unit 505 has an arbitrary configuration. For example, the communication unit 505 can be configured according to a communication system used for operations of transmission/reception to/from an external device as the other party of communication. The communication system may be wired or may be wireless. Examples of the communication standards used here include MHL (Mobile High-definition Link), USB (Universal Serial Bus), HDMI (registered trademark) (High Definition Multimedia Interface), Wi-Fi (registered trademark), Bluetooth (registered trademark) communication, BLE (Bluetooth (registered trademark) Low Energy) communication, ultra-low-power wireless communication such as ANT and ZigBee (the communication unit 505 may use SOC (System on a chip) combining a plurality of ultra-low-power wireless communication modules), infrared communication, human body communication, and signal transmission through an electroconductive fiber.

Alternatively, the communication unit 505 may be a cellular radio transceiver, which operates according to the standards such as W-CDMA (Wideband Code Division Multiple Access) and LTE (Long Term Evolution).

The storage unit 506 is a large-capacity storage device formed of an SSD (Solid State Drive) or the like. The storage unit 506 stores application programs and various types of data executed by the control unit 501. Examples of the stored data can include the first information such as an image captured by the external camera 512 (described later), image content reproduced and displayed by the display unit 509 (described later), and the power generation amount, the power storage amount, and the like that are received from the power generation apparatus (described later), the second information such as the user-monitoring information and the environment-monitoring information that are obtained by converting the first information such as the power generation amount, the third information such as the action-inducing information derived based on the second information (or the first information), and displayed images of the first to third information.

An image processing unit 507 further performs signal processing, such as image quality correction, on image signals output from the control unit 501 and also converts the image signals into those having resolution conforming to the screen of the display unit 509. A display drive unit 508 then selects pixels of the display unit 509 in a sequential manner on a row-by-row basis and scans the pixels in a line-sequential manner, to supply pixel signals based on the image signals subjected to the signal processing.

The display unit 509 includes a display panel formed of a microdisplay such as a liquid-crystal display and an organic EL device or a laser scanning display such as a retinal direct-drawing display. A virtual image optical unit 510 projects the displayed image of the display unit 509 in an enlarged manner, to cause the user to observe the image as an enlarged virtual image.

Moreover, the external display unit 515 includes a display screen facing the outside of the image display apparatus 100 (opposite to the face of the user wearing it) and can display an image the same as or different from that of the display unit 509 to other users. For a detailed configuration of the external display unit 515, please see, for example, Japanese Patent Application No. 2012-200902 and Japanese Patent Application No. 2012-200903, assigned to the applicant hereof.

A sound processing unit 513 further performs sound quality correction and sound amplification on sound signals output from the control unit 501 and performs signal processing on input sound signals and the like. A sound input and output unit 514 then outputs the sounds subjected to the sound processing to the outside, and inputs sounds from the microphones (described above).

The image display apparatus 100 according to this embodiment serves not only as the display apparatus that displays the image content but also as a monitoring device. The image display apparatus 100 converts, based on a principle for inducing electrical power, the power generation amount as the first information that is obtained from the power generation apparatus into the second information such as the physical quantity used for power generation. The image display apparatus 100 uses this second information as sensor information for monitoring the user or environment in which the power generation apparatus is installed. Specifically, the image display apparatus 100 uses the amount of exercise or the like of the user that is converted from the power generation amount as the user-monitoring information and uses the ultraviolet intensity, the radio-wave intensity, or the like that is converted from the power generation amount as the environment-monitoring information, and presents them to the user.

B. Monitoring System of Power Generation Condition

Although not shown in FIG. 5, the image display apparatus 100 is configured to be driven by a storage element such as a secondary battery as a main power source, considering the use in an environment without a power supply outside the home. Moreover, the secondary battery has a limited operational time, and hence a power generation apparatus that obtains electrical power for charging the secondary battery by power generation is used together.

A design that the power generation apparatus is incorporated in the image display apparatus 100 is also conceivable. However, in this embodiment, considering a case where the image display apparatus 100 is used by being mounted on the head of the user or the user goes out with the image display apparatus 100, the power generation apparatus is installed outside the image display apparatus 100 in order to prevent the main body of the image display apparatus 100 from increasing a weight burden on the user.

The power generation apparatus performs energy harvesting by using vibrations, sunlight, heat, environmental electromagnetic waves, or the like as an energy source. Although the power generation apparatus is installed outside of the image display apparatus 100, various locations therefor are conceivable. The power generation apparatus may be installed on the user. The power generation apparatus may be installed on a person other than the user, a creature such as a companion animal, a building, or a moving body such as a vehicle and an aircraft. Alternatively, the power generation apparatus may be installed in a tool used by the user or person other than the user or in a location where the user or person other than the user is located. In any cases, it is also conceivable that a plurality of available power generation apparatuses are present around the single image display apparatus 100.

In order to avoid a wasted action of performing replacement with a secondary battery having an insufficient power storage amount, it is favorable that the user checks the power storage amount or the power generation amount of the secondary battery on the side of the power generation apparatus and performs replacement with the secondary battery having the sufficient power storage amount or performs battery replacement preferentially with the power generation apparatus having a larger power generation amount.

As described above, the power generation apparatus is installed outside the image display apparatus 100. Therefore, the image display apparatus 100 cannot directly know a power generation condition of the power generation apparatus. In view of this, in this embodiment, the following configuration is employed. Specifically, the image display apparatus 100 includes an information input means for inputting the first information such as the power storage amount and the power generation amount of the secondary battery in one or more power generation apparatuses. The image display apparatus 100 appropriately converts the input first information into the second information. The image display apparatus 100 presents it to the user via the display unit 509. As a matter of course, the first information or the second information may be presented to the user not via the display unit 509 but via the sound input and output unit 514 using audio guidance.

Thus, the user of the image display apparatus 100 can check the current power generation amount of the power generation apparatus and the power storage amount of the secondary battery without stopping the use of the image display apparatus 100. Moreover, for example, when the power storage amount of the battery in use is lowered, the user can properly judge with which of the power generation apparatuses the user should replace the battery. Moreover, from the display of the second information such as the user-monitoring information such as the amount of exercise of the user and the environment-monitoring information such as ultraviolet intensity and radio-wave intensity, the user can know an environment that is out of a range that the user can perceive or difficult to perceive.

If the power generation apparatus is installed on the body of the user, power generation can be automatically performed by the user using human ordinary actions such as walking, that is, transforming vibrations or motions when the user walks into electrical power. For example, the power generation apparatus may be installed in either one or both of the left and right shoes of the user. As a matter of course, the power generation apparatus that performs the energy harvesting may be installed in a position other than the shoes. For example, the power generation apparatus can be installed on various articles that the user wears, for example, a wristwatch, a bracelet, an arm band, or a wrist band that the user wears on the wrist, a ring that the user puts on the finger, an accessory such as an anklet and a necklace, clothes that the user wears, pants that the user wears, a rucksack that the user carries on the back, a belt or a waist pouch that the user puts around the waist, or a bag that the user carries. The image display apparatus 100 converts, based on the principle of the power generation unit for inducing electrical power, the first information such as the power generation amount of the power generation apparatus installed on the body of the user into the second information such as the amount of exercise of the user, and monitors the activity of the user.

On the other hand, if the power generation apparatus is installed in a location other than the body of the user, the environment-monitoring information that is out of a range that the user can perceive or difficult to perceive can be obtained by converting the first information such as the power generation amount into the second information.

Figure 6:
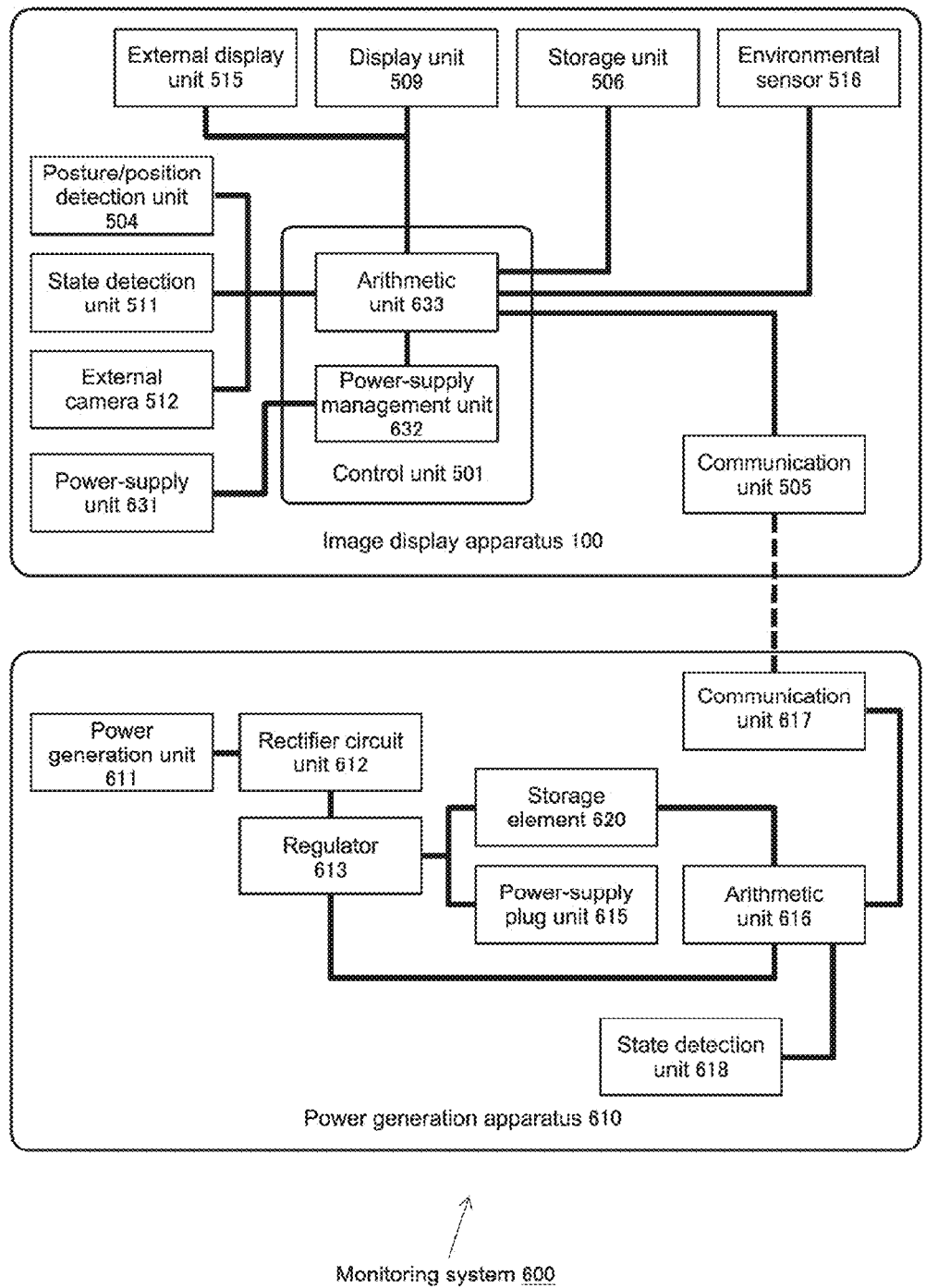
FIG. 6 is a diagram schematically showing a functional configuration of a power generation condition-monitoring system 600.

FIG. 6 shows a functional configuration of a monitoring system 600 in a power generation condition. The monitoring system 600 shown in the figure is formed of the image display apparatus 100 (or the image display apparatus 300) and a power generation apparatus 610. For the sake of simplification of the illustration, only one power generation apparatus 610 is illustrated. However, it is also conceivable that a plurality of power generation apparatuses are installed in the surrounding environment of the user.

The power generation apparatus 610 includes a power generation unit 611, a rectifier circuit unit 612, a regulator 613, a power-supply plug unit 615, an arithmetic unit 616, a communication unit 617, a state detection unit 618, and a storage element 620. The power generation apparatus 610 (or at least the power generation unit 611 of the power generation apparatus 610) is installed on the body of the user or person other than the user, an article put on the body, a nonhuman animal such as a companion animal, a tool used by the user or person other than the user, a building such as a house or a factory, a moving body such as a vehicle and an aircraft, and a land such as a farm and a field where sports are played.

The power generation unit 611 is formed of a vibration or motion power generator (electrostatic type, electromagnetic type, inverse-magnetostrictive type, or piezoelectric type) that generates electrical power using vibrations, a solar-cell power generation element that generates electrical power using sunlight, an ultraviolet-ray power generation element that generates electrical power using ultraviolet rays, an infrared-ray power generation element that generates electrical power using infrared rays, a thermoelectric conversion element that generates electrical power using a temperature difference (including power generation using the Seebeck effect, the Thomson effect, or the like, power generation using a thermoelectric element or pyroelectric effect, thermomagnetic power generation, and the like), an enzymatic cell that generates electrical power using sweat of a creature such as a person (power generation element that generates electrical power using enzyme reaction), a power generation element using an ion concentration difference, a power generation element that generates electrical power using radioactive rays, a radio-wave power generation element that induces electrical power using radio waves (far electromagnetic field), a near electromagnetic field-used power generation element that induces electrical power due to an electromagnetic field in a neighboring region, which includes electromagnetic induction and electrostatic induction, or a power transmission device using magnetic field resonance, electromagnetic induction, or electric field coupling, and the like.

Note that examples of the power generation element based on sunlight can include a silicon-based solar cell using a crystalline silicon (including monocrystalline, polycrystalline, microcrystalline, and amorphous), a compound-based solar cell such as a CdTe-based solar cell, a solar cell using an organic compound such as a dye sensitized solar cell, and an iron-sulfide-based solar cell. Among them, in particular, the silicon-based solar cell and the dye sensitized solar cell can generate a large amount of power. Some of the ultraviolet-ray power generation elements and infrared-ray power generation elements are of a type that allows visible light to pass therethrough and generates electrical power using invisible light such as ultraviolet rays, infrared rays, and the like.

The rectifier circuit unit 612 rectifies a current generated by the power generation unit 611. The regulator 613 increases or decreases the pressure such that the voltage after the rectification becomes a level suitable for power storage. The obtained direct-current voltage is supplied to the storage element 620 and the power storage is performed. Alternatively, the power storage of the storage element 620 may be performed by using electrical power obtained from a commercial power supply via the power-supply plug unit 615 as an alternative means of the power generation unit 611 that obtains electrical power by power generation. The storage element 620 includes, for example, a capacitor, a secondary battery, a spring, and a heat storage material. The storage element 620 stores electrical power generated by the power generation unit 611 or stores it as energy.

Alternatively, the power generation apparatus 610 may include the state detection unit 618 as an optional component. The state detection unit 618 includes a gyroscope, an acceleration sensor, a velocity sensor, a GPS sensor, a temperature sensor, a moisture sensor, a radiation sensor, an illuminance sensor, an infrared sensor, a pressure sensor, a geomagnetic sensor, a Doppler sensor, a gas sensor, a camera, and the like. The state detection unit 618 obtains the state information such as the posture and position and the surrounding environment of the power generation apparatus 610.

The arithmetic unit 616 performs a charge/discharge control of the storage element 620. Moreover, the arithmetic unit 616 monitors the power storage amount of the storage element 620 based on voltages at both ends, a charging current, or the like of the storage element 620. While monitoring the power storage amount, the arithmetic unit 616 detects whether or not the power storage amount of the storage element 620 is equal to or smaller than a threshold value and whether or not the storage element 620 is fully charged, and calculates an estimated period of time for fully charging the storage element 620. Alternatively, the arithmetic unit 616 may monitor the power generation amount of the power generation apparatus 610 by monitoring a voltage variation at both ends of a condenser (not shown) in the rectifier circuit unit 612.

The communication unit 617 performs data communication with the communication unit 505 on the side of the image display apparatus 100. For example, the first information that is basic data on power generation such as the power storage amount and the power generation amount that is obtained by the arithmetic unit 616 to the image display apparatus 100 via the communication unit 617. Besides the first information, the transmitted information can include whether or not the power storage amount of the storage element 620 is equal to or smaller than the threshold value, whether or not the storage element 620 is fully charged, and the estimated period of time for fully charging the storage element 620. Depending on needs, the state information detected by the state detection unit 618 is transmitted to the image display apparatus 100 via the communication unit 617.

For communicating with the image display apparatus 100, the communication unit 617 may use MHL or USB, HDMI (registered trademark), Wi-Fi (registered trademark), Bluetooth (registered trademark) communication, BLE (Bluetooth (registered trademark) Low Energy) communication, ultra-low-power wireless communication such as ANT and ZigBee (may be SOC (System on a chip) combining a plurality of ultra-low-power wireless communication modules), or infrared communication. Alternatively, if the power generation apparatus 610 is installed on the body of the user such as the shoe, the communication unit 617 may transmit data to the image display apparatus 100 through the medium of the body of the user using the human body communication. As a matter of course, the communication unit 617 may transmit data to the image display apparatus 100 not by wireless communication but by wired communication (including signal transmission through an electroconductive fiber).

Note that the communication unit 617 may be constantly operated and transfer the first information on power generation in real time or may be intermittently operated and transfer the first information.

On the other hand, on the side of the image display apparatus 100, a power-supply unit 631 includes a secondary battery and the like and supplies driving electrical power to each unit of the image display apparatus 100. The secondary battery of the power-supply unit 631 is, for example, compatible with the secondary battery serving as the storage element 620.

A power-supply management unit 632 performs power-supply management in the image display apparatus 100. For example, the power-supply management unit 632 manages residual capacity and operational time of the secondary battery used in the power-supply unit 631 and an replacement period of the secondary battery in use.

An arithmetic unit 633 performs arithmetic processing on the first information that is the basic data on power generation, which is received from the power generation apparatus 610 via the communication unit 505, and controls output of the processing result to the display unit 509 for display. If the information received from the power generation apparatus 610 includes information on a power storage state of the storage element 620 such as whether or not the power storage amount of the storage element 620 is equal to or smaller than the threshold value, whether or not the storage element 620 is fully charged, and the estimated period of time for fully charging the storage element 620, this may also be displayed on the display unit 509 and presented to the user.

The arithmetic unit 633 executes, for example, the power generation information-processing program. The arithmetic unit 633 converts, based on the principle of the power generation unit for inducing electrical power, the power generation amount that is the first information obtained from the power generation apparatus 610 into the second information such as the user-monitoring information such as the amount of exercise of the user and the environment-monitoring information such as ultraviolet intensity and radio-wave intensity. Monitoring of the user and monitoring of the surrounding environment is achieved by outputting the second information to the display unit 509 or the external display unit 515 for display. Specifically, when the power generation amount of the power generation apparatus 610 is converted into the second information such as an amount of exercise or a metabolic rate (calorie consumption) of the user (or an animal on which the power generation apparatus 610 is installed) and the intensity of electromagnetic waves or radio waves, antenna strength, a water flow, an airflow, an amount of solar radiation, and temperature in a location where the power generation apparatus 610 is installed, a virtual image indicating the second information is combined with the real image showing the location where the power generation apparatus 610 is installed (e.g., to be superimposed on the location where the power generation apparatus 610 is installed, which is displayed on the head-mounted display or the like to the user in a see-through or video-see-through manner) and monitoring is performed.

When performing, for example, the calculation for converting the power generation amount, the arithmetic unit 633 uses information detected by the posture/position detection unit 504, the state detection unit 511, and the environmental sensor 516. Additionally, a captured image of the external camera 512 may be appropriately input and used for display processing of the monitoring information.

Additionally, the arithmetic unit 633 may save the first information such as the power generation amount that is received from the power generation apparatus 610, the second information such as the user-monitoring information and the environment-monitoring information that is converted from the first information, the displayed image of the first information or the second information that is outputted to and displayed on the display unit 509 or the external display unit 515, and the like in the storage unit 506 or the like depending on needs or may transfer them to the outside via the communication unit 505.

Additionally, the arithmetic unit 633 may display the displayed image as that of the display unit 509 also on the external display unit 515 and present (publicly show) the first information such as the power generation amount that is received from the power generation apparatus 610 and the second information such as the user-monitoring information, the environment-monitoring information, and the like that is converted from the first information.

The arithmetic unit 633 can also generate, based on the second information obtained by converting the first information (or the first information itself) such as the power generation amount received from the power generation apparatus 610, the third information such as the action-inducing information for inducing the action of the user and the control information for controlling the image display apparatus 100 itself or other devices.

The arithmetic unit 633 can display the action-inducing information on the display unit 509 or the external display unit 515 and induce the user or surrounding user to take a desired action. The arithmetic unit 633 can also control, based on the control information, a state, a motion, or an action of a CG character such as an avatar in a game. Additionally, the arithmetic unit 633 may transmit the control information to the external device (not shown) as the control target via the communication unit 505 and control the external device (described later).

Note that operations of the power-supply management unit 632 and the arithmetic unit 633 are, for example, achieved according to the application programs (power generation information-processing program, monitoring processing program, and the like) executed by the control unit 501. As a matter of course, the power-supply management unit 632 and the arithmetic unit 633 can also be configured as dedicated hardware.

According to the monitoring system 600 of this embodiment, information that is out of a perception range for the user wearing the image display apparatus 100 or difficult to perceive can be presented to the user based on the first information such as the power generation amount that is obtained on the side of the power generation apparatus 610 and the second information converted from the first information. On the side of the image display apparatus 100, the perception range of the user can be extended by arranging and presenting information pieces obtained from the power generation apparatus 610.

In general, in order to monitor the user or environment, an external sensing device that measures a state of the user or environment is necessary. In order to measure various states, it is necessary to provide a plurality of sensing devices. It contributes to an increase in size of the apparatus. As a result, problems such as an increase of power consumption and an increase of failure rate occur. The external sensing device that consumes electrical power has a limited continuous use time. Every time the battery is exhausted, charging, battery replacement, replacement of the sensing device itself, and the like become necessary. The external sensing device favorably has a small size so as not to interfere with the exercise and life activity of the user. However, the capacity of a mountable battery is limited, and hence the continuous use time is inevitably shortened.

In contrast, the monitoring system 600 according to this embodiment is configured to convert the first information such as the power generation amount obtained from the power generation unit 611 into the second information such as the amount of exercise and perform the monitoring. In other words, the power generation unit 611 itself serves as the sensing device and a power-supply does not have to be provided. Therefore, the limitation on the continuous use time is overcome and the power generation apparatus does not have to be increased in size for the battery. Moreover, by configuring power consumption of the state detection unit 618 formed of various sensors to be equal to or smaller than electrical power generated by the power generation unit 611, the limitation on the continuous use time is overcome and the power generation apparatus 610 does not have to be increased in size for the battery.

Example 1

A monitoring system according to Example 1 positively uses information from the power generation apparatus mainly installed on the user and monitors a state of the user such as health information from a living environment of the user. The power generation apparatus includes at least one of a vibration or motion power generator (electrostatic type, electromagnetic type, inverse-magnetostrictive type, or piezoelectric type) that generates electrical power using vibrations, a solar-cell power generation element that generates electrical power using sunlight, an ultraviolet-ray power generation element that generates electrical power using ultraviolet rays, an infrared-ray power generation element that generates electrical power using infrared rays, a thermoelectric conversion element that generates electrical power using a temperature difference, an enzymatic cell that generates electrical power using sweat of a creature such as a person, a power generation element using an ion concentration difference, a power generation element that generates electrical power using radioactive rays, and a radio-wave power generation element that induces electrical power using radio waves as the power generation unit. For example, the power generation apparatus is installed on the body of the user. The image display apparatus receives first information such as a power generation amount from the power generation apparatus. Then, the image display apparatus converts the first information into second information indicating a physical quantity relating to movement vibrations of the power generation apparatus, ultraviolet intensity, radio-wave intensity, sunlight intensity, an environmental temperature, a degree of atmospheric pollution or a living environment of the user such as a basal metabolic rate, an amount of exercise, and a stress (mental strain). In addition, the image display apparatus derives, from this second information, action-inducing information relating to health and life of the user, the surrounding user, or the like, for example, "protect the head," "go out of a building," "enter a building," "do more exercise," and "be relaxed" as the third information and displays it on the screen.

Figure 7:
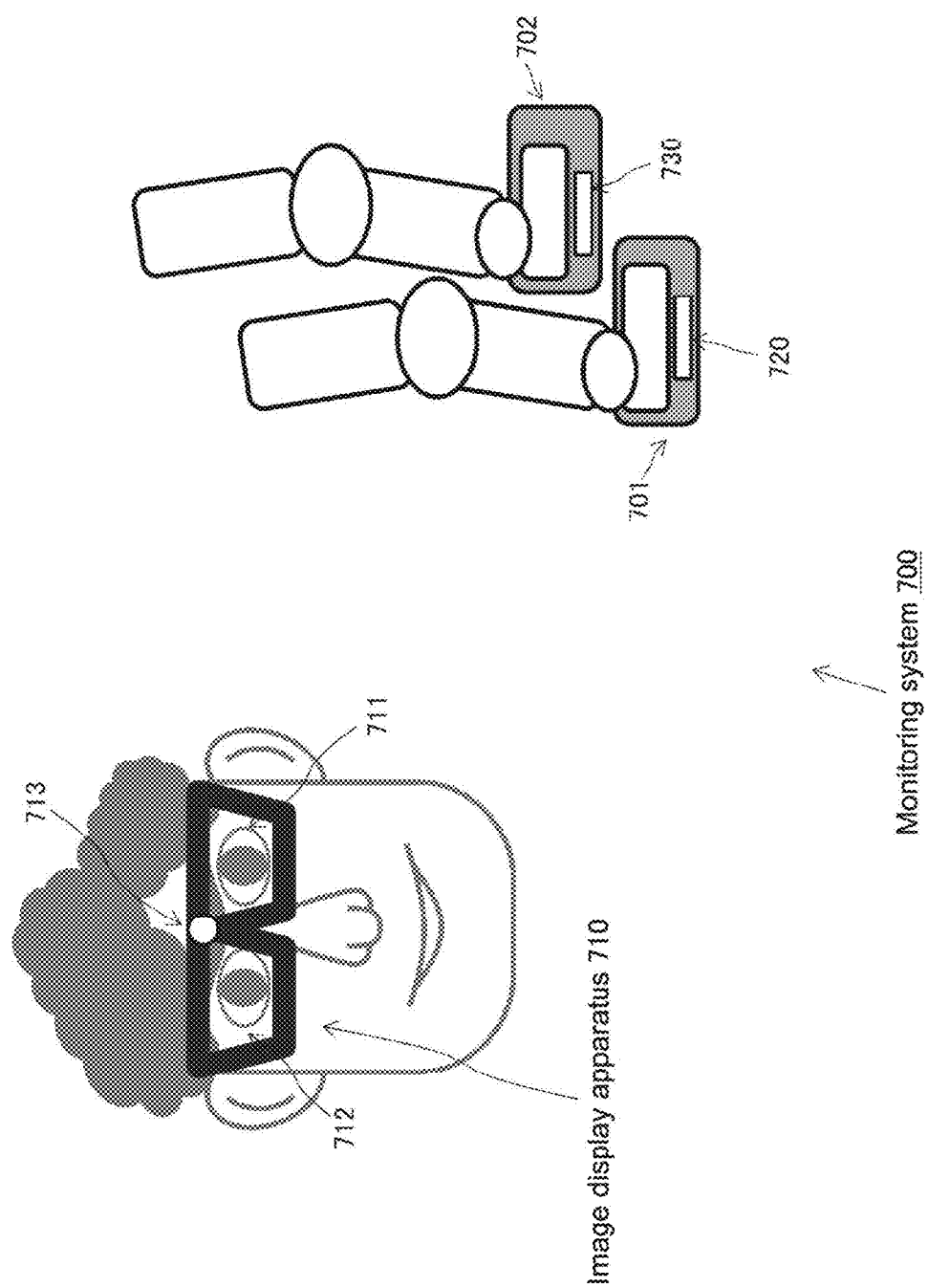
FIG. 7 is a diagram schematically showing a configuration of a monitoring system 700 according to Example 1.

FIG. 7 schematically shows a configuration of a monitoring system 700 according to Example 1. The monitoring system 700 shown in the figure is formed of an image display apparatus (head-mounted display) 710 that is used by being mounted on the head or face of the user, and two power generation apparatuses 720 and 730 installed in shoes 701 and 702 worn on the left and right feet of the user, respectively. The monitoring system 700 basically has the functional configuration shown in FIG. 6. However, in FIG. 7, the system 700 is shown in an abstract manner as it is operated. Note that, in this specification, for the sake of description, only an example in which the power generation apparatuses 720 and 730 are installed in both the shoes 701 and 702 worn on the both feet of the user will be discussed. However, as a matter of course, an example in which the power generation apparatus is installed in only the shoe worn on either one of the left and right feet is conceivable. If one of the left and right feet of the user is an artificial foot, an example in which the power generation apparatus 720 or 730 is installed in the shoe worn on the artificial foot or the artificial foot itself is also conceivable.

The image display apparatus 710 includes two display units 711 and 712 that present the left eye image and the right eye image to the left and right eyes of the user and an acceleration sensor 713 that measures an acceleration acting on the head of the user.

Each of the power generation apparatuses 720 and 730 includes a power generation unit, a storage element, and a communication unit (not shown). The power generation unit is formed of the vibration or motion power generator (electrostatic type, electromagnetic type, inverse-magnetostrictive type, or piezoelectric type) that generates electrical power using vibrations or the thermoelectric conversion element that generates electrical power using a temperature difference. In this example, the power generation unit generates electrical power according to a motion of the foot of the user. The storage element is formed of, for example, a capacitor, a secondary battery, a spring, or a heat storage material. The power generation unit stores electrical power obtained by power generation or stores it as energy. The communication unit transmits the first information including the power generation amount and the power storage amount of the power generation unit to the image display apparatus 710. The communication unit can use a communication means such as wireless communication such as Wi-Fi, human body communication through the medium of the body of the user, and wired communication (including signal transmission through an electroconductive fiber). The communication unit may be constantly operated and transfer the first information in real time or may be intermittently operated and transfer the first information. The data may be directly exchanged between the left and right power generation apparatuses 720 and 730 or either one of the power generation apparatuses 720 and 730 may transfer both of power generation amounts as a single first information piece to the image display apparatus 710 at once.

Figure 8A:
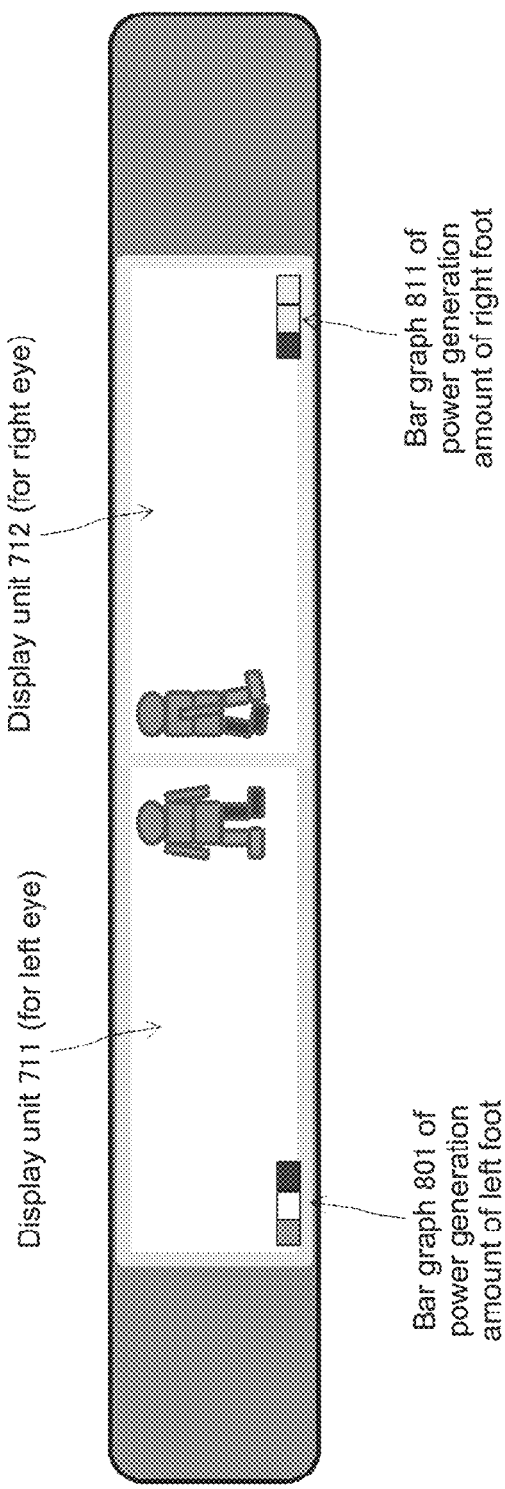
FIG. 8A is a diagram showing a display example in Example 1 (example in which only power generation amount is displayed).

The image display apparatus 710 displays the first information such as the power generation amount and the power storage amount received from each of the power generation apparatuses 720 and 730 on at least either one of the left and right display units 711 and 712. For example, as shown in FIG. 8, a power generation amount 801 of the power generation apparatus 720 installed in the shoe of the left foot may be displayed on the display unit 711 for the left eye and a power generation amount 802 of the power generation apparatus 730 installed in the shoe of the right foot may be displayed on the display unit 712 for the right eye.

Figure 8B:
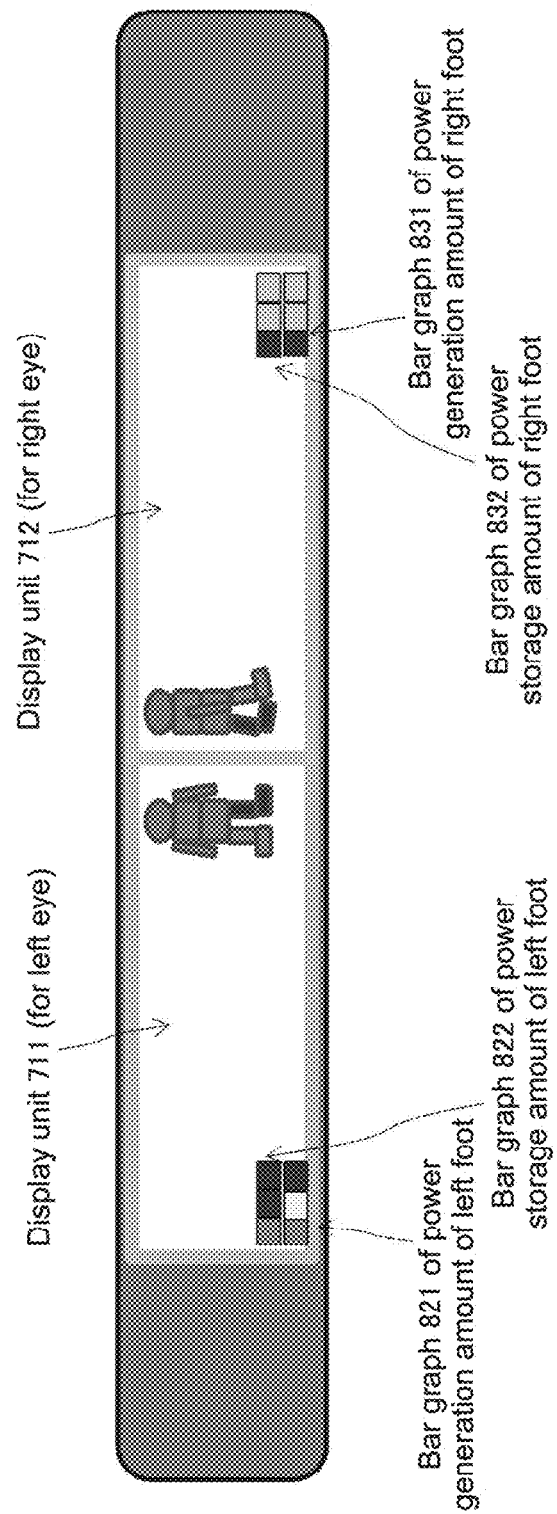
FIG. 8B is a diagram showing a display example in Example 1 (example in which power generation amount and power storage amount are displayed).

Each of the power generation apparatuses 720 and 730 has a power generation amount according to an amount of exercise, a speed, an acceleration, a pedal-in force, or a metabolic rate (calorie consumption) of each of the left and right feet of the user and a power storage amount substantially corresponding to an integrated value thereof. The arithmetic unit 633 may convert the power generation amounts 801 and 802 received as the first information from the power generation apparatuses 720 and 730, respectively, into the second information such as an amount of exercise, a speed, an acceleration, a pedal-in force, and a metabolic rate (calorie consumption) of the left and right feet of the user and display it. In the example shown in FIG. 8A, the power generation amount changing over time (or the physical quantity converted from the power generation amount) of each of the power generation apparatuses 720 and 730 is shown by each of bar graphs 801 and 811 for the power generation apparatus 720 installed in the shoe of the left foot and the power generation apparatus 730 installed in the shoe of the right foot. FIG. 8B shows an example in which bar graphs 821 and 831 of the power generation amounts of the power generation apparatuses 720 and 730 and bar graphs 822 and 832 of the power storage amounts of the power generation apparatuses 720 and 730 are added and displayed.

As shown in FIG. 7, if the power generation apparatuses 720 and 730 are installed in the shoes, the first information such as the power generation amount can be converted into the second information such as the amount of exercise of the foot on the side of the image display apparatus 710. As another example, if the power generation apparatus is installed in a wristwatch, bracelet, arm band, or wrist band put on the arm of the user, the first information such as the power generation amount can be converted into the second information such as the amount of exercise of the arm. If the power generation apparatus is installed in the ring fitted on the finger, the first information such as the power generation amount can be converted into the second information such as the amount of exercise of the finger. If the power generation apparatus is installed in a rucksack that the user carries on the back or a belt or a waist pouch that the user puts around the waist, the first information such as the power generation amount can be converted into the second information such as the amount of exercise of the torso, the waist, or the vicinity of the trunk.

According to the monitoring system 700 of this example, the second information that is out of a perception range for the user wearing the image display apparatus 710 or difficult to perceive can be presented to the user based on the first information such as the power generation amount that is obtained on each of the power generation apparatuses 720 and 730 and the second information such as the amount of exercise that is converted from the first information. On the side of the image display apparatus 710, the perception range of the user can be extended by arranging and presenting information pieces obtained from the power generation apparatuses 720 and 730.

Note that a method of additionally providing each of the power generation apparatuses 720 and 730 with the velocity sensor, the acceleration sensor, and the pressure sensor, to thereby directly measure an amount of information that corresponds to the above-mentioned second information such as the speed, the acceleration, and the pedal-in force applied on the left and right feet is also conceivable. However, with such sensors, the component cost of the power generation apparatuses 720 and 730 increases and power consumption of the power generation apparatuses 720 and 730 also increases. As a result, the continuous use time is inevitably shortened. In contrast, as in this example, according to the method of transmitting the first information such as the power generation amount from the power generation apparatuses 720 and 730 and converting the first information received on the side of the image display apparatus 710 into the second information such as the amount of exercise of the user, the apparatus cost can be reduced. Moreover, the power generation unit itself in each of the power generation apparatuses 720 and 730 serves as the sensing device and a power-supply does not have to be provided. Therefore, the power consumption of the entire system 700 is reduced. The limitation on the continuous use time is overcome and the power generation apparatuses 720 and 730 do not have to be increased in size for the batteries.

Figure 9:
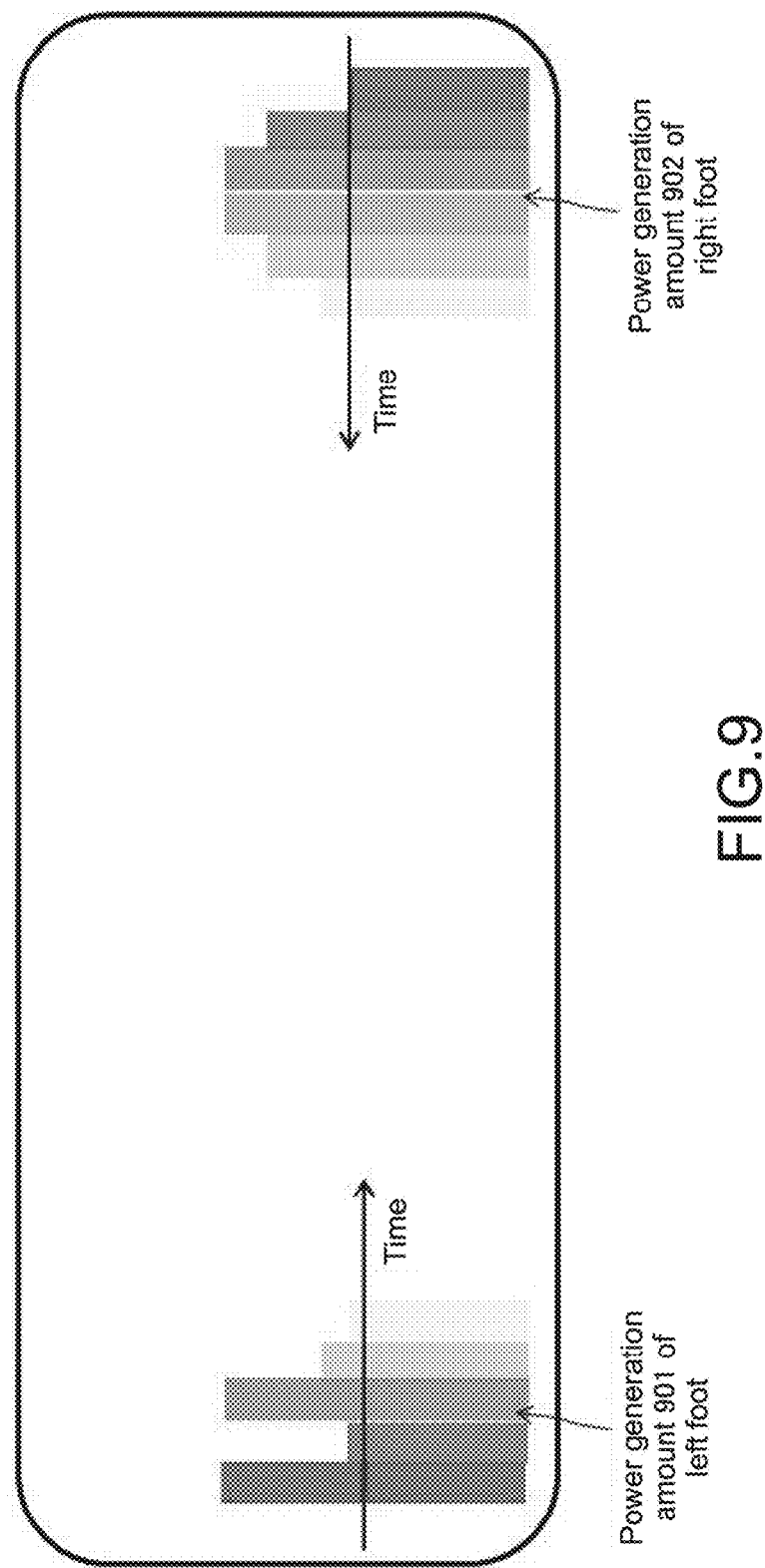
FIG. 9 is a diagram showing another display example in Example 1.

FIG. 9 shows another display example of the first information received from each of the power generation apparatuses 720 and 730 installed in the shoes of the left and right feet. In the example shown in the figure, the image display apparatus 710 displays the first information received from the power generation apparatus 720 installed in the shoe of the left foot and the power generation apparatus 730 installed in the shoe of the right foot, in the form of bar graphs 901 and 902 each indicating a power generation amount for each unit time (or a physical quantity converted from the power generation amount. Note that it is assumed that the unit time can be set to an arbitrary period of time, for example, 1 minute, 5 minutes, 30 minutes, or 1 hour.

Figure 10:
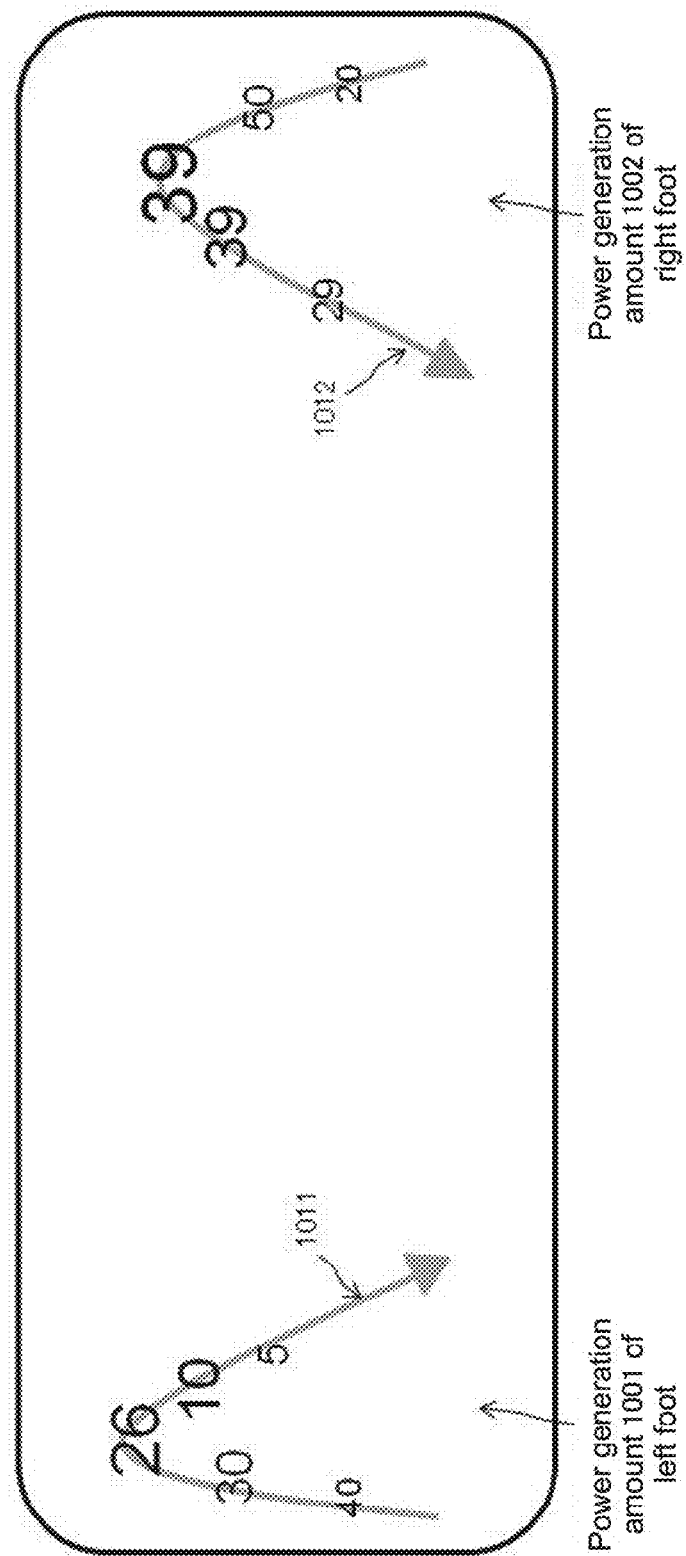
FIG. 10 is a diagram showing still another display example in Example 1.

FIG. 10 shows still another display example of the first information received from each of the power generation apparatuses 720 and 730 installed in the shoes of the left and right feet. In the example shown in the figure, the image display apparatus 710 sequentially receives, from the power generation apparatus 720 installed in the shoe of the left foot, the power generation amount as well as a sensor value of the acceleration sensor or the like as the first information. The sensor value is converted into a trajectory formed by a movement of the left foot as the second information. Then, a power generation amount calculated in each location (or a physical quantity converted from the power generation amount) 1001 is numerically displayed on an animation 1011 drawing the trajectory of the left foot. Similarly, the image display apparatus 710 sequentially receives, from the power generation apparatus 730 installed in the shoe of the right foot, a power generation amount and a sensor value of the acceleration sensor or the like as the first information. The sensor value is converted into a trajectory formed by a movement of the left foot as the second information. Then, a power generation amount calculated in each location (or a physical quantity converted from the power generation amount) 1002 is numerically displayed on an animation 1012 drawing the trajectory of the right foot.

Figure 11A:
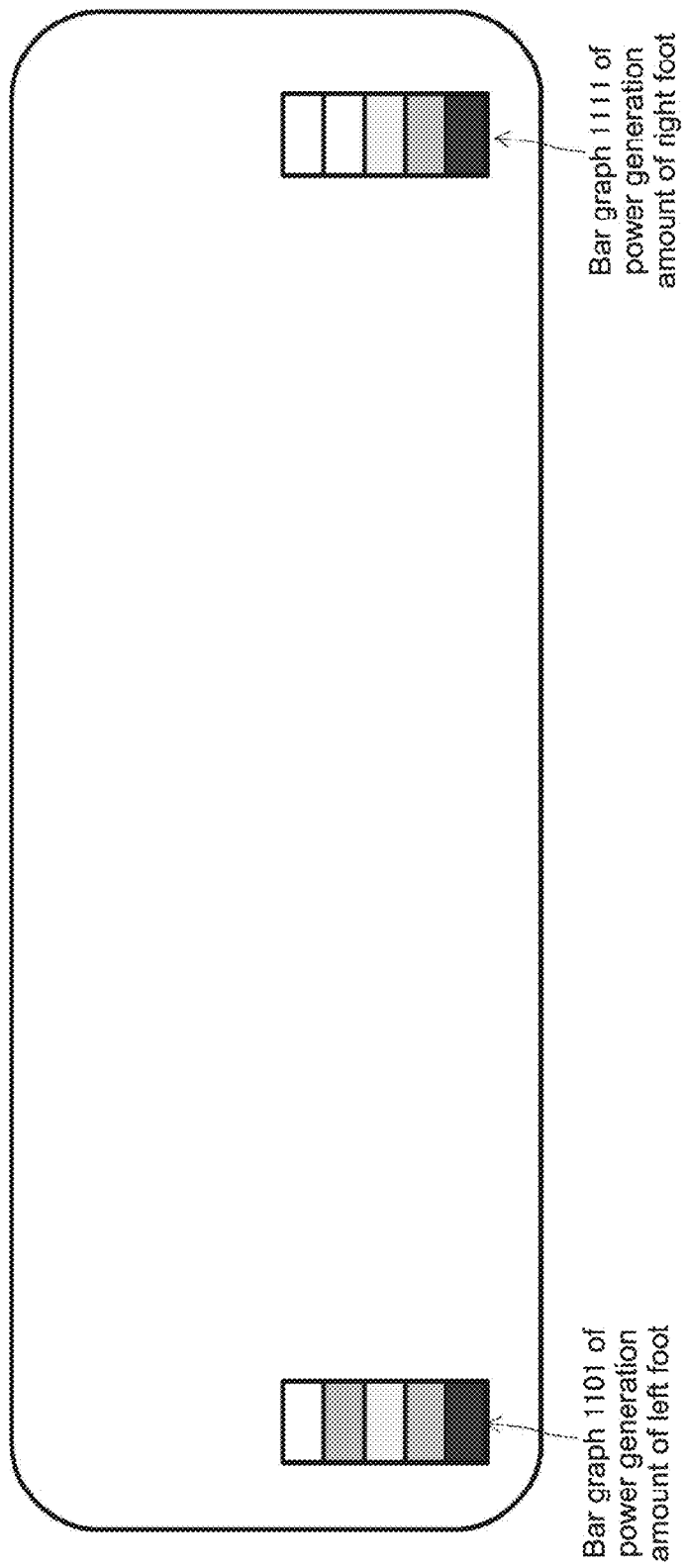
FIG. 11A is a diagram showing still another display example in Example 1 (example in which only power generation amount is displayed).
Figure 11B:
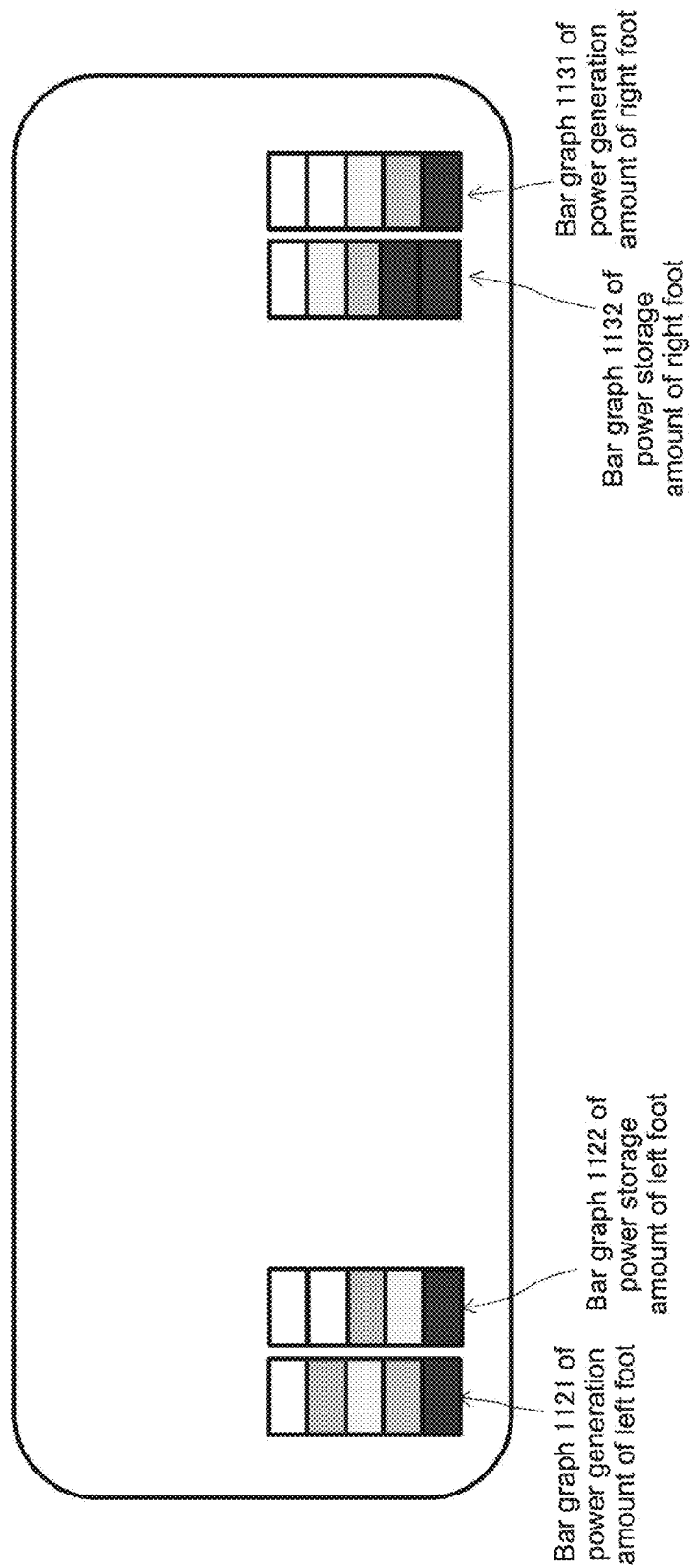
FIG. 11B is a diagram showing still another display example in Example 1 (example in which power generation amount and power storage amount are displayed).

FIG. 11 shows still another display example of the first information received from each of the power generation apparatuses 720 and 730 installed in the shoes of the left and right feet. In the example shown in FIG. 11A, as the first information from the power generation apparatus 720 installed in the shoe of the left foot and the first information from the power generation apparatus 730 installed in the shoe of the right foot, a power generation amount changing over time (or a physical quantity converted from the power generation amount) is shown by each of bar graphs 1101 and 1111. Every time the first information is received from each of the power generation apparatuses 720 and 730 and processed, the display of the bar graphs 1101 and 1111 is updated. FIG. 11B shows an example in which the bar graphs 1121 and 1131 of the power generation amounts of the power generation apparatuses 720 and 730 and the bar graphs 1122 and 1132 of the power storage amounts of the power generation apparatuses 720 and 730 are together displayed, respectively. Every time the first information is received from each of the power generation apparatuses 720 and 730 and processed, the display of the bar graphs 1121, 1122, 1131, and 1132 is updated.

Due to deterioration of shoe soles or deterioration of the shoes themselves, power generation efficiency of the power generation apparatuses 720 and 730 installed in the shoes is lowered. In view of this, the image display apparatus 710 may convert the power generation amount obtained as the first information from each of the power generation apparatuses 720 and 730 into a deterioration state of each of the left and right shoes as the second information. The deterioration state of the shoe of the left foot may be displayed on the display unit 711 for the left eye and the deterioration state of the shoe of the right foot may be displayed on the display unit 712 for the right eye.

Each of the power generation apparatuses 720 and 730 generates electrical power according to the amount of exercise of each of the left and right feet. Thus, on the side of the image display apparatus 710, the arithmetic unit 633 can convert the power generation amount received from each of the power generation apparatuses 720 and 730 into acceleration information of each of the left and right feet. As described above, the image display apparatus 710 includes the acceleration sensor 713, and hence the monitoring system 700 as a whole can perform acceleration measurement at three points of the head, right foot, and left foot of the user.

Due to such acceleration measurement at the three points, it is possible to determine not only an absolute acceleration applied on the head of the user but also a relative acceleration of each of the right foot and the left foot. As a result, the posture of the body of the user can be more accurately known. Thus, data important for sports such as data on trunk balance can be more precisely obtained as the third information.

For example, before or after performing a sport (tennis, golf, or the like) in which the balance of muscles of the limbs on one side of the body is lost (the left and right motions are not even), it is general to perform an exercise on a side opposite to the often used side in order to restore the muscle balance. When performing such a balance restoration exercise, it is difficult for the user to judge what amount of exercise is needed to perform the same amount of exercise on left- and right-hand sides of the body according to his/her sense. In contrast, according to the monitoring system 700 of this example, the image display apparatus 710 can convert the power generation amounts received from the power generation apparatuses 720 and 730 installed in the shoes into the amounts of exercise of the user and display the amounts of exercise of the left and right feet on the left and right display units 711 and 712 (see FIG. 8). Thus, the user can carry out the balance restoration exercise by visually observing the amount of exercise of each of the left and right feet displayed on the image display apparatus 710 and moving such that the both becomes equal to each other.

In the image display apparatus 710, by the arithmetic unit 633 converting the power generation amount obtained as the first information from each of the power generation apparatuses 720 and 730 into an acceleration of each of the left and right feet as the second information and compares the both values, the posture balance of the user can be estimated. If each of the power generation apparatuses 720 and 730 includes an actuator (not shown) for posture balance correction, the image display apparatus 710 generates control information for driving the actuator of each of the power generation apparatuses 720 and 730 so as to correct the posture balance of the user based on a result of the comparison of the converted accelerations of the left and right feet. The image display apparatus 710 can transmit the control information for the actuator to each of the power generation apparatuses 720 and 730, to thereby control the posture balance. If the power generation unit also serves as the actuator, rather than generating electrical power by the power generation unit of each of the power generation apparatuses 720 and 730, the power generation unit may be supplied with electrical power and used as the actuator. If the actuator is mainly used in normal operation, it may be a power generation unit that uses regenerative energy during operation of the actuator. For example, in the case of the power generation unit that performs electromagnetic induction power generation, it may be used as an electromagnetic induction actuator.

If the left and right power generation apparatuses 720 and 730 generate different power generation amounts while the user is walking or running, the action-inducing information for correcting the unbalance between the left and right feet may be further generated as the third information and presented to the user. The action-inducing information is generated as, for example, visual information such as image and text. Guidance for correcting the unbalance is displayed on the left and right display units 711 and 712. Alternatively, the action-inducing information may be audio information and audio guidance may be provided to instruct the user to correct the manner of walking or running. Note that the image display apparatus 710 can judge that the user is walking or running based on information detected by the acceleration sensor and the GPS sensor, an image captured by the external camera 512, and the like.

For example, the image display apparatus 710 generates, based on the power generation amount obtained from each of the power generation apparatuses 720 and 730, a unique space visually expressing the current posture of the user as the action-inducing information. If the unique space is superimposed on the original image that the user is viewing and displayed, the user can recognize how much degree his/her own posture is deviated, such that the action to correct the posture is induced. The original image means an image of a real space (a landscape of a real world observed in a see-through manner that is displayed to the user in a see-through or video-see-through manner on the head-mounted display or the like), an image of a virtual space of a game or the like, or the like.

Figure 12:
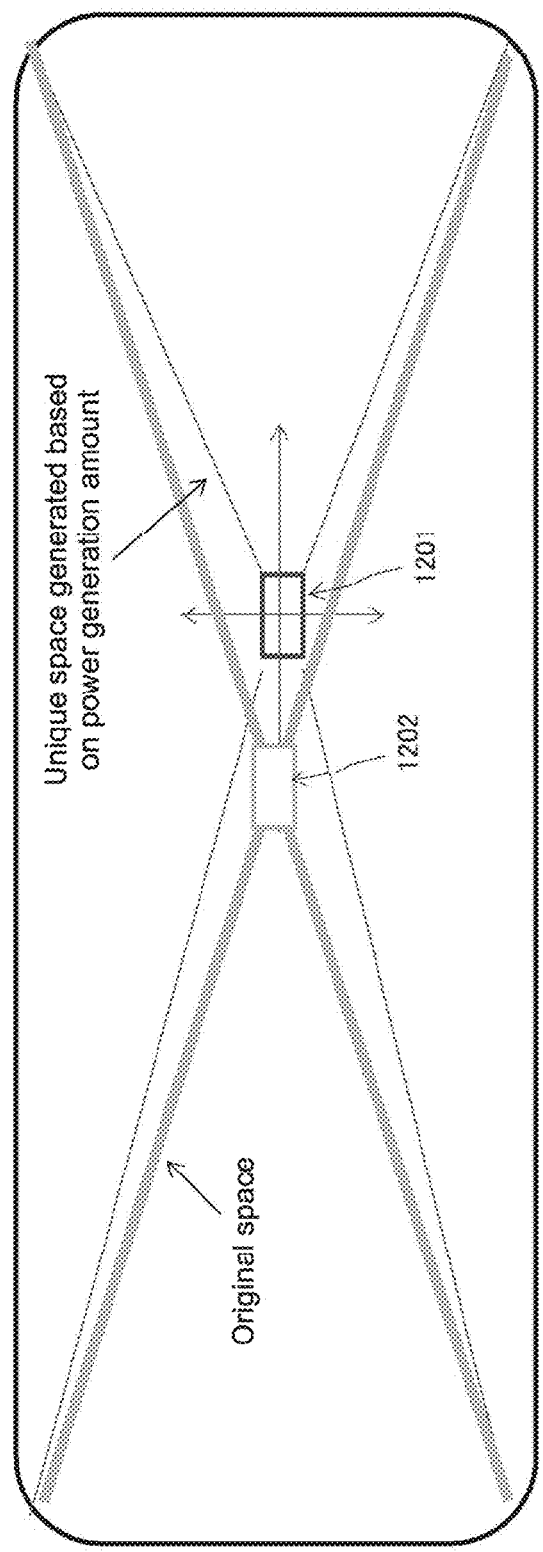
FIG. 12 is a diagram showing a display example in which a unique space generated based on a power generation amount obtained from each of the power generation apparatuses 720 and 730 is combined with an original image.

FIG. 12 shows a display example of the action-inducing information in which a unique space generated based on a power generation amount obtained from each of the power generation apparatuses 720 and 730 is combined with an original image. In the figure, the unique space with the position of the point of origin being deviated depending on the posture unbalance is superimposed on the original image and displayed. The figure shows an indicator 1201 indicating a position of the point of origin of the unique space and an indicator 1202 of a position of a point of origin of the original image. The position 1202 of the point of origin of the unique space is deviated depending on the posture unbalance of the user. Thus, the user can visually understand how much degree his/her own posture is deviated based on a displacement between the indicators 1201 and 1202, such that the action to correct the posture is induced.

Figure 13:
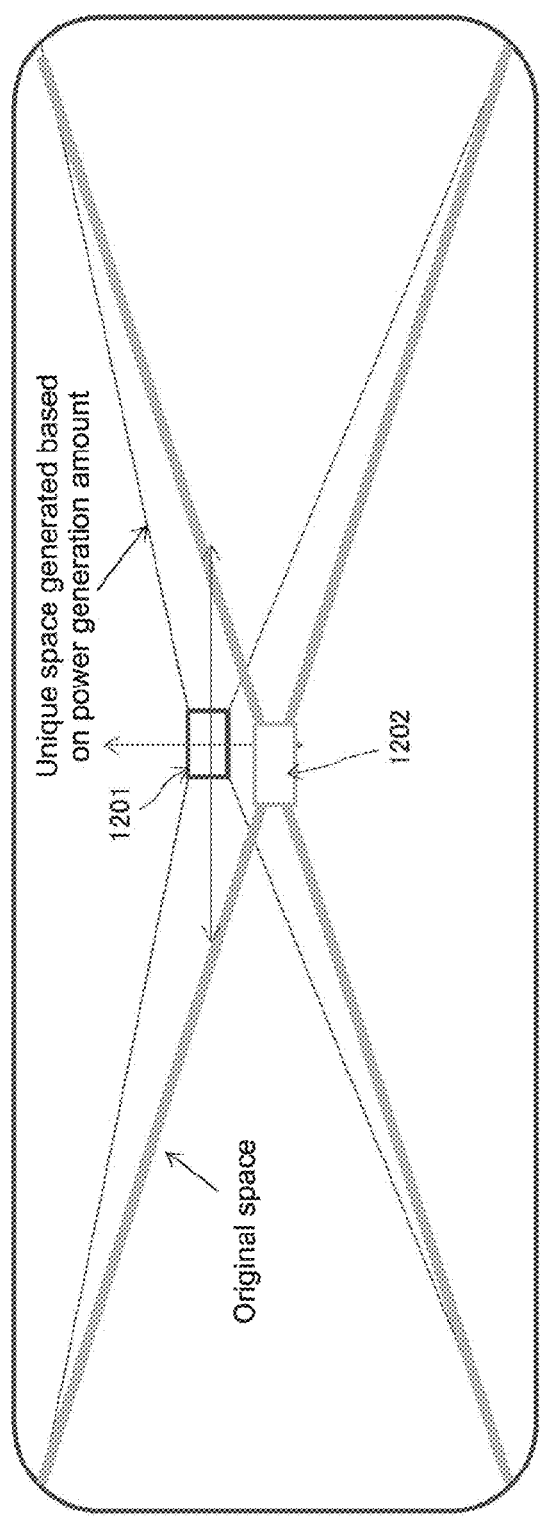
FIG. 13 is a diagram showing a display example (after posture correction) in which a unique space generated based on a power generation amount obtained from each of the power generation apparatuses 720 and 730 is combined with the original image.

By moving the left and right feet such that the indicator 1201 indicating the position of the point of origin of the unique space approaches the position of the point of origin of the original image, the user can correct his/her own posture. Alternatively, instead of displaying the action-inducing information as shown in FIG. 12, the arithmetic unit 633 may generate control information for the actuator (described above) to control the posture balance, based on the amount of displacement between the indicator 1201 indicating the position of the point of origin of the unique space and the position of the point of origin of the original image. The actuator for the posture balance correction is provided in, for example, each of the power generation apparatuses 720 and 730. Otherwise, the power generation unit in each of the power generation apparatuses 720 and 730 also serves as the actuator (described above). The user corrects the posture of the user by moving the left and right feet according to the display of the action-inducing information shown in the figure or transmitting the control information from the image display apparatus 710 to the posture-correcting actuator to control the posture balance. In this manner, as shown in FIG. 13, the indicator 1201 indicating the position of the point of origin of the unique space approaches the position of the point of origin of the original image.

Figure 14:
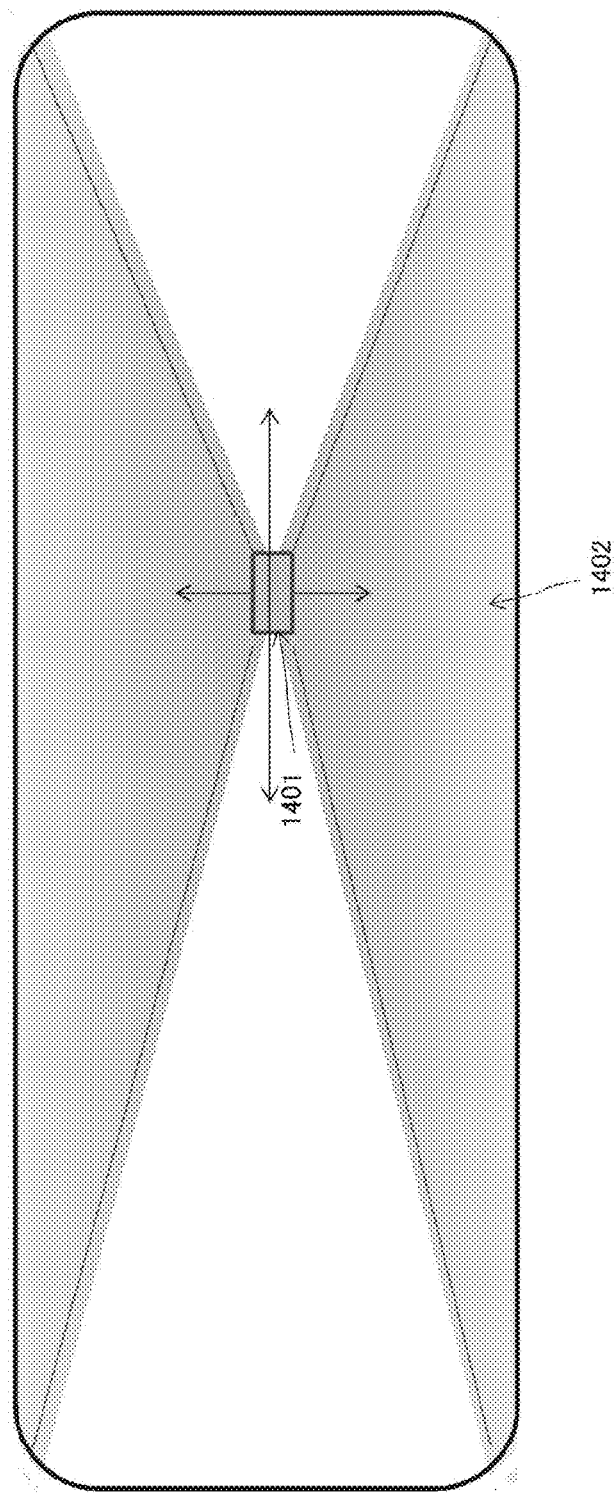
FIG. 14 is a diagram showing another display example in which a unique space generated based on a power generation amount obtained from each of the power generation apparatuses 720 and 730 is combined with an original image.

FIG. 14 shows another display example of the action-inducing information in which the unique space generated based on the power generation amount obtained from each of the power generation apparatuses 720 and 730 is combined with the original image. In the figure, the original image is deformed by combining the unique space having a strain depending on the posture unbalance and the deformed state is expressed by gray shading as indicated by a reference number 1402. An indicator 1401 indicating the position of the point of origin of the unique space is shown. The user can visually understand, based on the displacement of this indicator 1401, how much degree his/her own posture is deviated.

Figure 15:
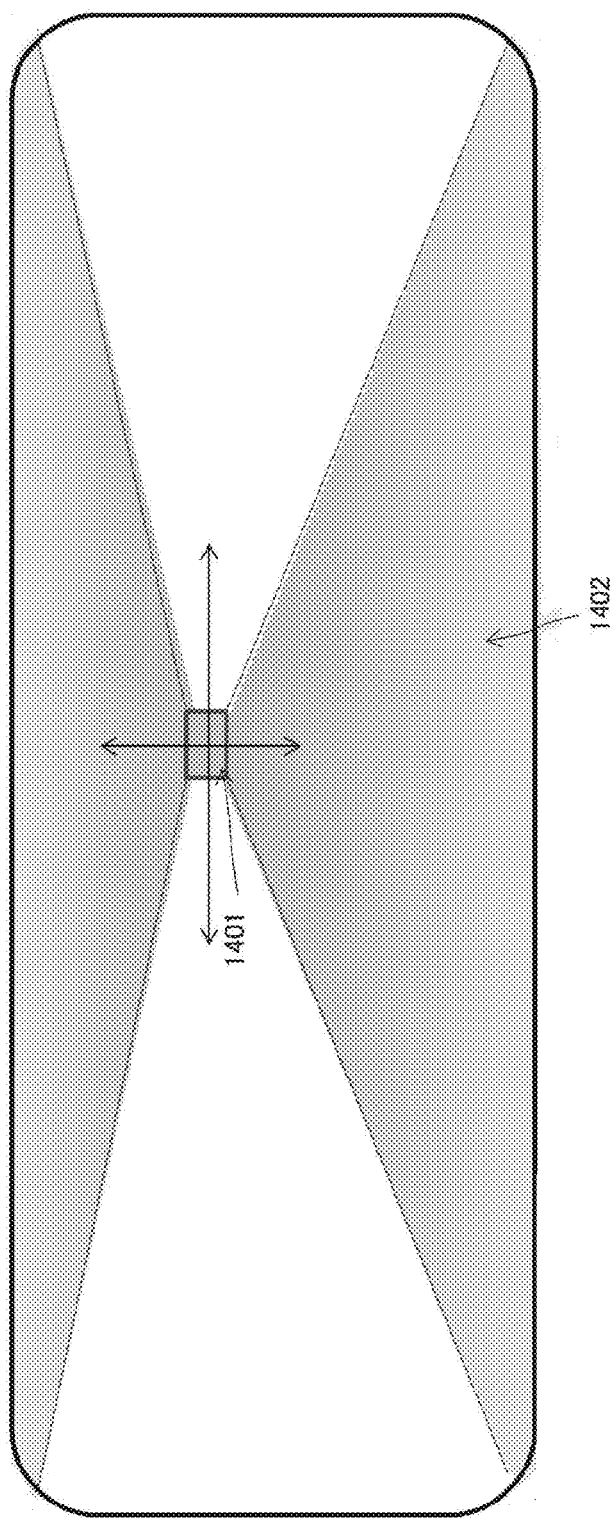
FIG. 15 is a diagram showing another display example (after posture correction) in which a unique space generated based on a power generation amount obtained from each of the power generation apparatuses 720 and 730 is combined with the original image.

According to the display example of the action-inducing information shown in FIG. 14, the space is intentionally deformed and displayed, and hence an illusion is provided to the user and the direction of movement of the user or the balance of weighting of the body is automatically influenced. Thus, a movement of the left and right feet to correct the posture is induced. Moreover, the actuator for the posture balance correction is provided in, for example, each of the power generation apparatuses 720 and 730 or the power generation unit also serves as the actuator (described above). The posture of the user is corrected by the user moving the left and right feet according to the display of the action-inducing information shown in the figure or by transmitting control information depending on the amount of deformation of the space from the image display apparatus 710 to the actuator and performing the posture balance control. In this manner, as shown in FIG. 15, the indicator 1201 indicating the position of the point of origin of the unique space approaches the position of the point of origin of the original image.

Figure 16:
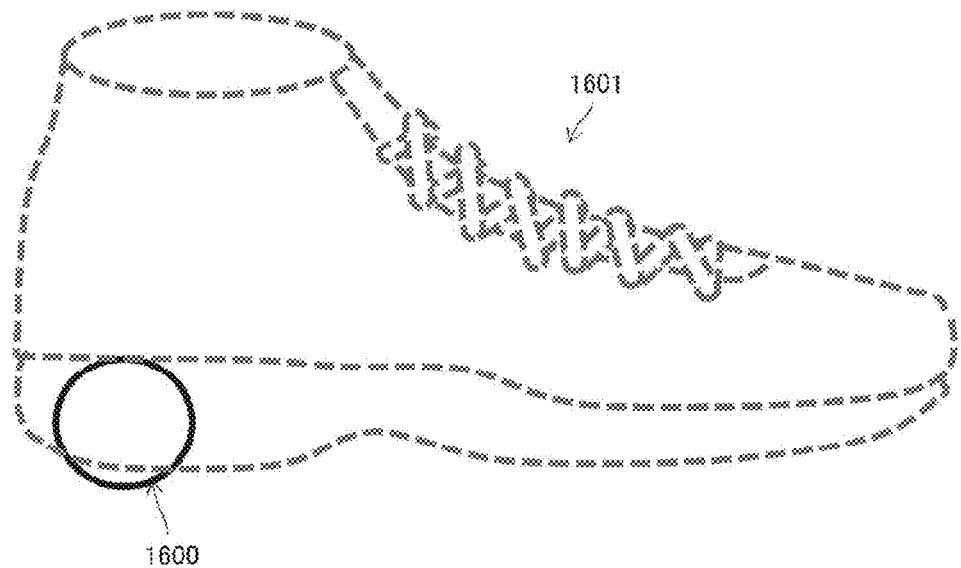
FIG. 16 is a diagram showing a configuration example of a power generation unit of each of the power generation apparatuses 720 and 730 installed in shoes.
Figure 17:
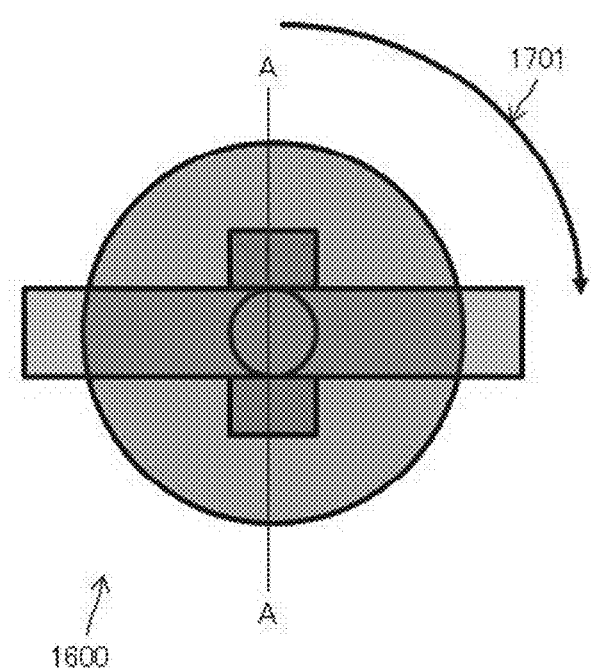
FIG. 17 is a diagram showing a side surface of an electromagnetic induction power generation device 1600 in an enlarged state.
Figure 18:
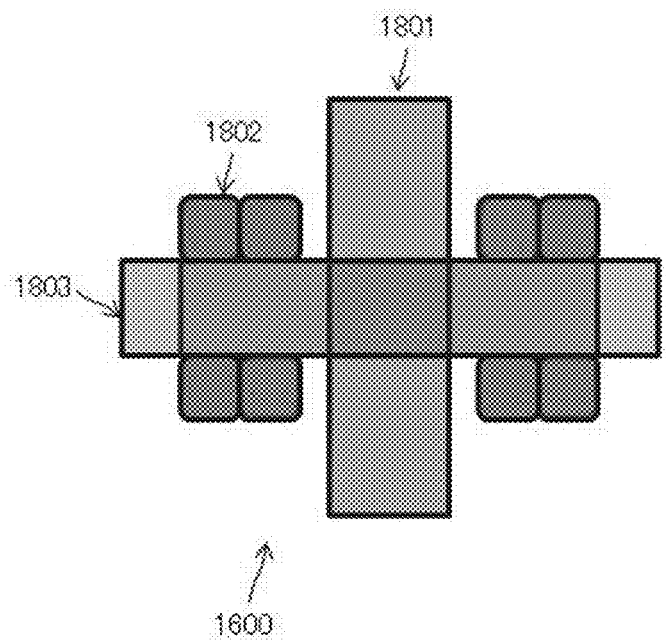
FIG. 18 is a cross-sectional diagram of the electromagnetic induction power generation device 1600.

FIG. 16 shows a configuration example of the power generation unit of each of the power generation apparatuses 720 and 730 installed in the shoes. Each of the power generation apparatuses 720 and 730 includes the power generation unit such as the vibration or motion power generator that generates electrical power using vibrations. In the example shown in the figure, a power generation unit formed of a rotating-type electromagnetic induction power generation device 1600 is installed in a heel sole portion of the shoe 1601. FIG. 17 shows a side surface of the electromagnetic induction power generation device 1600 in an enlarged state. FIG. 18 shows a cross-sectional diagram taken along A-A of the electromagnetic induction power generation device 1600.

The electromagnetic induction power generation device 1600 includes a rotor 1801 that rotates around a roll axis, magnets 1802 that are arranged on both side surfaces of the rotor 1801, and stator coils 1803 that are arranged peripherally outside the magnets 1802 to be opposed to each other. It is assumed that a part of the rotor 1801 is attached to be exposed from the shoe sole. When the user wearing the shoes walks or runs, the shoe soles repeatedly leaves a floor and lands on the floor. The rotor 1801 of the heel sole portion rubs against the floor and is rotated in an arrow direction indicated by a reference number 1701. Magnetic fields of the stator coils 1803 vary every time the magnets 1802 pass by them, and electrical power is generated due to electromagnetic induction action. It is assumed that the power generation amount at this time is proportional to a distance by which the user walked or ran, in other words, the amount of exercise. In addition to this, it is assumed that the power generation efficiency is lowered or changed due to deterioration of the shoe soles and deterioration of the shoes themselves.

Rather than generating electrical power in the above-mentioned manner, the electromagnetic induction power generation device 1600 shown in FIGS. 17 and 18 can rotate the rotor 1801 by being supplied with electrical power (i.e., supplying the stator coils 1803 with an electrical current) and can also operate as the actuator. In short, it can be said that the electromagnetic induction power generation device 1600 takes an electromagnetic induction power generation mode and an electromagnetic induction actuator mode.

Assuming that the power generation amounts of the power generation apparatuses 720 and 730 installed in the left and right shoes are indicated by $P_{left}$ and $P_{right}$, respectively, it can be estimated that if $P_{left} \approx P_{right}$ is established, the posture balance of the user wearing the shoes is in a good state. In view of this, when controlling the posture balance, the good balance can be restored by switching the left and right duties of the electromagnetic induction power generation mode and the electromagnetic induction actuator mode or by changing the left and right loads connected to the electromagnetic induction power generation device 1600 to thereby change left and right rolling coefficients of the shoes such that $P_{left} \approx P_{right}$ is established.

Figure 19:
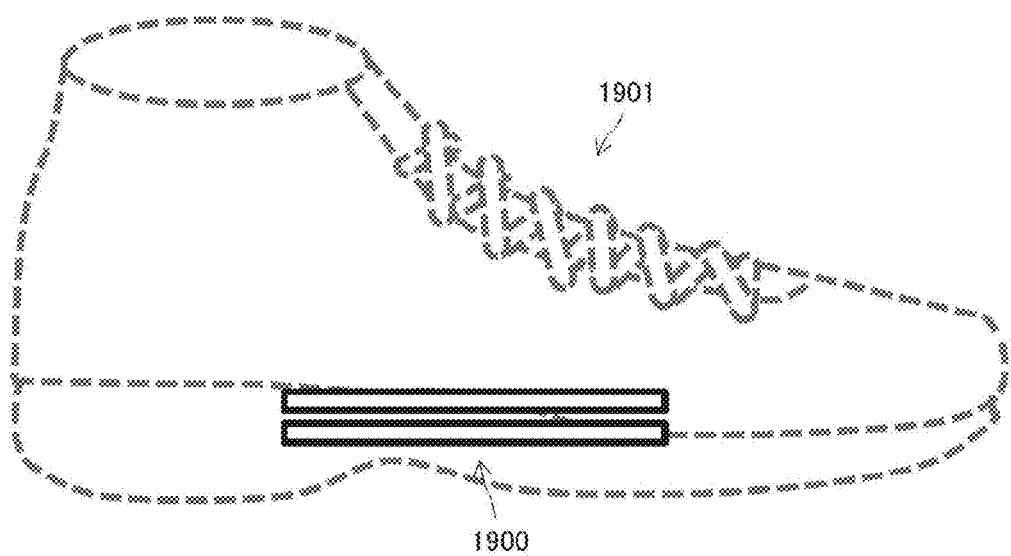
FIG. 19 is a diagram showing another configuration example of the power generation unit of each of the power generation apparatuses 720 and 730 installed in the shoes.
Figure 20:
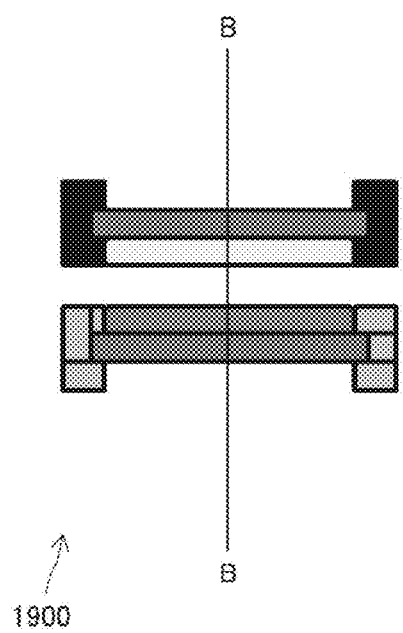
FIG. 20 is a diagram showing a side surface of an electret power generation device 1900 in an enlarged state.
Figure 21:
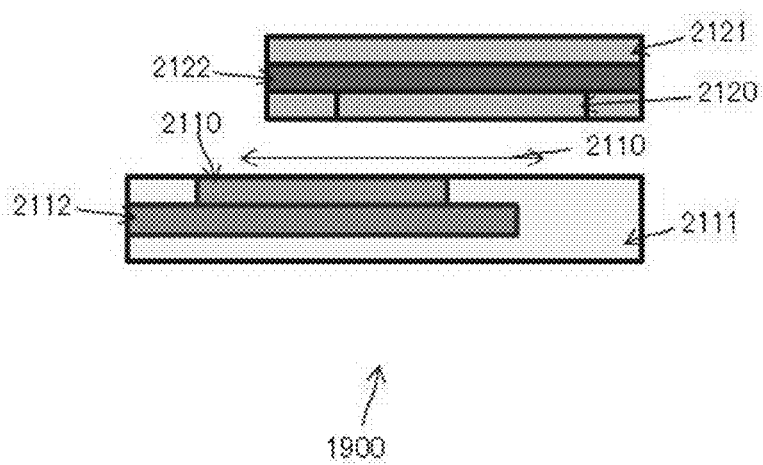
FIG. 21 is a cross-sectional diagram of the electret power generation device 1900.

FIG. 19 shows another configuration example of the power generation unit of each of the power generation apparatuses 720 and 730 installed in the shoes. In the example shown in the figure, a power generation unit that is formed of the electret power generation device 1900 is installed in a sole portion of a shoe 1901. FIG. 20 shows a side surface of the electret power generation device 1900 in an enlarged state. FIG. 21 shows a cross-sectional diagram taken along B-B of the electret power generation device 1900.

The electret power generation device 1900 has a structure in which an electret 2110 and an electrode 2120 are opposed to each other, and generates electrical power using electrostatic induction. The electret 2110 is a matter stably charged by applying a voltage on a ferroelectric insulator to cause electric polarization. The electret 2110 is mounted on a substrate 2112 that slides along a sliding guide 2111. On the other hand, the electrode 2120 is mounted on a substrate 2122 in a fixed position on a fixed guide 2121. When the user wearing the shoes repeatedly steps during walking or running, the position of the electret 2110 is displaced in an arrow direction indicated by a reference number 2101 on the sliding guide 2111. Depending on the displacement of the electret 2110, an area overlapping with the electrode 2120 to which it is opposed is changed, such that electrical charges induced by the electrode 2120 are changed. An amount of change thereof is output as an electrical current, i.e., electrical power. It is assumed that the power generation amount at this time is proportional to a distance by which the user walked or ran, in other words, the amount of exercise. In addition to this, it is assumed that the power generation efficiency is lowered or changed due to deterioration of the shoe soles and deterioration of the shoes themselves.

Rather than generating electrical power in the above-mentioned manner, the electret power generation device 1900 shown in FIGS. 20 and 21 can also displace the position of the electret 2110 in the arrow 2101 direction along the sliding guide 2111 by supplying electrical power (i.e., supplying the electrode 2120 with an electrical current) to thereby cause attraction or repulsion to/from the electret 2110. In short, it can be said that the electret power generation device 1900 takes an electrostatic induction power generation mode and an electrostatic induction actuator mode.

Assuming that the power generation amounts of the power generation apparatuses 720 and 730 installed in the left and right shoes are indicated by $P_{left}$ and $P_{right}$, respectively, it can be estimated that if $P_{left} \approx P_{right}$ is established, the posture balance of the user wearing the shoes is in a good state. In view of this, when controlling the posture balance, the balance can be restored by switching the left and right duties of the electrostatic induction power generation mode and the electrostatic induction actuator mode or by changing the left and right loads connected to the electret power generation device 1900 to thereby change left and right inertias of the shoes such that $P_{left} \approx P_{right}$ is established.

Figure 22:
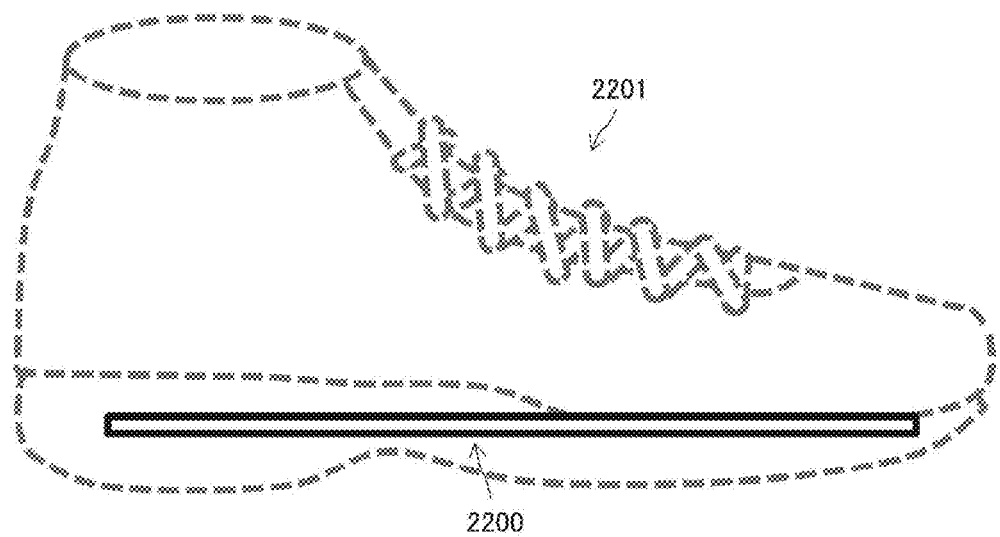
FIG. 22 is a diagram showing still another configuration example of the power generation unit of each of the power generation apparatuses 720 and 730 installed in the shoes.
Figure 23:
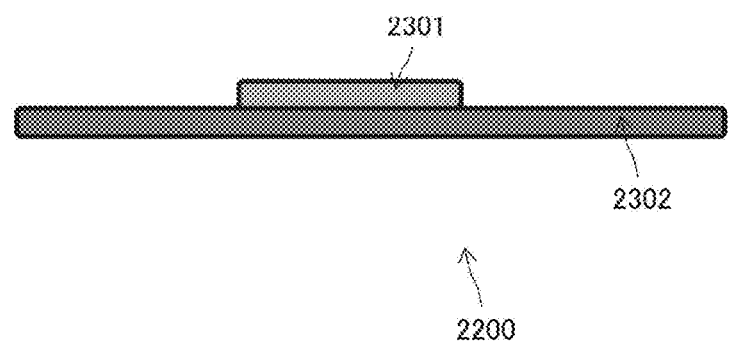
FIG. 23 is a diagram showing a piezoelectric power generation device 2200 in an enlarged state.

FIG. 22 shows still another configuration example of the power generation unit of each of the power generation apparatuses 720 and 730 installed in the shoes. In the example shown in the figure, a power generation unit that is formed of a piezoelectric power generation device 2200 is installed in a sole portion of a shoe 2201. FIG. 23 shows the piezoelectric power generation device 2200 in an enlarged state.

The piezoelectric power generation device 2200 is configured by mounting a piezoelectric element 2301 on a substrate 2302. When the user wearing the shoes repeatedly steps during walking or running, vibrations or strains are added to the piezoelectric element 2301 and the piezoelectric element 2301 transforms them into electrical energy. It is assumed that the power generation amount at this time is proportional to a distance by which the user walked or ran, in other words, the amount of exercise. In addition to this, it is assumed that the power generation efficiency is lowered or changed due to deterioration of the shoe soles and deterioration of the shoes themselves.

The piezoelectric power generation device 2200 shown in FIG. 23 can also cause vibrations or strains to the piezoelectric element 2301 conversely by supplying electrical power (i.e., adding an electrical voltage to the piezoelectric element 2301) rather than generating electrical power in the above-mentioned manner. In short, it can be said that the piezoelectric power generation device 2200 takes a piezoelectric power generation mode and a piezoelectric actuator mode.

Assuming that the power generation amounts of the power generation apparatuses 720 and 730 installed in the left and right shoes are indicated by $P_{left}$ and $P_{right}$, respectively, it can be estimated that if $P_{left} \approx P_{right}$ is established, the posture balance of the user wearing the shoes is in a good state. In view of this, when controlling the posture balance, the balance can be restored by switching the left and right duties of the piezoelectric power generation mode and the piezoelectric actuator mode or by changing the left and right loads connected to the piezoelectric power generation device 2200 to thereby change the rigidity of the left and right shoes such that $P_{left} \approx P_{right}$ is established.

Figure 24:
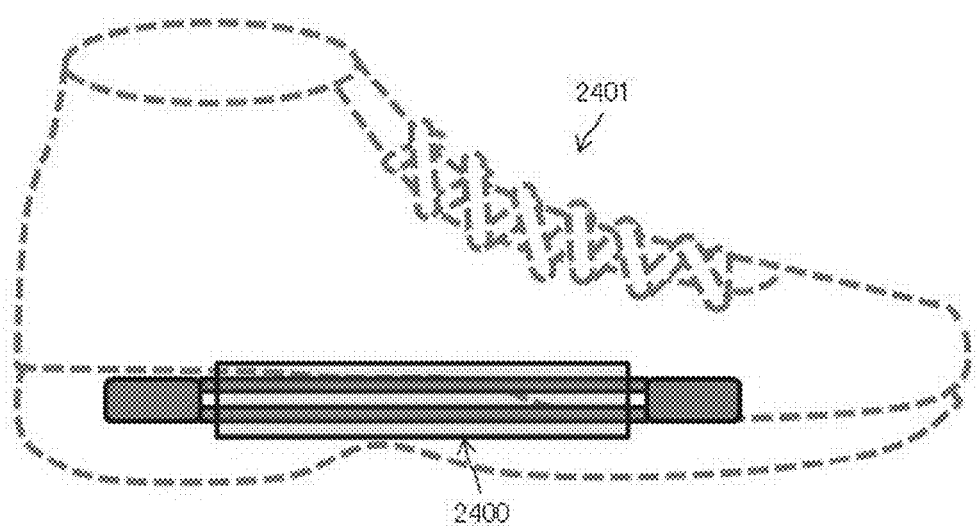
FIG. 24 is a diagram showing still another configuration example of the power generation unit of each of the power generation apparatuses 720 and 730 installed in the shoes.
Figure 25:
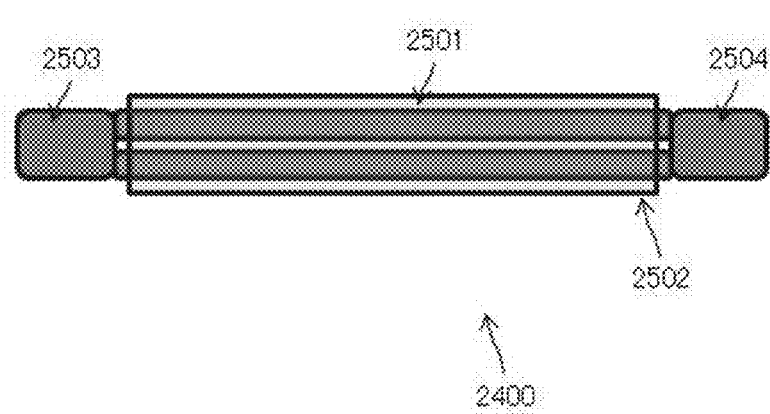
FIG. 25 is a diagram showing an inverse-magnetostrictive power generation device 2400 in an enlarged state.

FIG. 24 shows still another configuration example of the power generation unit of each of the power generation apparatuses 720 and 730 installed in the shoes. In the example shown in the figure, the power generation unit that is formed of an inverse-magnetostrictive power generation device 2400 is installed in a sole portion of a shoe 2401. FIG. 25 shows the inverse-magnetostrictive power generation device 2400 in an enlarged state.

The inverse-magnetostrictive power generation device 2400 includes a magnetostrictive element 2501, a coil 2502 that is wound covering an outer periphery of the magnetostrictive element 2501, and fixed ends 2503 and 2504 that support both ends of the magnetostrictive element 2501 in the sole portion of the shoe 2401. When the user wearing the shoes repeatedly steps during walking or running, a stress is added to the magnetostrictive element 2501. Due to the application of the stress on the magnetostrictive element 2501, an inverse-magnetostrictive effect that the magnetic susceptibility changes is exerted, such that the coil 2502 is supplied with an induced current that overcomes the change of the magnetic field. As a result, electrical power can be obtained. It is assumed that the power generation amount at this time is proportional to a distance by which the user walked or ran, in other words, the amount of exercise. In addition to this, it is assumed that the power generation efficiency is lowered or changed due to deterioration of the shoe soles and deterioration of the shoes themselves.

The inverse-magnetostrictive power generation device 2400 shown in FIG. 25 can also cause a strain in the magnetostrictive element 2501 conversely by supplying electrical power (i.e., supplying the coil 2502 with an electrical current) rather than generating electrical power in the above-mentioned manner. In short, it can be said that the inverse-magnetostrictive power generation device 2400 takes an inverse-magnetostrictive power generation mode and a magnetostrictive actuator mode.

Assuming that the power generation amounts of the power generation apparatuses 720 and 730 installed in the left and right shoes are indicated by $P_{left}$ and $P_{right}$, respectively, it can be estimated that if $P_{left} \approx P_{right}$ is established, the posture balance of the user wearing the shoes is in a good state. In view of this, when controlling the posture balance, the balance can be restored by switching the left and right duties of the inverse-magnetostrictive power generation mode and the magnetostrictive actuator mode or by changing the left and right loads connected to the inverse-magnetostrictive power generation device 2400 to thereby change the rigidity of the left and right shoes such that $P_{left} \approx P_{right}$ is established.

The configurations of "shoe power generation" in which the power generation apparatuses are installed in the shoes worn by the user have been shown above. However, even if the power generation apparatuses are mounted on various objects that the user wears, for example, an accessory such as ring, wristwatch, bracelet, anklet, and necklace that the user wears, clothes that the user wears, pants that the user wears, or a bag that the user carries (e.g., see Patent Document 4), it is possible to achieve monitoring and posture balance control similar to those described above.

Further, by conversely supplying the power generation apparatus mounted on the clothes, pants, or the like with electrical power, it can also be operated as the actuator. It is also possible to switch the loads connected to the power generation apparatus or operate the power generation apparatus as the actuator to change the rigidity of the clothes worn by the user in each location, to thereby perform the posture balance control.

In addition, other than the vibration or motion power generator that generates electrical power using vibrations caused when the user performs the exercise, the power generation apparatus installed in clothes, hat, or the like can obtain electrical power using a power generation unit formed of any one or a combination of two or more of a thermoelectric conversion element that generates electrical power using a temperature difference between a body temperature of the user and a reference temperature such as an outside air temperature, an enzymatic cell that generates electrical power using sweat of the user, a solar-cell power generation element that generates electrical power using sunlight with which the user is irradiated when the user is outside the home or illumination light in a room, an ultraviolet-ray power generation element that generates electrical power using ultraviolet rays, an infrared-ray power generation element that generates electrical power using infrared rays, a radio-wave power generation element that induces electrical power using environmental electromagnetic waves from a neighboring wireless access point or the like, a power generation element that generates electrical power using radial rays with which the user is irradiated, and a sound-pressure power generation element that induces electrical power using a sound pressure or the like.

Example 2

A monitoring system according to Example 2 positively uses information from the power generation apparatus mainly installed in a matter other than the user and monitors a state of the matter in which the power generation apparatus is installed. If the matter in which the power generation apparatus is installed is in an interlocking or restraining relationship with the body of the user, the state of the matter and the state of the user can be both monitored.

Figure 26:
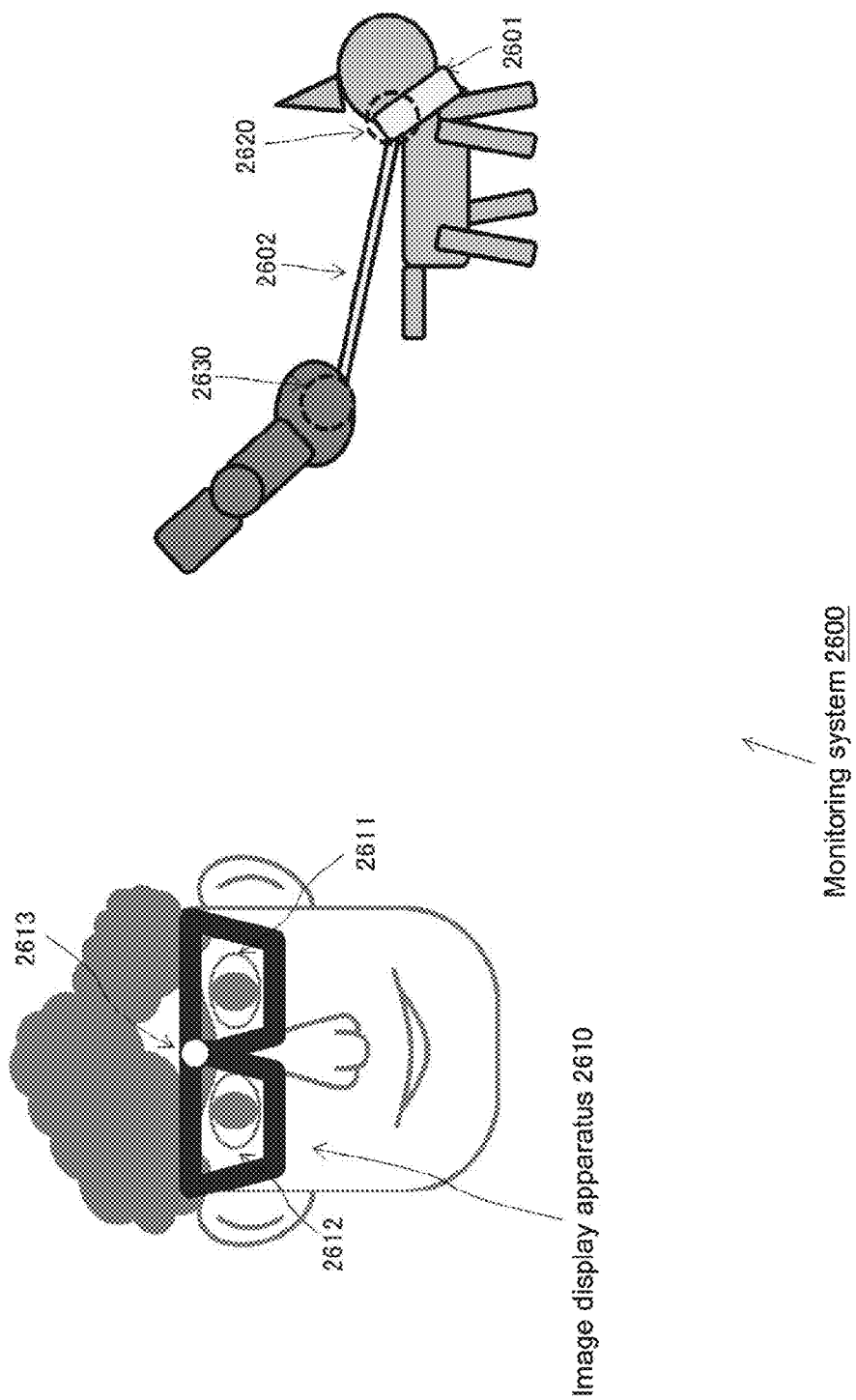
FIG. 26 is a diagram schematically showing a configuration of a monitoring system 2600 according to Example 2.

FIG. 26 schematically shows a configuration of a monitoring system 2600 according to Example 2. The monitoring system 2600 shown in the figure is formed of an image display apparatus (head-mounted display) 2610 that is used by being mounted on the head or face of the user, a power generation apparatus 2620 installed on a collar 2601 of a companion animal, and a power generation apparatus 2630 installed on a lead 2602 with which the user pulls the companion animal. For the sake of description, only one power generation apparatus 2620 or 2630 is illustrated for each of the collar 2601 and the lead 2602. However, an example in which two or more power generation apparatuses are installed on each of the collar 2601 and the lead 2602 is also conceivable. The monitoring system 2600 basically has the functional configuration shown in FIG. 6. However, in FIG. 26, the system 600 is shown in an abstract manner as it is operated.

The image display apparatus 2610 includes two display units 2611 and 2612 that present the left eye image and the right eye image to the left and right eyes of the user, respectively, and an acceleration sensor 2613 that measures an acceleration acting on the head of the user.

The power generation apparatus 2620 attached to the collar 2601 of the companion animal includes a power generation unit, a storage element, and a communication unit (not shown). The power generation unit is formed of, for example, the thermoelectric conversion element. The power generation unit generates electrical power using a temperature difference between a body temperature of the companion animal and the outside air temperature and stores the obtained electrical power in the storage element such as a secondary battery. Alternatively, the power generation unit may be an electromagnetic induction power generation device that generates electrical power using mechanical vibrations or may be an enzymatic cell that generates electrical power using sweat of the companion animal. It is assumed that, with any power generation element, the power generation unit can obtain a power generation amount depending on an amount of exercise of the companion animal. The communication unit uses, for example, wireless communication such as Wi-Fi to exchange data with the image display apparatus 2610. The communication unit may be constantly operated and transfer the first information such as the power generation amount and the power storage amount in real time or may be intermittently operated and transfer the first information. Alternatively, the communication unit may directly exchange data with the power generation apparatus 2630 installed on the lead 2602 through a signal line inserted in the lead 2602 or an electroconductive fiber (not shown) laid on a surface of the lead 2602.

Moreover, the power generation apparatus 2630 attached to the lead 2602 of the companion animal includes a power generation unit, a storage element, and a communication unit (not shown). The power generation unit is formed of, for example, the electromagnetic induction power generation device that generates electrical power using mechanical vibrations and stores the obtained electrical power in the storage element such as a secondary battery. The communication unit can use, for example, wireless communication such as Wi-Fi. Alternatively, the communication unit may directly exchange data with the power generation apparatus 2620 installed on the collar 901 through a signal line inserted in the lead 2602 or an electroconductive fiber (not shown) laid on a surface of the lead 2602.

The image display apparatus 2610 displays the first information such as the power generation amounts received from the power generation apparatuses 2620 and 2630 and the second information obtained by processing the power storage amounts on the left and right display units 2611 and 2612.

For example, the image display apparatus 2610 converts the first information such as the power generation amount of each of the power generation apparatuses 2620 and 2630 into an acceleration and a metabolic rate (calorie consumption) as the second information. Based on this second information and a value detected by the acceleration sensor 2613 provided in the image display apparatus 2610, it is possible to perform acceleration measurement at two points of a hand of the user that holds the lead 2602 and the lead 2602 or the collar 2601 of the companion animal and perform measurement of the amount of exercise at either one point. Due to the acceleration measurement at the two points, it is possible to know a correlation between a pulling degree of the user and the amount of exercise of the companion animal and convert it into metabolic rates (calorie consumption) of the user and the companion animal. Based on these data pieces, it is possible to calculate a correlation between the metabolic rate (calorie consumption) of the user and the metabolic rate (calorie consumption) of the companion animal in real time.

Figure 27:
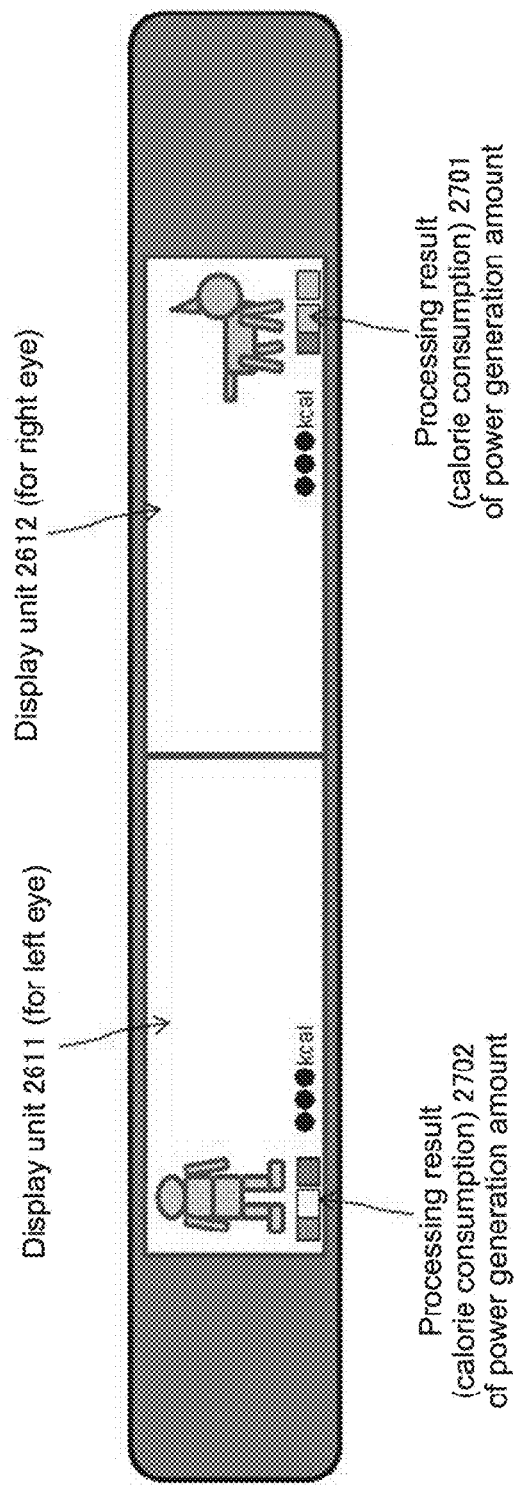
FIG. 27 is a diagram showing a display example in Example 2.

For example, as shown in FIG. 27, second information 2701 such as the metabolic rate (calorie consumption) obtained by converting the first information from the power generation apparatus 2620 installed on the collar 2601 of the companion animal may be displayed on the display unit 2612 for the right eye and second information 2702 such as the metabolic rate (calorie consumption) obtained by converting the first information from the power generation apparatus 2630 installed on the lead 2602 may be displayed on the display unit 2611 for the left eye. FIG. 27 respectively shows the metabolic rate (calorie consumption) of the companion animal and the metabolic rate (calorie consumption) of the user as the second information 2701 and 2702 obtained by processing the first information such as the power generation amount and the power storage amount.

In addition, based on the calorie consumption of the exercise of the companion animal according to the basal metabolism, which serves as the second information, the image display apparatus 2610 can derive an adequate amount of feed supplied to the companion animal as the third information and manages the health of the companion animal. When converting the first information such as the power generation amount of the power generation apparatus 2620 into the second information such as the amount of exercise and the metabolic rate (calorie consumption) of the companion animal, the arithmetic unit 633 may further derive, from the second information, control information for controlling an automatic feeder (not shown) for the companion animal as the third information.

According to the monitoring system 2600 of this example, the second information that is out of a perception range for the user wearing the image display apparatus 100 or difficult to perceive can be presented to the user based on the first information such as the power generation amount that is obtained on the side of each of the power generation apparatuses 2620 and 2630 and the second information converted from the first information. On the side of the image display apparatus 2610, the perception range of the user can be extended by arranging and presenting information pieces obtained from the power generation apparatuses 2620 and 2630.

Note that a method of additionally providing each of the power generation apparatuses 2620 and 2630 with the acceleration sensor in order to monitor the amount of exercise or the like of the companion animal is also conceivable. However, with such sensors, the component cost of the power generation apparatuses 2620 and 2630 increases and power consumption of the entire power generation apparatuses 2620 and 2630 also increases. As a result, the continuous use time is inevitably shortened. In contrast, as in this example, according to the method of transmitting the first information such as the power generation amount from the power generation apparatuses 2620 and 2630 and converting the first information received on the side of the image display apparatus 2610 into the second information such as the amount of exercise of the user or companion animal, the apparatus cost can be reduced. In addition, the power generation unit itself serves as the sensing device and a power-supply does not have to be provided. Therefore, the power consumption of the entire system 2600 is reduced. The limitation on the continuous use time is overcome and the power generation apparatuses 2620 and 2630 do not have to be increased in size for the batteries.

Example 3

A monitoring system according to Example 3 positively uses information from a plurality of power generation apparatuses mainly installed in matters other than the user and monitors an environment in the location where each of the power generation apparatuses is installed. For example, if a plurality of power generation apparatuses are installed in such a range that it can directly communicate with the image display apparatus worn by the user, a surrounding environment and a change thereof can be monitored by adding up information pieces collected from the power generation apparatuses.

Figure 28:
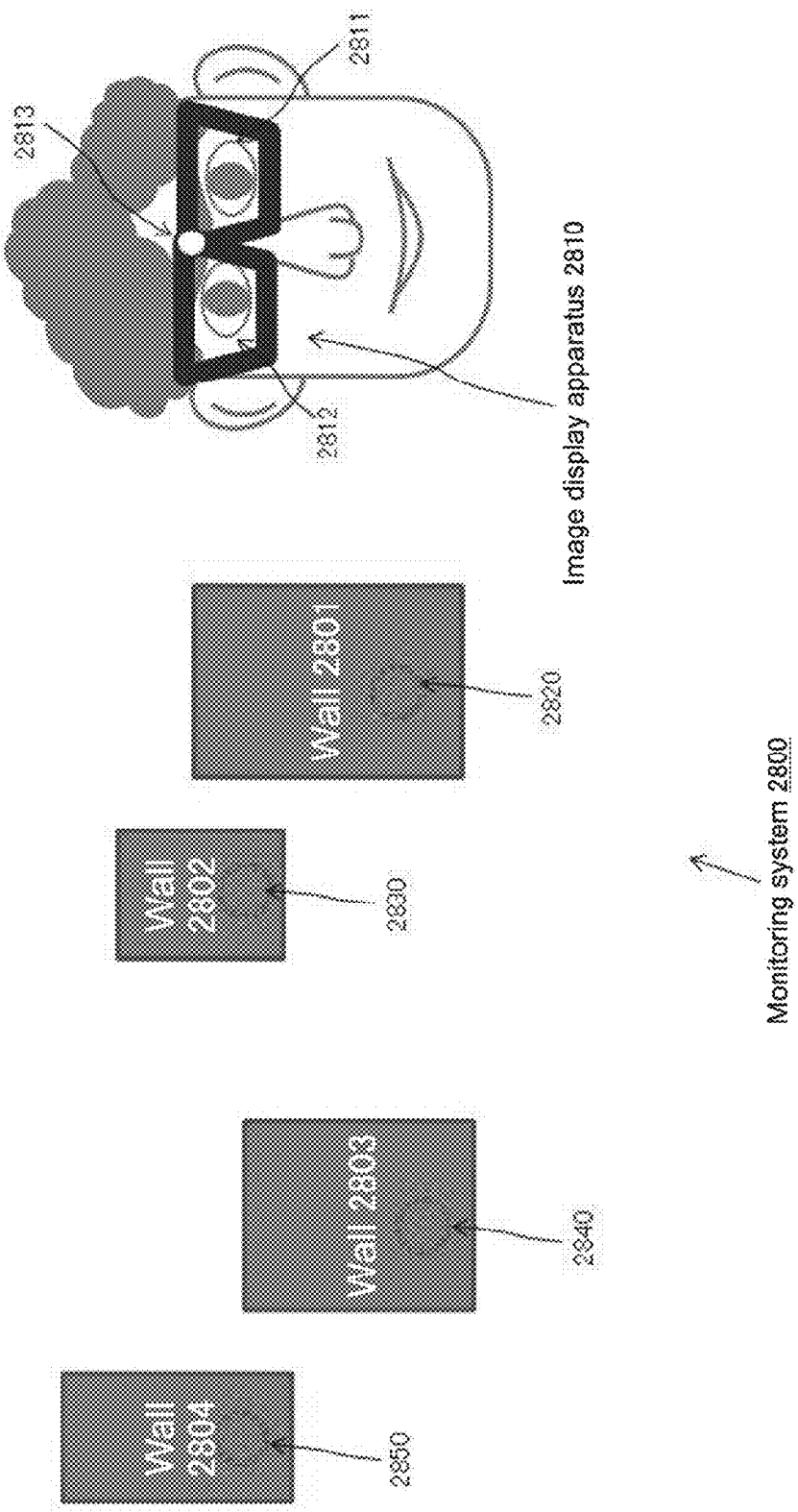
FIG. 28 is a diagram schematically showing a configuration of a monitoring system 2800 according to Example 3.

FIG. 28 schematically shows a configuration of a monitoring system 2800 according to Example 3. The monitoring system 2800 shown in the figure is formed of an image display apparatus (head-mounted display) 2810 that is used by being mounted on the head or face of the user and a plurality of power generation apparatuses that are installed in the surrounding environment of the user. In the example shown in the figure, power generation apparatuses 2820, 2830, 2840, and 2850 are respectively installed on walls 2801, 2802, 2803, and 2804 of a room in which the user is located. As a matter of course, it is also conceivable that five or more or three or less power generation apparatuses are installed in the surrounding environment of the user. The monitoring system 2800 basically has the functional configuration shown in FIG. 6. However, in FIG. 28, the system 2800 is shown in an abstract manner as it is operated.

The image display apparatus 2810 includes two display units 2811 and 2812 that present the left eye image and the right eye image to the left and right eyes of the user, respectively, and an environmental sensor 2813 that measures environmental energy such as electromagnetic waves with which the user is irradiated.

Each of the power generation apparatuses 2820 to 2850 includes a power generation unit, a storage element, and a communication unit (not shown). The power generation unit generates electrical power using environmental energy and stores the obtained electrical power in the storage element such as a secondary battery. Examples of the energy source in the energy harvesting can include environmental electromagnetic waves. For example, a radio-wave power generation apparatus that generates electrical power using electromagnetic waves having a particular frequency can be used as the power generation unit. Alternatively, a solar-cell power generation element, an ultraviolet-ray power generation element, an infrared-ray power generation element, a power generation element that generates electrical power using radial rays, or the like, or another power generation element that induces electrical power using environmental energy, or a combination of two or more of them may be used as the power generation unit.

The communication unit uses, for example, wireless communication such as Wi-Fi to exchange data with the image display apparatus 2810. The communication unit may be constantly operated and transfer the first information such as the power generation amount of the power generation unit in real time or may be intermittently operated and transfer the first information. Alternatively, the communication unit may communicate and directly exchange the data with other power generation apparatuses.

Figure 29:
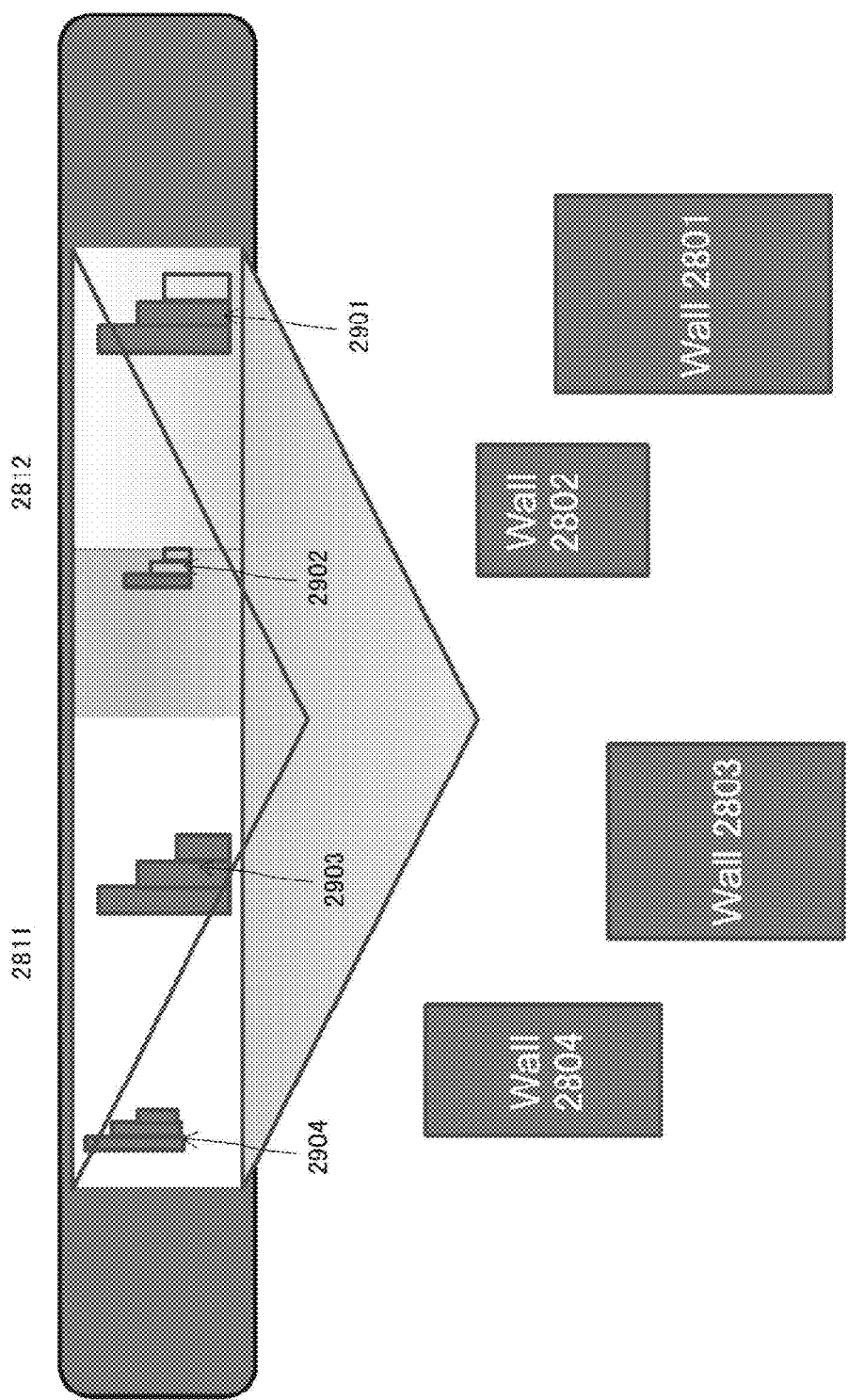
FIG. 29 is a diagram showing a display example in Example 3.

The image display apparatus 2810 displays the first information such as the power generation amount received from each of the power generation apparatuses 2820 to 2850 to the left and right display units 2811 and 2812. For example, the image display apparatus 2810 displays the power generation amounts of the power generation apparatuses 2820 to 2850 on the left and right display units 2811 and 2812. If the image display apparatus 2810 is a see-through type head-mounted display, as shown in FIG. 29, icons 2901 to 2904 respectively indicating the power generation amounts of the power generation apparatuses 2820 to 2850 are subjected to space mapping and displayed superimposed on the locations of the walls 2801 to 2804 where they are installed. Thus, distribution of charged secondary batteries in the real world can be visualized. Through the displayed image as shown in FIG. 29, the user can know at a glance where the sufficiently charged secondary battery is or with which of the batteries the user should perform replacement. If five or more power generation apparatuses are installed in the surrounding environment of the user or if the installation locations of the power generation apparatuses are changed, the positions in which the icons indicating the power generation amounts are displayed are correspondingly changed.

Through the displayed image as shown in FIG. 29, the user can understand that environmental energy virtually exists in the locations in which the icons 2901 to 2904 are displayed. For example, the user can know where the sufficiently charged secondary battery is and can also know whether or not environmental energy (electromagnetic waves having a particular frequency, ultraviolet rays, radial rays, or the like) in the location is strong.

It is assumed that the power generation amount of each of the power generation apparatuses 2820 to 2850 is proportional to the intensity of environmental energy such as electromagnetic waves, ultraviolet rays, and radioactivity with which each location is irradiated. In view of this, in the image display apparatus 2810, the arithmetic unit 633 may convert the first information such as the power generation amounts received from the power generation apparatuses 2820 to 2850 into environmental-energy intensity of electromagnetic waves, ultraviolet rays, radioactivity, or the like with which the power generation apparatuses 2820 to 2850 are irradiated and display it on the left and right display units 2811 and 2812. For example, if the image display apparatus 2810 is a see-through type head-mounted display, the environmental-energy intensity calculated as the second information with respect to each of the power generation apparatuses 2820 to 2850 and the environmental-energy intensity detected by the environmental sensor 2813 of the image display apparatus 2810 are subjected to space mapping and displayed superimposed in the locations of the walls 2801 to 2804 where they are installed. Thus, distribution of environmental-energy intensity in the real world can be visualized.

Note that a method of additionally providing each of the power generation apparatuses 2820 to 2850 with an environmental sensor that measures the electromagnetic-wave intensity or the like in order to monitor environmental factors such as the environmental-energy intensity in each of the locations 2801 to 2804 is also conceivable. However, with such sensors, the component cost of the power generation apparatuses 2820 to 2850 increases and the power consumption of the power generation apparatuses 2820 to 2850 also increases. As a result, the continuous use time is inevitably shortened. In contrast, as in this example, according to the method of transmitting the first information such as the power generation amount from each of the power generation apparatuses 2820 to 2850 and converting the power generation amount into the second information such as the intensity of the environmental-energy such as the electromagnetic waves, the ultraviolet rays, and the radioactivity on the side of the image display apparatus 2810, the apparatus cost of the power generation apparatuses 2820 to 2850 can be reduced. In addition, the power generation unit itself serves as the sensing device and a power-supply does not have to be provided. Therefore, the power consumption of each of the power generation apparatuses 2820 to 2850 is reduced. The limitation on the continuous use time is overcome and the power generation apparatuses 2820 to 2850 do not have to be increased in size for the batteries.

FIGS. 28 and 29 show the example in which the power generation apparatus is installed in the room. However, as a matter of course, it is also conceivable that it is installed in an outside street corner, a rooftop of a building, or the like. If each power generation apparatus transmits the power generation amount obtained by receiving mobile waves or radio waves of Wi-Fi or the like as the first information, the image display apparatus 2810 can convert the first information such as the power generation amounts of the power generation apparatuses into the second information such as the antenna strength in their installation locations and display the result on the left and right display units 2811 and 2812.

Figure 30:
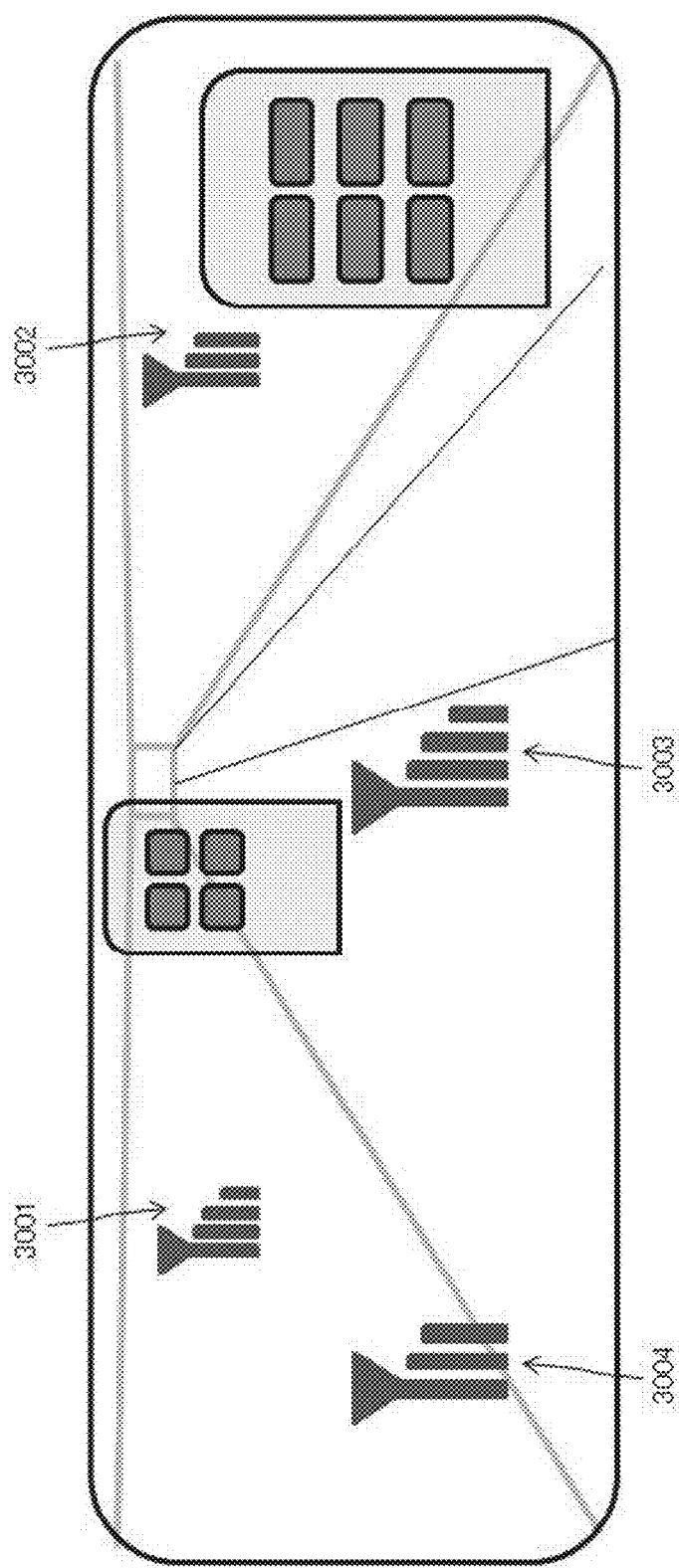
FIG. 30 is a diagram showing another display example in Example 3.

FIG. 30 shows an example in which antenna strength 3001, 3002, . . . in each location of the surrounding environment of the user, which is obtained based on power generation amounts of the surrounding power generation apparatuses 2820 to 2850, is visualized by the image display apparatus 2810. By viewing the image as shown in FIG. 30, the user can know at a glance where the sufficiently charged secondary battery is and can also know where the user should go for obtaining the strong mobile waves or radio waves of the Wi-Fi, where it is easier to phone and connect with a wireless access point. In addition, without searching for the installation location of the antenna, the user can know at a glance where the user should go for improving the electromagnetic environment.

The image display apparatus 2810 can reflect the result of conversion into the antenna strength as shown in FIG. 30 in control of the image display apparatus 2810 itself or the external device. For example, control information for a radio-wave re-transmitter can be derived from the second information such as the antenna strength.

After presenting the displayed image as shown in FIG. 30 to the user, the image display apparatus 2810 can upload it into the server on the Internet (not shown) (including posting to an information providing site) or transmit it to information terminals of other users through direct communication such that the information on the antenna strength can be shared between the users. For example, as a report to a communication enterprise that provides a line network, the image display apparatus 2810 may automatically transmit the displayed image as shown in FIG. 30 or the user may manually transmit the displayed image as shown in FIG. 30.

Additionally, the power generation apparatus installed outside such as the street corner and the rooftop can also generate electrical power by receiving hazardous electromagnetic waves (ultraviolet rays) or radial rays. In this case, in the image display apparatus 2810, the arithmetic unit 633 converts the first information such as the power generation amounts of the power generation apparatuses 2820 to 2850 into the second information such as the intensity of hazardous electromagnetic waves or radial rays (or an index value indicating a degree of harm) and display the result on the left and right display units 2811 and 2812.

Figure 31:
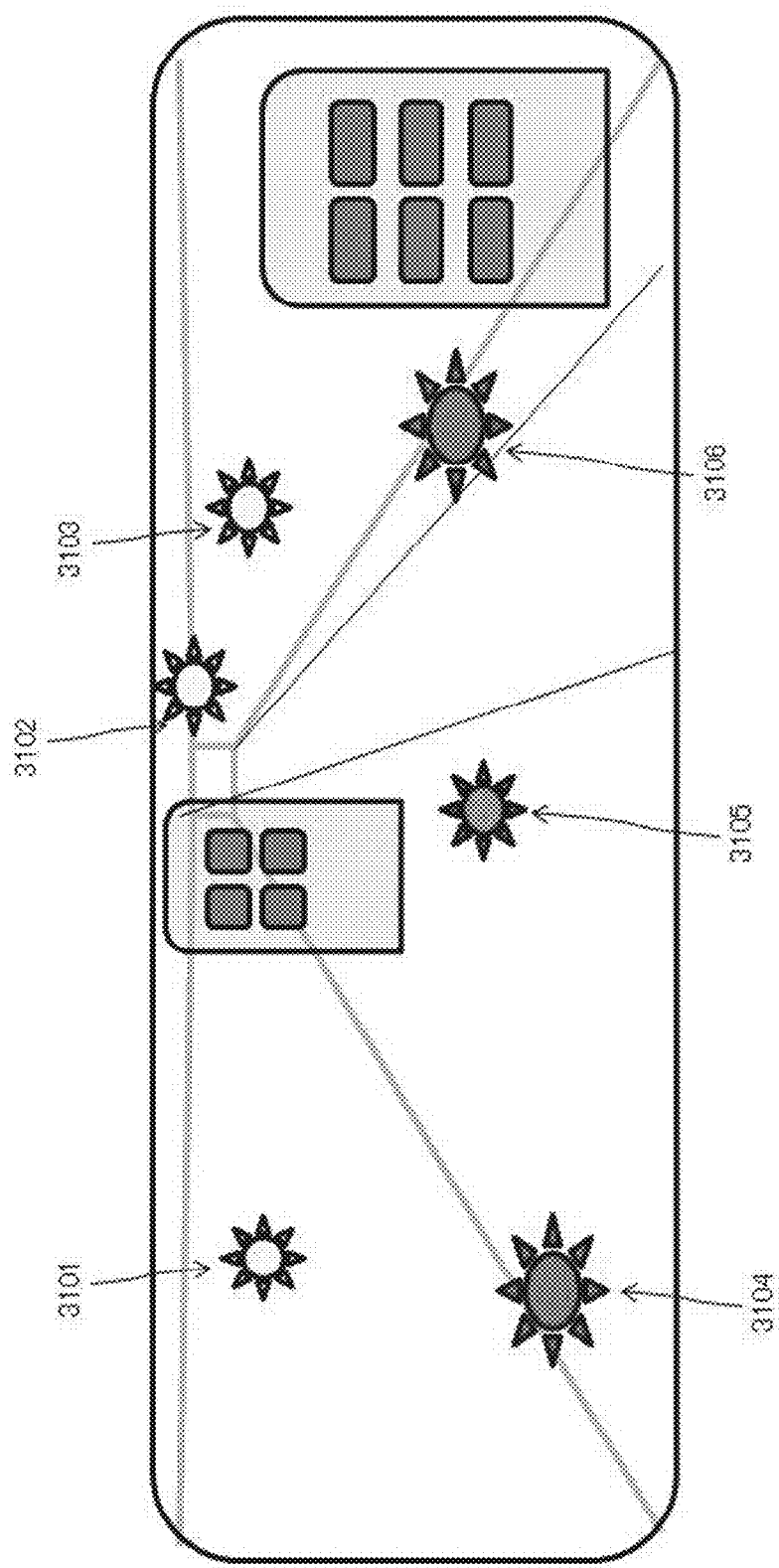
FIG. 31 is a diagram showing still another display example in Example 3.

FIG. 31 shows an example in which the intensity of hazardous electromagnetic waves (ultraviolet rays) or radial rays in each location of the surrounding environment of the user, which is obtained converting the power generation amount obtained from the surrounding power generation apparatuses 2820 to 2850, is visualized by the image display apparatus 2810. In the example shown in the figure, the icons 3101, 3102, . . . each expressing, with the color or size, the intensity of hazardous electromagnetic waves (ultraviolet rays) or radial rays obtained by converting the power generation amount of each of the power generation apparatuses 2820 to 2850 are arranged in the corresponding locations. By viewing the image shown in FIG. 31, the user can know at a glance where the intensity of hazardous electromagnetic waves (ultraviolet rays) or radial rays is higher and where the user should go for reducing the influence thereof or where the user should go for avoiding the influence thereof.

The image display apparatus 2810 can derive, from the result of conversion into the intensity of hazardous electromagnetic waves (ultraviolet rays) or radial rays as shown in FIG. 31, control information for controlling the image display apparatus 2810 itself or the external device (e.g., an operation of a sunshade of an arcade or a light-shielding facility of a building or house).

After presenting the displayed image as shown in FIG. 31 to the user, the image display apparatus 2810 can upload it into the server on the Internet (not shown) (including posting to an information providing site) or transmit it to information terminals of other users through direct communication such that the information on hazardous electromagnetic waves (ultraviolet rays) or radial rays can be shared between the users. For example, UV index forecast, correction of the forecast, or improvement of position resolution can be performed by adding up information pieces transmitted from a plurality of users in the server.

If the image visualizing a result of the image display apparatus 2810 adding up the first information such as the power generation amounts of the surrounding power generation apparatuses 2820 to 2850, for example, the distribution of the batteries shown in FIG. 29, the distribution of the antenna strength shown in FIG. 30, or the distribution of the intensity of hazardous electromagnetic waves (ultraviolet rays) or radial rays shown in FIG. 31, is displayed also on the external display unit 515, the radio wave condition of the environment can be presented also to people around the user.

According to the monitoring system 2800 of this example, the second information such as the distribution of the batteries, the distribution of the antenna strength, or the distribution of the intensity of hazardous electromagnetic waves (ultraviolet rays) or radioactivity, which is out of a perception range for the user wearing the image display apparatus 2810 or difficult to perceive, can be converted based on the first information such as the power generation amount obtained on the side of each of the power generation apparatuses 2820 to 2850 and presented to the user. On the side of the image display apparatus 2810, the perception range of the user can be extended by arranging and presenting information pieces obtained from the power generation apparatuses 2820 and 2850.

Note that a method of additionally providing each of the power generation apparatuses 2820 to 2850 with a sensor in order to monitor environmental factors such as the power storage amount of the battery in the installation location of each of the power generation apparatuses 2820 to 2850, the antenna strength, and the intensity of hazardous electromagnetic waves (ultraviolet rays) or radioactivity is also conceivable. However, with such sensors, each of the component cost of the power generation apparatuses 2820 to 2850 increases and the power consumption of the power generation apparatuses 2820 to 2850 also increases. As a result, the continuous use time is inevitably shortened. In contrast, as in this example, according to the method of transmitting the first information such as the power generation amount from each of the power generation apparatuses 2820 to 2850 and converting the first information received on the side of the image display apparatus 2820 into the second information such as the power storage amount of the battery, the antenna strength, and the intensity of hazardous electromagnetic waves (ultraviolet rays) or radioactivity, the apparatus cost of the power generation apparatuses 2820 to 2850 can be reduced. In addition, the power generation unit itself serves as the sensing device and a power-supply does not have to be provided. Therefore, the power consumption of each of the power generation apparatuses 2820 to 2850 is reduced. The limitation on the continuous use time is overcome and each of the power generation apparatuses 2820 to 2850 does not have to be increased in size for the battery.

Example 4

A monitoring system according to Example 4 positively uses information from the power generation apparatus mainly installed on the user as in the monitoring system according to Example 1 and monitors a state of the user such as health information from a living environment of the user.

In the monitoring system 700 according to Example 1, the image display apparatus 710 can mainly monitor, based on the first information such as the power generation amounts obtained by the two power generation apparatuses 720 and 730 worn by the left and right feet of the user, respectively, the exercise of the user on land, such as walking and running. Further, the arithmetic unit 633 can convert the power generation amount into the amount of exercise and thus monitoring of the posture of the user and posture balance control can be achieved. In contrast, in Example 4, a power generation apparatus is installed in a foot fin worn by the user during diving such as snorkeling and scuba diving. The first information such as the power generation amount of each power generation apparatus is converted into the second information such as the amount of exercise of the foot (number of kicks) and the water flow. Thus, the state of the user and the environment under water are monitored.

Figure 32:
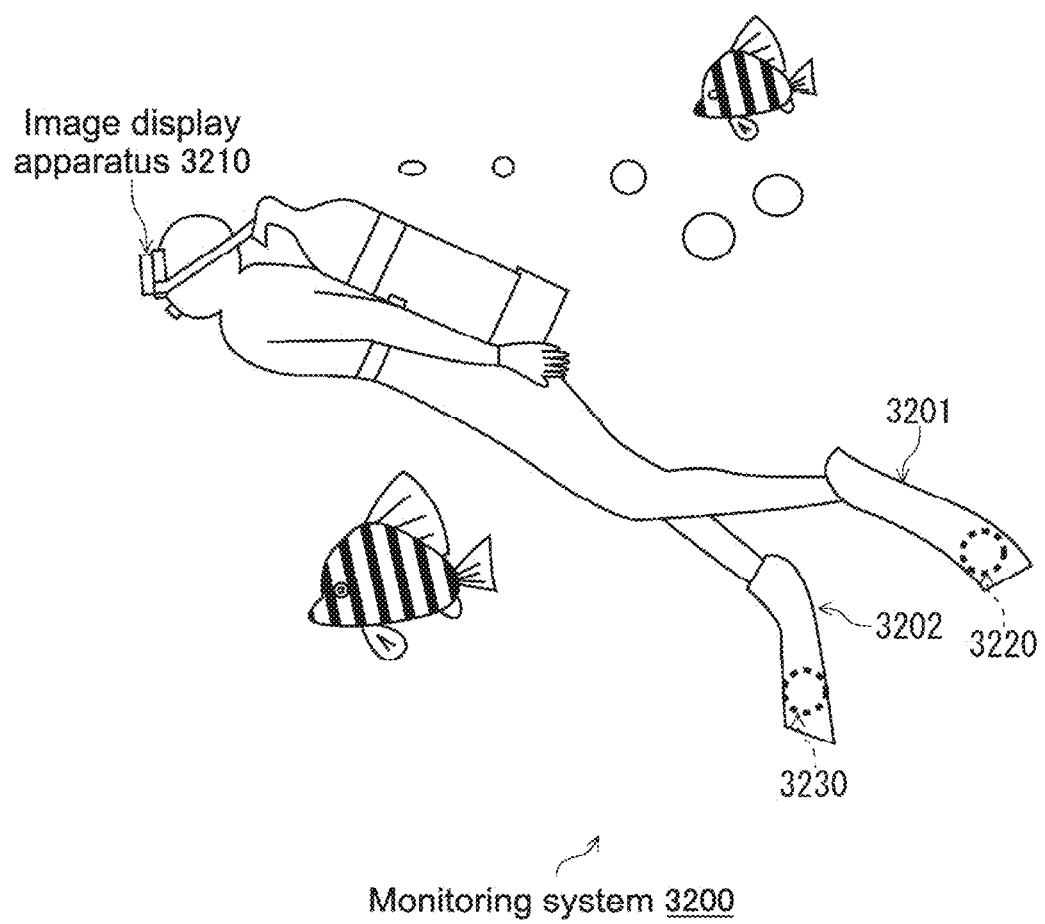
FIG. 32 is a diagram schematically showing a configuration of a monitoring system 3200 according to a fourth embodiment.

FIG. 32 schematically shows a configuration of a monitoring system 3200 according to Example 4. The monitoring system 3200 shown in the figure is formed of an image display apparatus 3210 and two power generation apparatuses 3220 and 3230 installed in foot fins 3201 and 3202 worn by the left and right feet of the user, respectively. The monitoring system 3200 basically has the functional configuration shown in FIG. 6. However, in FIG. 32, the system 3200 is shown in an abstract manner as it is operated.

Figure 33:
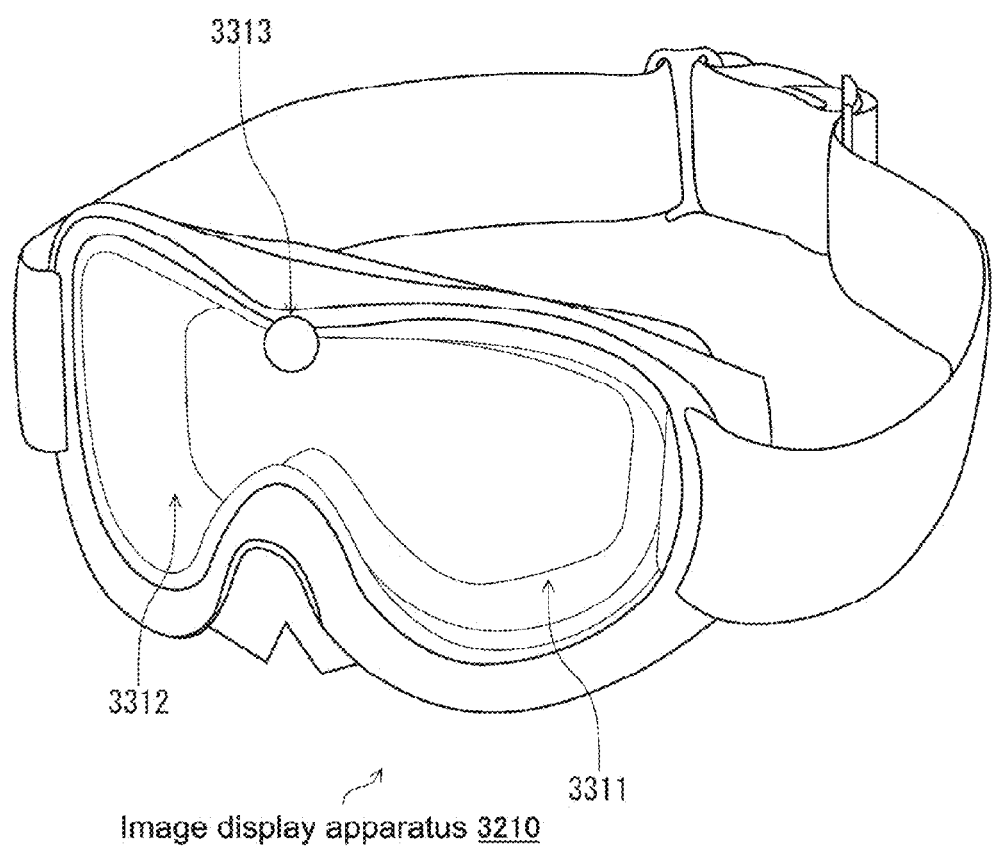
FIG. 33 is a diagram showing a configuration of an image display apparatus 3210.

The image display apparatus 3210 is, for example, configured integrally with goggles mounted on the head or face of the user during diving. FIG. 33 shows the image display apparatus 3210 in an enlarged state. The image display apparatus 3210 includes two display units 3311 and 3312 that present the left eye image and the right eye image to the left and right eyes of the user, respectively, and a water flow sensor 3313 that measures a flow of water flowing around the head of the user.

Each of the power generation apparatuses 3220 and 3230 includes a power generation unit, a storage element, and a communication unit (not shown). The power generation unit is formed of, for example, a vibration power generator (electrostatic type, electromagnetic type, inverse-magnetostrictive type, or piezoelectric type) that generates electrical power by converting mechanical vibrations generated when a mechanical vibration user moves under water into electrical power. The storage element is formed of, for example, a capacitor, a secondary battery, a spring, and a heat storage material and stores electrical power generated by the power generation unit or stores it as energy. The communication unit transmits the first information including the power generation amount of the power generation unit to the image display apparatus 3210. The communication unit can use a communication means such as wireless communication such as Wi-Fi and human body communication through the medium of the body of the user or wired communication (including signal transmission through an electroconductive fiber provided in a wet suit worn by the user). The communication unit may be constantly operated and transfer the first information such as the power generation amount in real time or may be intermittently operated and transfer the first information. Alternatively, the data may be directly exchanged between the left and right power generation apparatuses 3220 and 3230 or either one of the power generation apparatuses 3220 and 3230 may transfer the first information such as power generation amounts of the both to the image display apparatus 3210 together.

The image display apparatus 3210 displays the first information such as the power generation amount received from each of the power generation apparatuses 3220 and 3230 on at least either one of the left and right display units 3311 and 3312. For example, as in the display example shown in FIG. 8, the power generation amount of the power generation apparatus 3220 installed in the foot fin of the left foot may be displayed on the display unit 3311 for the left eye and the power generation amount of the power generation apparatus 3230 installed in the foot fin of the right foot may be displayed on the display unit 3312 for the right eye. Each of the power generation apparatuses 3220 and 3230 has a power generation amount depending on an amount of exercise of each of the left and right feet and the water flow caused by the exercise, and hence the arithmetic unit 633 may convert the power generation amount serving as the first information into the second information such as the amount of exercise of each of the left and right feet, the acceleration, and the water flow and display it.

If the flow of water around the head is detected using information on the water flow sensor 3313, the image display apparatus 3210 can control a direction of movement of the body of the user under water based on a relation between the amount of exercise of each of the left and right feet converted from the power generation amount of each of the power generation apparatuses 3220 and 3230. In general, there is a fear that a person is likely to lose the sense of direction under water and the person can move in an unexpected direction. In contrast, the image display apparatus 3210 can estimate a direction in which the user has moved based on the result of measurement of the water flow velocity observed by the water flow sensor 3313 and the second information such as the amount of exercise converted from the power generation amount of each of the power generation apparatuses 3220 and 3230 installed in the left and right foot fins 3201 and 3202. Moreover, the number of kicks of the left and right feet for correcting the direction of movement of the user who is swimming to an aiming direction (how much degree and with which of the left and right feet the user should kick) can be converted from the estimated direction of movement under water. The number of kicks of the left and right feet may be displayed on the left and right display units 3311 and 3312 (see reference numbers 3401 and 3402 in FIG. 34) together with displaying the power generation amount (reference numbers 3411 and 3412 in FIG. 34). Alternatively, audio guidance saying "Please kick three times with the right foot" may be provided.

Figure 34:
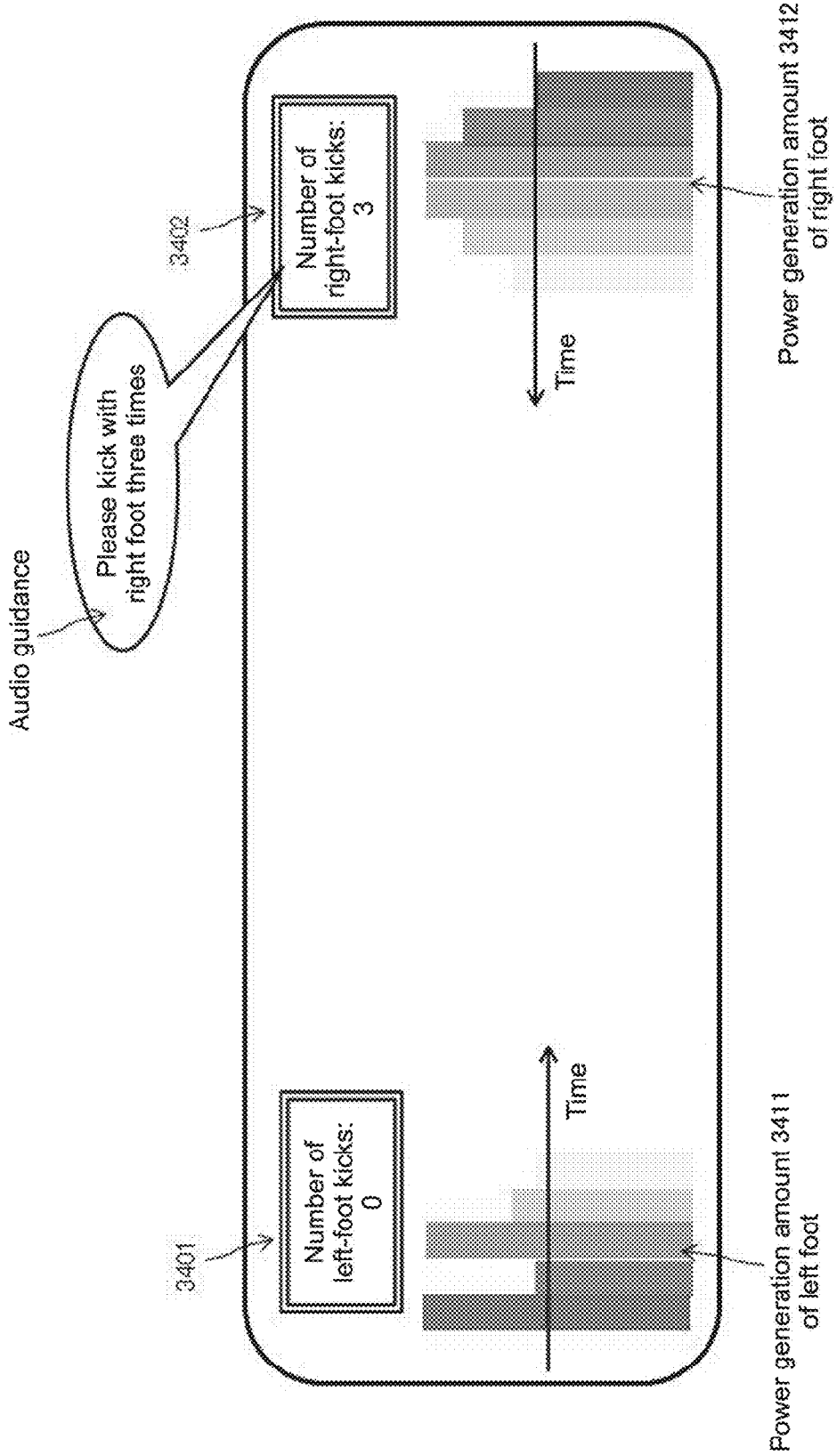
FIG. 34 is a diagram showing a display example in Example 4.

In the case where a map is displayed for instructing the user of the direction of movement, the user can move the feet according to the instruction only after the user understand the contents of the map. In contrast, as shown in FIG. 34, if the user is instructed of the direction of movement in the form of the number of kicks of the left and right feet, the user can modify the direction of movement and keep the sense of direction under water further much more easily than in the case where the map is displayed.

Figure 35:
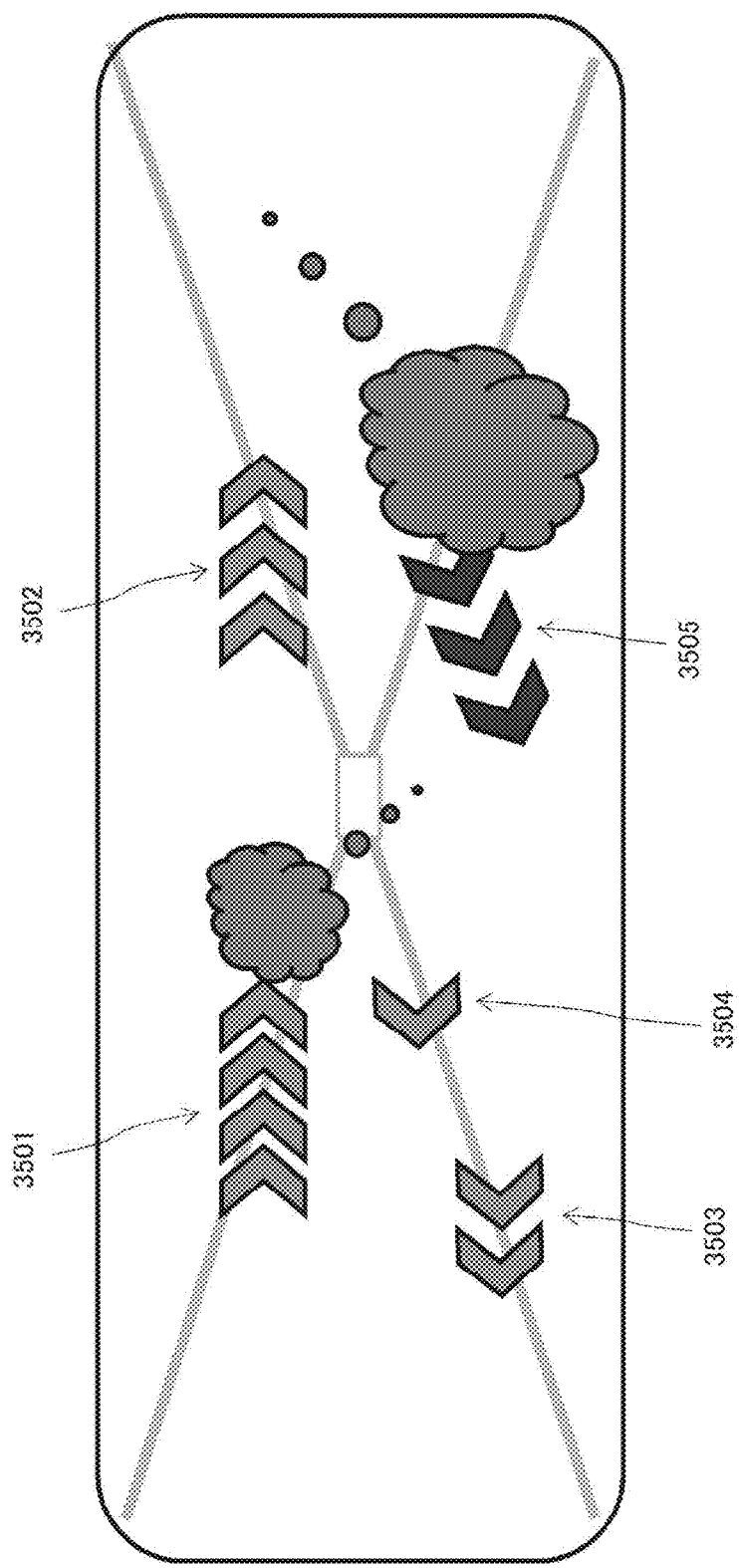
FIG. 35 is a diagram showing another display example in Example 4.

Alternatively, the image display apparatus 3210 may convert the power generation amounts of the power generation apparatuses 3220 and 3230 into the water flow serving as the second information and calculate the flow strength and direction of the water flow using information of the water flow sensor 3313, and then may display the result of calculation on the left and right display units 3311 and 3312 while the user is diving. FIG. 35 shows a state in which the flow strength and direction of the water flow observed by the water flow sensor 3313 as indicated by reference numbers 3501 to 3505 are displayed superimposed on the field of view of the user. Based on the underwater image displaying the flow strength and direction of the water flow, the user can know at a glance where the user encounters a danger. In the example shown in FIG. 35, it can be seen that a downward sea current is strong, which is dangerous.

In addition to merely displaying the information on the calculated water flow in the underwater image, the image display apparatus 3210 may derive, from the information on the water flow, control information for controlling the external device and reflect it in control of the external device. For example, the image display apparatus 3210 may change the loads connected to the power generation unit (vibration power generation element) in each of the power generation apparatuses 3220 and 3230 to thereby change the rigidity of the left and right foot fins, and control the direction of movement of the user. Alternatively, the vibration power generation element serving as the power generation unit may serve as a vibration actuator and driving thereof may be controlled.

After presenting the displayed image as shown in FIG. 35 to the user, the image display apparatus 3210 can upload an underwater image itself or the first information such as the power generation amount and the second information such as the water flow into the server on the Internet (not shown) (including posting to an information providing site) or transmit it to information terminals of other users through direct communication such that the information on the water flow can be shared between the users (for example, current state of a center that checks the safety of a beach can be shared). By adding up information pieces transmitted from a plurality of users in the server, for example, estimation of a dangerous location in a swimming area or warning the user entering a dangerous zone can be performed.

By displaying the image visualizing the water flow as shown in FIG. 35 also in the external display unit 515, the image display apparatus 3210 can present the water flow condition of the environment also to people around the user.

According to the monitoring system 3200 of this example, the second information that is out of a perception range for the user wearing the image display apparatus 3210 or difficult to perceive can be presented to the user based on the first information such as the power generation amount obtained on the side of each of the power generation apparatuses 3220 and 3230 and the second information such as the water flow that is converted from the first information. On the side of the image display apparatus 3210, the perception range of the user can be extended by arranging and presenting information pieces obtained from the power generation apparatuses 3220 and 3230.

Note that a method of additionally providing each of the power generation apparatuses 3220 and 3230 with the water flow sensor, to thereby directly measure the amount of information equivalent to the above-mentioned second information such as the water flow applied on the left and right feet is also conceivable. However, with such sensors, the component cost of the power generation apparatuses 3220 and 3230 increases and the power consumption of the power generation apparatuses 3220 and 3230 also increases. As a result, the continuous use time is inevitably shortened. In contrast, as in this example, according to the method of transmitting the first information such as the power generation amount from the power generation apparatuses 3220 and 3230 and converting the first information received on the side of the image display apparatus 3210 into the amount of exercise of the user to estimate the direction of movement of the user, the apparatus cost can be reduced. Moreover, the power generation unit itself in each of the power generation apparatuses 3220 and 3230 serves as the sensing device and a power-supply does not have to be provided. Therefore, the power consumption of the entire system 3200 is reduced. The limitation on the continuous use time is overcome and the power generation apparatuses 3220 and 3230 do not have to be increased in size for the batteries.

Figure 36:
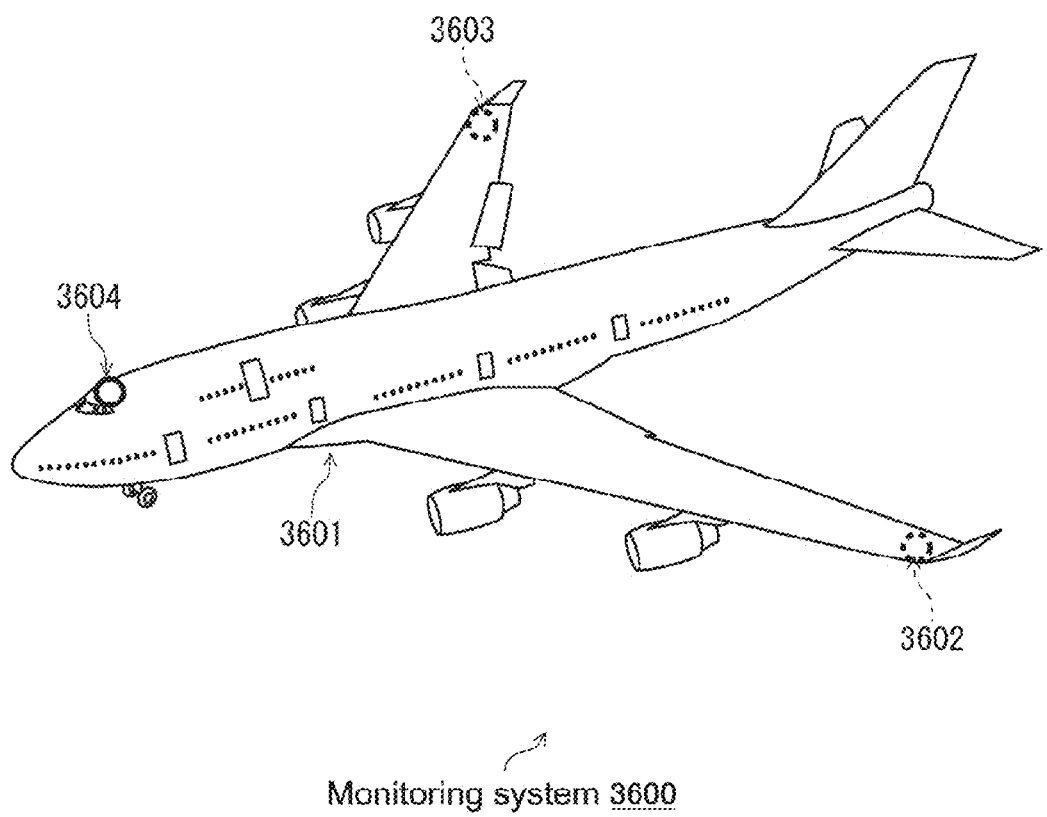
FIG. 36 is a diagram schematically showing a configuration of a monitoring system 3600 according to a modified example of Example 4.

As a modified example of Example 4 shown in FIG. 32, as shown in FIG. 36, the following monitoring system 3600 can be exemplified. Specifically, in the monitoring system 3600, an airflow sensor 3604 is mounted on the head of an aircraft 3601 (may be a helicopter or another flying object), an image display apparatus (not shown) is installed in a cockpit, and power generation apparatuses 3602 and 3603 are installed in the vicinity of leading ends of left and right main wings, respectively. The image display apparatus is, for example, a head-mounted display that is worn by a pilot sitting in the cockpit.

Figure 37:
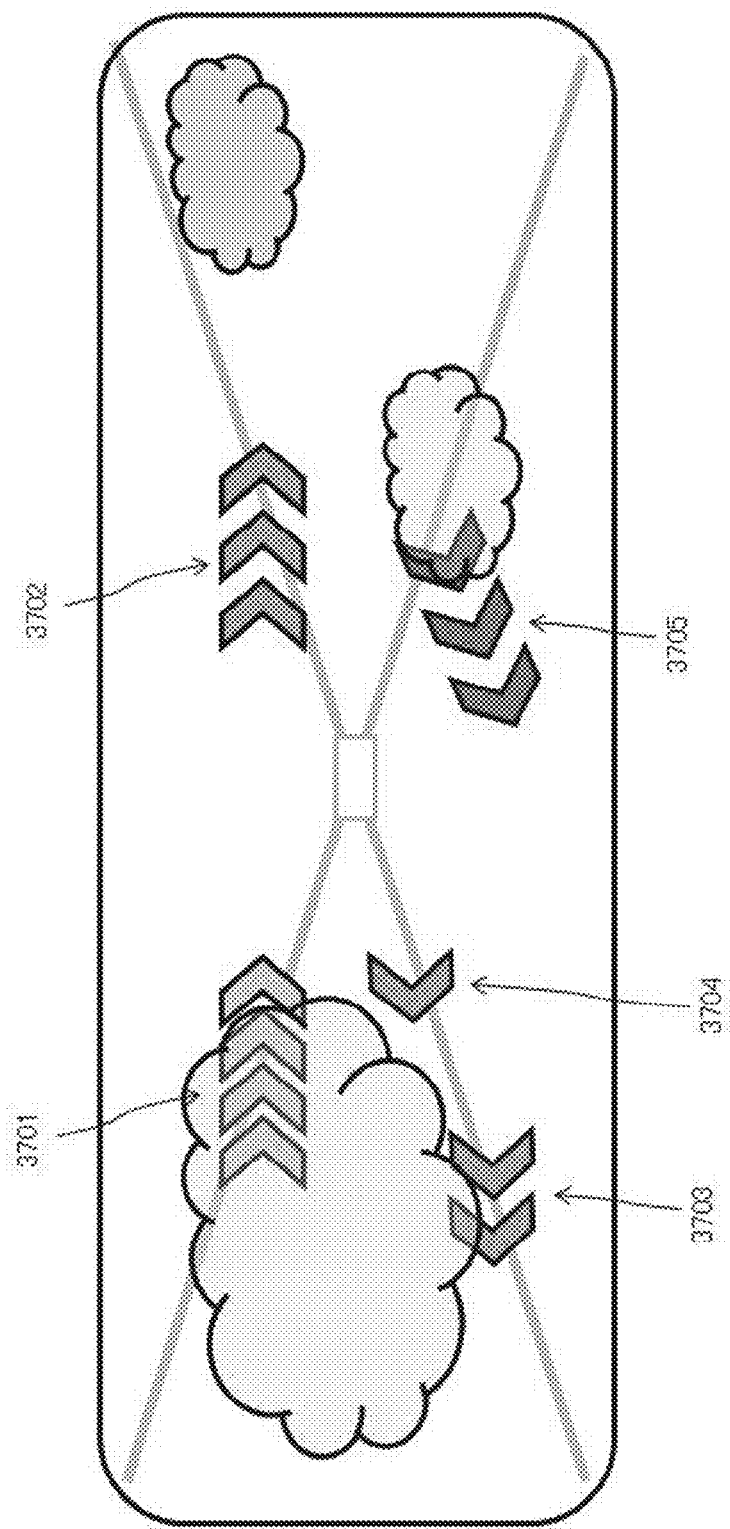
FIG. 37 is a diagram showing still another display example in Example 4.

It is assumed that the power generation amount of each of the power generation apparatuses 3602 and 3603 is proportional to the airflow in its location. In view of this, in the image display apparatus in the cockpit, the arithmetic unit 633 converts the first information such as the power generation amounts of the power generation apparatuses 3602 and 3603 installed in the left and right main wings into the second information such as momentum, acceleration, and airflow of the aircraft 3601. The image display apparatus may use information of the airflow sensor 3604 to calculate the flow strength and direction of the airflow when the aircraft 3601 is flying, and display them. FIG. 37 shows a state in which the flow strength and direction of the airflow observed by the airflow sensor 3604 are displayed superimposed on a landscape of the sky seen from the cockpit, as indicated by reference numbers 3701 to 3705. Based on the sky image showing the flow strength and direction of the airflow, the user of the image display apparatus such as the pilot can know at a glance where is dangerous. In the example shown in FIG. 37, it can be seen that a downward airflow is strong, which is dangerous.

In addition to merely displaying the second information such as the airflow calculated by the image display apparatus in the sky image, the control information for the external device may be derived from the second information and reflected in control of the external device. For example, in the image display apparatus in the cockpit, the arithmetic unit 633 may derive control information for controlling driving of ailerons and an empennage from the flow strength and direction of the airflow calculated as the second information, to thereby automatically control the direction of movement of the aircraft 3601.

After presenting the displayed image as shown in FIG. 37 to the user such as the pilot, the image display apparatus may upload the displayed sky image itself, the first information such as the power generation amount, or the second information such as the airflow into the server on the Internet (not shown) (including posting to an information providing site) or transmit it to information terminals of other users through direct communication. For example, a center that checks the safety, such as a control tower, collects information pieces transmitted from aircrafts and the current state of the sky can be shared with the aircrafts via the center. Alternatively, based on the information pieces collected by the center, it is possible to improve the position resolution of weather information (e.g., prediction of local weather such as a guerrilla rainstorm).

By displaying the image visualizing the airflow as shown in FIG. 37 also on the external display unit 515, the image display apparatus can present, also to people around the user such as a copilot, the airflow condition of the environment.

Example 5

A monitoring system according to Example 5 positively uses information from a plurality of power generation apparatuses installed in matters other than the user as in the monitoring system according to Example 3 and monitors an environment in the location where each of the power generation apparatuses is installed.

The monitoring system 2800 according to Example 3 can convert the first information such as the power generation amount obtained by each of the power generation apparatuses 2820, 2830, 2840, and 2850 using the environmental electromagnetic waves, which are installed in the surrounding environment of the user, into the second information such as the antenna strength and the intensity of hazardous electromagnetic waves (ultraviolet rays) or radial rays in each location of the surrounding environment of the user, and visualize and display this (e.g., see FIGS. 30 and 31). In contrast, the monitoring system according to Example 5 is similar to Example 3 in that a plurality of power generation apparatuses are in a field and characterized in that each power generation apparatus generates electrical power mainly using sunlight.

Figure 38:
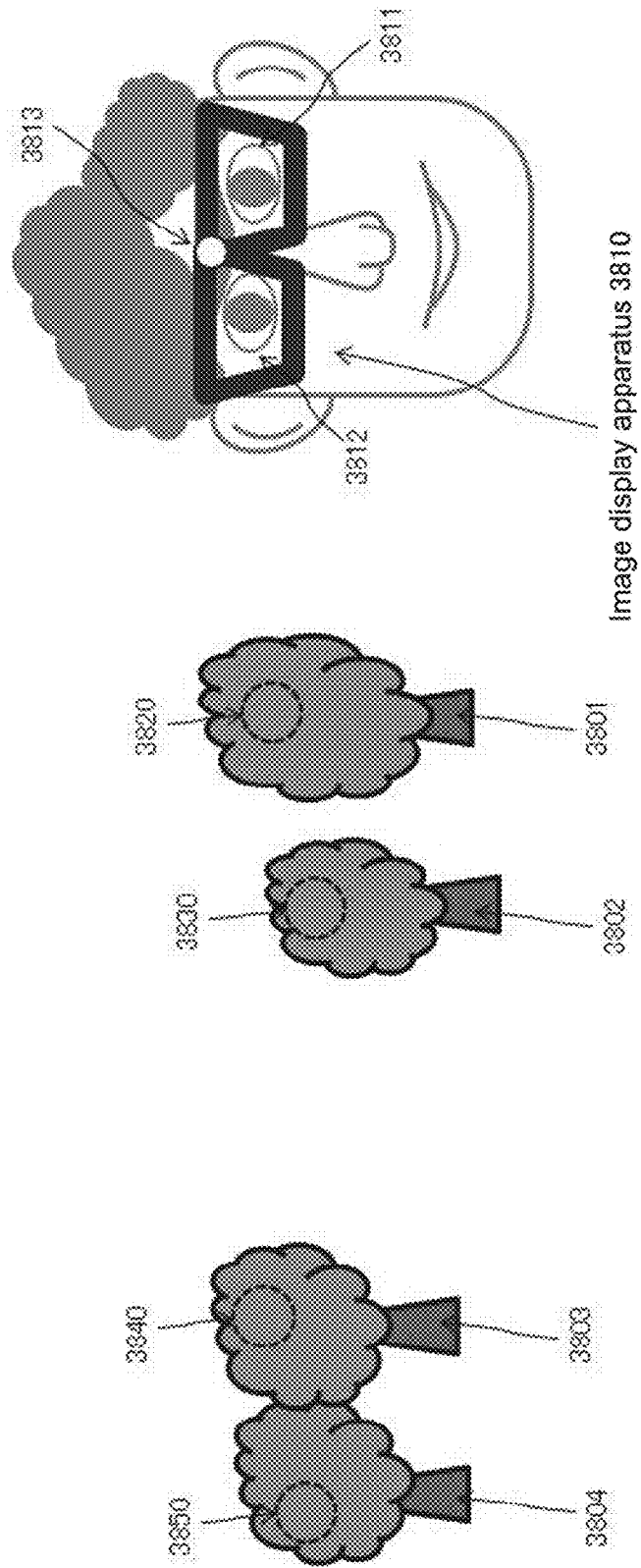
FIG. 38 is a diagram schematically showing a configuration of a monitoring system 3800 according to Example 5.

FIG. 38 schematically shows a configuration of a monitoring system 3800 according to Example 5. The monitoring system 3800 shown in the figure is formed of an image display apparatus (head-mounted display) 3810 that is used by being mounted on the head or face of the user and a plurality of power generation apparatuses 3820, 3830, 3840, and 3850 installed in cultivation places 3801, 3802, 3803, and 3804 for farm products in a farm such as an orchard or a field. The monitoring system 3800 basically has the functional configuration shown in FIG. 6. However, in FIG. 38, the system 3800 is shown in an abstract manner as it is operated.

The image display apparatus 3810 includes two display units 3811 and 3812 that present the left eye image and the right eye image to the left and right eyes of the user, respectively, an optical sensor 3813 that measures a quantity of light such as an amount of solar radiation, and the external camera 512 (not shown in FIG. 38).

Each of the power generation apparatuses 3820 to 3850 includes a power generation unit, a storage element, and a communication unit (not shown). The power generation unit is formed of, for example, any one or a combination of two or more of a solar-cell power generation element that generates electrical power using sunlight, an ultraviolet-ray power generation element that generates electrical power using ultraviolet rays, and an infrared-ray power generation element that generates electrical power using infrared rays. The power generation unit generates the obtained electrical power in the storage element such as a secondary battery.

The communication unit uses, for example, wireless communication such as Wi-Fi to exchange data with the image display apparatus 3810. The communication unit may be constantly operated and transfer the first information such as the power generation amount of the power generation unit in real time or may be intermittently operated and transfer the first information. Alternatively, the communication unit may communicate and directly exchange the data with other power generation apparatuses.

The image display apparatus 3810 displays a result of processing the first information such as the power generation amounts received from the power generation apparatuses 3820 to 3850 on the left and right display units 3811 and 3812. For example, the image display apparatus 3810 displays the power generation amounts of the power generation apparatuses 3820 to 3850 on the left and right display units 3811 and 3812. If the image display apparatus 3810 is a see-through type head-mounted display, the power generation amounts of the power generation apparatuses 3820 to 3850 are subjected to space mapping and displayed superimposed on their installation locations.

It is assumed that the power generation amount of each of the power generation apparatuses 3820 to 3850 is proportional to the amount of solar radiation in its location. In view of this, in the image display apparatus 3810, the arithmetic unit 633 converts the power generation amount of each of the power generation apparatuses 3820 to 3850 at each time into the amount of solar radiation serving as the second information. By storing the amount of solar radiation at each time in the storage unit 516 and observing transition thereof, a sunshine state in each of the locations 3801, 3802, 3803, and 3804 (i.e., where and when the amount of solar radiation is larger) can be determined. The locations 3801, 3802, 3803, and 3804 may be displayed on the left and right display units 3811 and 3812. For example, if the image display apparatus 3810 is a see-through type head-mounted display, information pieces on sunshine states are subjected to space mapping and displayed superimposed on the locations 3801, 3802, 3803, and 3804 where the power generation apparatuses are installed. Thus, distribution of the sunshine state in the real world can be visualized.

Figure 39:
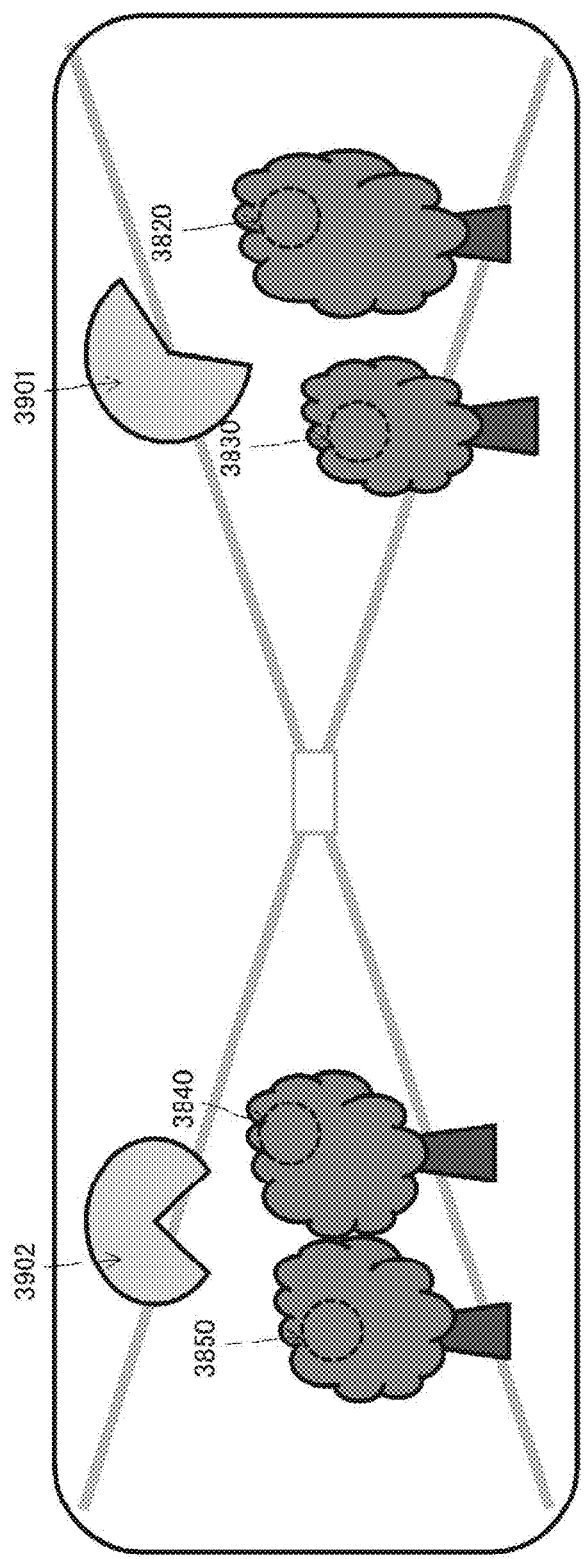
FIG. 39 is a diagram showing a display example in Example 5.

FIG. 39 shows an example in which the image display apparatus 3810 visualizes the sunshine state in each location, which is obtained based on the power generation amount of each of the power generation apparatuses 3820 to 3850 dispersedly arranged in the farm. In the example shown in the figure, an icon 3901 indicating a sunshine state (time and sunlight level) in a region in which power generation apparatuses 3820 and 3830 are located and an icon 3902 indicating a sunshine state in a region in which power generation apparatuses 3840 and 3850 are located are displayed superimposed on each region. With this, the user can know at a glance where the sufficiently charged secondary battery is in the farm, and can also know where the amount of solar radiation is larger and farm products can grow more easily.

The image display apparatus 3810 derives the third information such as the control information for controlling the image display apparatus 3810 itself or the external device from the amount of solar radiation serving as the second information converted from the power generation amount as shown in FIG. 39. For example, the control information that is reflected in control of time and frequency of sprinkling by a sprinkler and time and frequency of sprinkling of agrochemicals and fertilization, operation of a harvesting machine, and operation of a weeding/insecticidal machine, or the like can be derived from the amount of solar radiation.

After presenting the displayed image as shown in FIG. 39 to the user, the image display apparatus 3810 can upload it into the server on the Internet (not shown) (including posting to an information providing site) or transmit it to information terminals of other users through direct communication such that the information on the sunshine state in the farm can be shared between the users.

By displaying the displayed image shown in FIG. 39 also on the external display unit 515, the image display apparatus 3810 can present the information on the sunshine state in the farm also to people around the user.

A degree of growth of farm products largely depends on the sunshine state. In view of this, in the image display apparatus 3810, the arithmetic unit 633 can further derive, from the sunshine state in each location that is converted from the power generation amount of each of the power generation apparatuses 3820 to 3850 as the second information, the third information such as growth level, harvest period, and harvest order of the farm products in each location.

Figure 40:
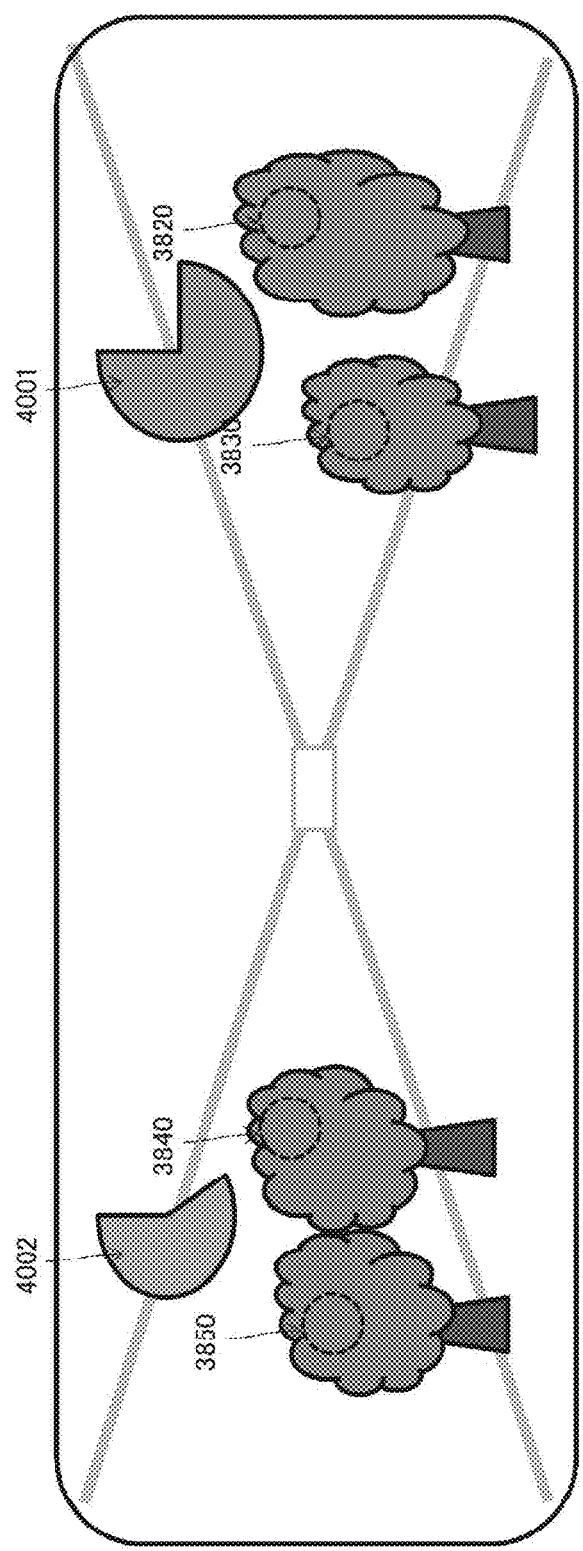
FIG. 40 is a diagram showing another display example in Example 5.

FIG. 40 shows an example in which the image display apparatus 3810 visualizes the growth level of the farm products in each location, which is derived from the amount of solar radiation in the installation location of each of the power generation apparatuses 3820 to 3850 in the farm as the third information. In the example shown in the figure, an icon 4001 indicating the growth level of the farm products in a region in which the power generation apparatuses 3820 and 3830 are located and an icon 4002 indicating the growth level of the farm products in a region in which the power generation apparatuses 3840 and 3850 are located are displayed superimposed on each region. With this, the user can see at a glance where the sufficiently charged secondary battery is in the farm and can also know period and order for harvesting the farm products in the farm.

After presenting the displayed image as shown in FIG. 40 to the user, the image display apparatus 3810 can upload it into the server on the Internet (not shown) (including posting to an information providing site) or transmit it to information terminals of other users through direct communication such that the information on the growth level of the farm products in the farm can be shared between the users.

By displaying the displayed image shown in FIG. 40 also on the external display unit 515, the image display apparatus 3810 can present information on the growth level of the farm products in the farm also to people around the user.

In addition, by comparing the growth level of the farm products in the reality with the growth level converted from the power generation amount, a health state of the farm products can be diagnosed. For example, it can be understood that farm products having a large amount of solar radiation but a low growth speed lack nutrients or are affected by pests. In view of this, in the image display apparatus 3810, the arithmetic unit 633 can calculate the actual growth level of the farm products in the farm by performing image analysis processing, such as feature amount extraction, on the landscape of the farm that is captured by the external camera 512, and compare this with the growth level converted from the power generation amount to thereby estimate the health state of the farm products.

The image display apparatus 3810 can reflect the diagnosed health state of the farm products in control of the image display apparatus 3810 itself or the external device (time and frequency of sprinkling by a sprinkler and control of time and frequency of sprinkling of agrochemicals and fertilization, operation of a harvesting machine, and operation of a weeding/insecticidal machine, or the like). The image display apparatus 3810 can upload information on the estimated growth level, harvest period, harvest order, and health state of the farm products into the server on the Internet (not shown) (including posting to an information providing site) or transmit it to information terminals of other users through direct communication such that it can be shared between the users.

According to the monitoring system 3800 of this example, the second information such as the amount of solar radiation that is out of a perception range for the user wearing the image display apparatus 3810 or difficult to perceive can be converted based on the first information such as the power generation amount that is obtained on the side of each of the power generation apparatuses 3820 to 3850. In addition, the third information such as the growth level and the health state of the farm products can be derived and presented to the user. On the side of the image display apparatus 3810, the perception range of the user can be extended by arranging and presenting information pieces obtained from the power generation apparatuses 3820 to 3850.

Note that a method of additionally providing each of the power generation apparatuses 3820 to 3850 with an optical sensor that measures the quantity of light or the like in order to monitor environmental factors such as the amount of solar radiation for each of the locations 3801 to 3804 is also conceivable. However, with such sensors, the component cost of the power generation apparatuses 3820 to 3850 increases and the power consumption of the power generation apparatuses 3820 to 3850 also increases. As a result, the continuous use time is inevitably shortened. In contrast, as in this example, according to the method of transmitting the first information such as the power generation amount from each of the power generation apparatuses 3820 to 3850 and converting the first information received on the side of the image display apparatus 3810 into the second information such as the amount of solar radiation, the apparatus cost can be reduced. In addition, the power generation unit itself serves as the sensing device and a power-supply does not have to be provided. Therefore, the power consumption of the entire system 3800 is reduced. The limitation on the continuous use time is overcome and the power generation apparatuses 3820 to 3850 do not have to be increased in size for the batteries.

Example 6

A monitoring system according to Example 6 positively uses information from a plurality of power generation apparatuses installed in matters other than the user as in the monitoring system according to Example 3 and monitors an environment in the location where each of the power generation apparatuses is installed.

Figure 41:
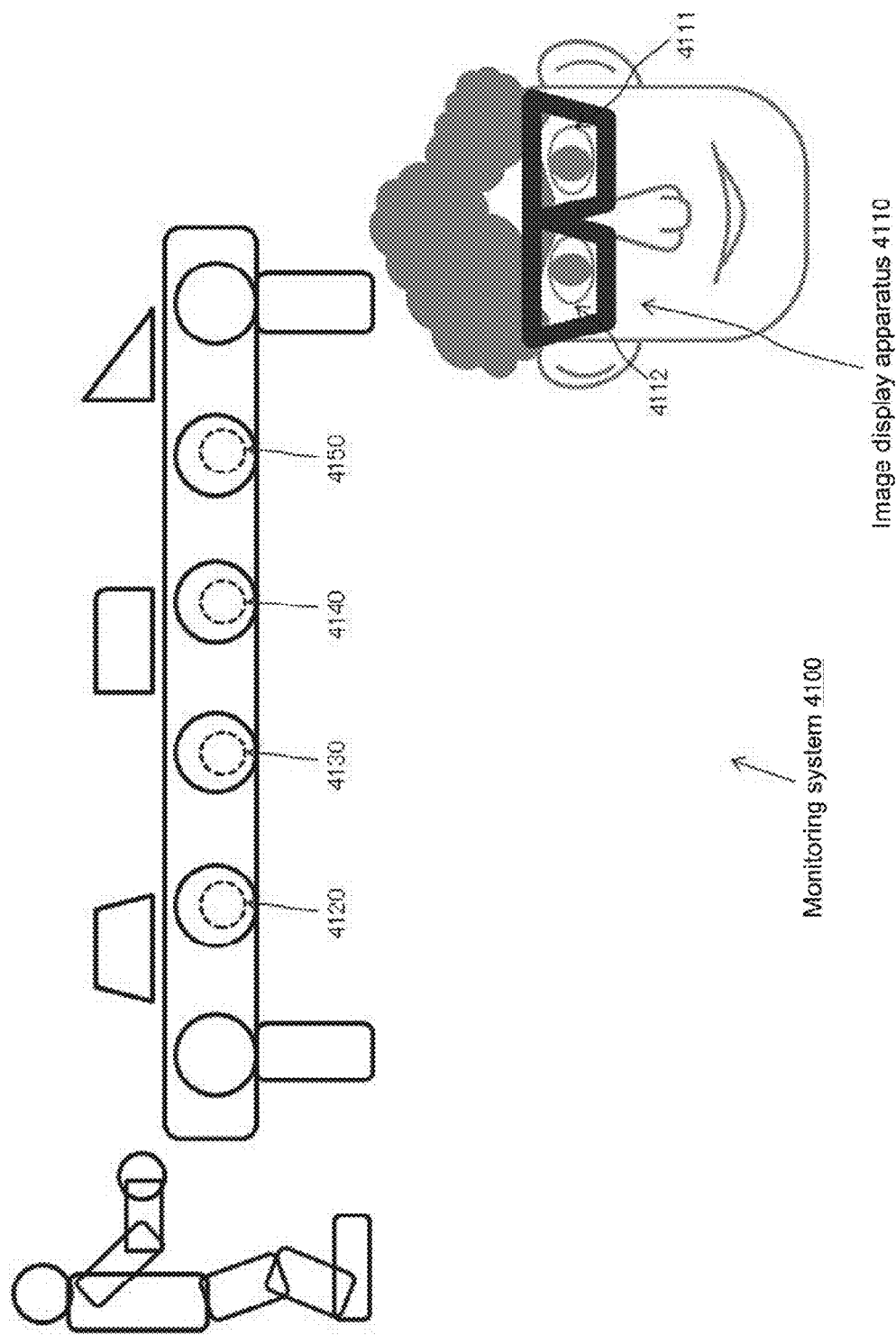
FIG. 41 is a diagram schematically showing a configuration of a monitoring system 4100 according to Example 6.

FIG. 41 schematically shows a configuration of a monitoring system 4100 according to Example 6. The monitoring system 4100 shown in the figure is formed of an image display apparatus (head-mounted display) 4110 that is used by being mounted on the head or face of the user and a plurality of power generation apparatuses installed in the surrounding environment of the user. In the example shown in the figure, power generation apparatuses 4120, 4130, 4140, and 4150 are installed in a manufacturing line in a factory in which the user is located (or under the control/supervision of the user). As a matter of course, it is also conceivable that five or more or three or less power generation apparatuses are installed. The monitoring system 4100 basically has the functional configuration shown in FIG. 6. However, in FIG. 41, the system 4100 is shown in an abstract manner as it is operated in a manufacturing line.

The image display apparatus 4110 includes two display units 4111 and 4112 that present the left eye image and the right eye image to the left and right eyes of the user, respectively.

Each of the power generation apparatuses 4120 to 4150 includes a power generation unit, a storage element, and a communication unit (not shown). The power generation unit generates electrical power using a temperature difference and stores the obtained electrical power in the storage element such as a secondary battery. For example, a thermoelectric conversion element (including power generation due to the Seebeck effect, the Thomson effect, or the like, a thermoelectric element, thermomagnetic power generation, and the like) or a vibration or motion power generator (electrostatic type, electromagnetic type, inverse-magnetostrictive type, or piezoelectric type) that generates electrical power using vibrations can be used as the power generation unit.

The communication unit uses, for example, wireless communication such as Wi-Fi to exchange data with the image display apparatus 4110. The communication unit may be constantly operated and transfer the first information such as the power generation amount of the power generation unit in real time or may be intermittently operated and transfer the first information. Alternatively, the communication unit may communicate and directly exchange the data with other power generation apparatuses.

The image display apparatus 4110 displays the second information obtained by converting the first information such as the power generation amounts received from the power generation apparatuses 4120 to 4150 and the third information derived from the second information on the left and right display units 4111 and 4112. For example, the image display apparatus 4110 displays the power generation amounts of the power generation apparatuses 4120 to 4150 on the left and right display units 4111 and 4112. If the image display apparatus 4110 is a see-through type head-mounted display, the power generation amounts thereof are subjected to space mapping and displayed superimposed on locations where the power generation apparatuses 4120 to 4150 are installed. Thus, distribution of charged secondary batteries in the real world can be visualized. Through such a displayed image, the user can know at a glance where the sufficiently charged secondary battery is and with which of the batteries the user should perform replacement.

Figure 42:
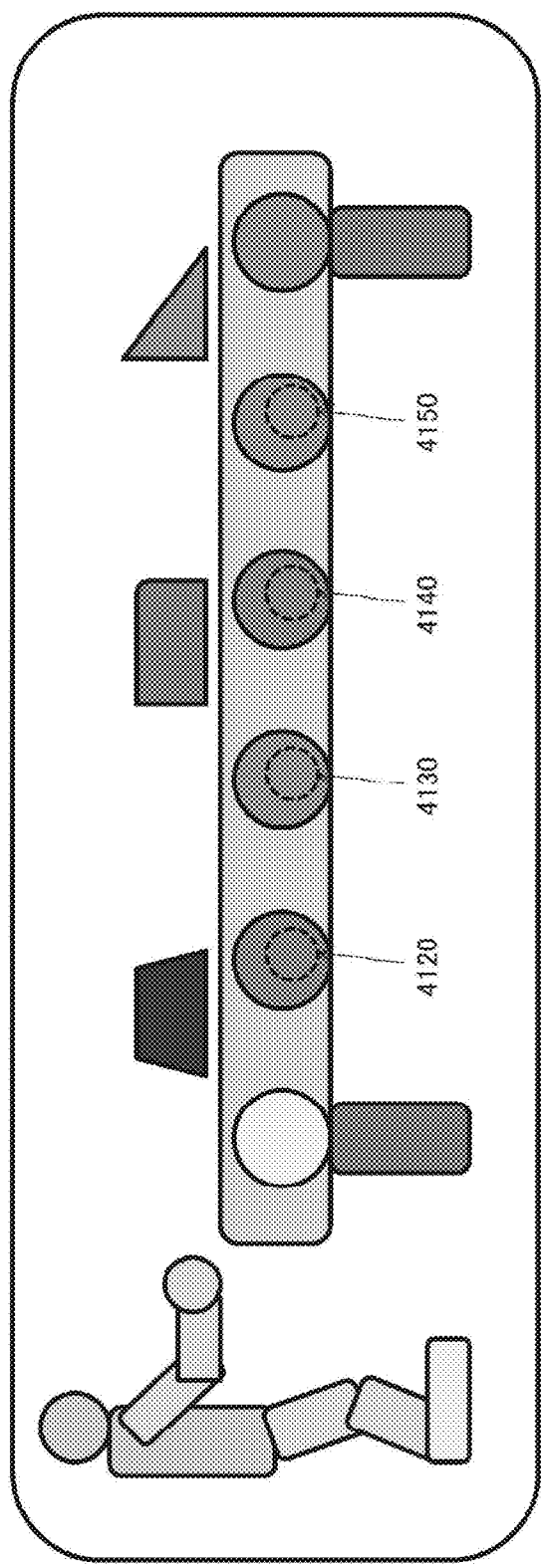
FIG. 42 is a diagram showing a display example in Example 6.

It is assumed that the power generation amount of each of the power generation apparatuses 4120 to 4150 corresponds to the temperature or mechanical vibrations in its location. In view of this, in the image display apparatus 4110, the arithmetic unit 633 may convert the power generation amounts of the power generation apparatuses 4120 to 4150 into the temperature or mechanical vibrations generated in their installation locations and display them on the left and right display units 4111 and 4112. For example, If the image display apparatus 4110 is a see-through type head-mounted display, the temperature or mechanical vibrations calculated with respect to the power generation apparatuses 4120 to 4150 are subjected to space mapping and displayed on the locations where they are installed. Thus, distribution of the temperature in the real world (i.e., in a factory) can be visualized. FIG. 42 shows an example in which the image display apparatus 4110 visualizes the temperature or mechanical vibrations in each location, which is obtained based on the power generation amount of each of the power generation apparatuses 4120 to 4150 installed in the manufacturing line of the factory. In the example shown in the figure, the distribution of the temperature or distribution of mechanical vibrations in each location is expressed by shading (higher-temperature location or higher-amplitude vibration location is expressed by darker shading).

The location in the manufacturing line, which has a high temperature or high amplitude vibrations, can be considered as a dangerous point. Thus, the arithmetic unit 633 of the image display apparatus 4110 can detect the dangerous point where excess heat (i.e., energy loss) is generated, for example, based on the temperature or vibrations converted from the power generation amount of each of the power generation apparatuses 4120 to 4150 as the second information.

From the displayed image shown in FIG. 42, the user can visually judge where the sufficiently charged secondary battery is in the real world (i.e., in a factory), and can also detect a dangerous point and visually check whether or not excess heat (i.e., energy loss) is generated. In addition, the arithmetic unit 633 of the image display apparatus 4110 can derive the third information such as the control information for the external device based on the distribution of the temperature or the distribution of the mechanical vibrations converted as the second information. For example, it can also be used for controlling an external device such as a fire extinguishing apparatus and an alarm apparatus.

The image display apparatus 4110 can upload information on the calculated temperature distribution or vibration distribution in the factory, such as the image shown in FIG. 42, into the server on the Internet (not shown) (including posting to an information providing site) or transmit it to information terminals of other users through direct communication, such that it can be shared between the users and the users can together check whether or not excess heat or unnecessary mechanical vibrations (i.e., energy loss) is generated.

By displaying the displayed image shown in FIG. 42 also on the external display unit 515, the image display apparatus 4110 can present the information on the dangerous point in the manufacturing line and the point where the energy loss is generated, also to people around the user.

According to the monitoring system 4100 of this example, the second information such as the distribution of the temperature and the distribution of the vibrations that is out of a perception range for the user wearing the image display apparatus 4110 or difficult to perceive can be converted based on the first information such as the power generation amount that is obtained on the side of each of the power generation apparatuses 4120 to 4150. In addition, the third information such as a dangerous point in the manufacturing line can be derived and presented to the user. On the side of the image display apparatus 4110, the perception range of the user can be extended by arranging and presenting information pieces obtained from the power generation apparatuses 4120 to 4150.

Note that a method of additionally providing each of the power generation apparatuses 4120 to 4150 with a temperature sensor or a vibration sensor in order to monitor environmental factors such as the temperature and mechanical vibrations in the installation location of each of the power generation apparatuses 4120 to 4150 is also conceivable. However, with such sensors, the component cost of the power generation apparatuses 4120 to 4150 increases and the power consumption also increases. As a result, the continuous use time is inevitably shortened. In contrast, as in this example, according to the method of transmitting the first information such as the power generation amount from each of the power generation apparatuses 4120 to 4150 and converting the first-information power generation amount received on the side of the image display apparatus 4110 into the second information such as the temperature and mechanical vibrations, the apparatus cost can be reduced. In addition, the power generation unit itself serves as the sensing device and a power-supply does not have to be provided. Therefore, the power consumption of the entire system 4100 is reduced. The limitation on the continuous use time is overcome and the power generation apparatuses 4120 to 4150 do not have to be increased in size for the batteries.

If each of the power generation apparatuses 4120 to 4150 performs vibration power generation, by converting the power generation amount serving as the first information into the vibration amount serving as the second information, it is possible to judge, based on abnormal vibrations, failure points in the manufacturing line, failure components conveyed on the manufacturing line, and the like. Consequently, it is possible to make the works safe and avoid the failure of manufacturing targets.

The power generation unit of each of the power generation apparatuses 4120 to 4150 may be replaced by a radio-wave power generation element that induces electrical power to the power generation element using the radio waves (far electromagnetic field) or a near electromagnetic field-used power generation element that induces electrical power to the element due to an electromagnetic field in a neighboring region, which includes electromagnetic induction and electrostatic induction. In this case, by converting the power generation amount serving as the first information into the radio-wave intensity serving as the second information, an abnormal point of an electrical apparatus or component in the manufacturing line or a dangerous point such as a strong electromagnetic field where an abnormality can occur in an electrical conduction point, a human body, and a pacemaker can be derived as the third information. Based on the display of the third information, the user can avoid contact with such a dangerous point (avoid electric shock or destruction of a component). The power generation unit of each of the power generation apparatuses 4120 to 4150 can also be formed of a power generation element that generates electrical power using pressure fluctuation. The pressure fluctuation is physically synonymous with the mechanical vibrations. Therefore, a power generation element similar to the power generation element using the mechanical vibrations can be used. It should be noted that it is aimed at finding not a point where an abnormal operation is being performed as a mechanical operation but a pressure fluctuation of a pressure container that is apparently statistic and avoiding the contact of the user with the point where an abnormal pressure occurs. As a matter of course, some or all of the power generation apparatuses 4120 to 4150 may be configured to generate electrical power by combining temperature-difference power generation, vibration power generation, and radio-wave power generation.

Example 7

A monitoring system according to Example 7 positively uses information from the power generation apparatus installed in a matter other than the user as in the monitoring system according to Example 3 and monitors an environment in the location where the power generation apparatus is installed.

Figure 43:
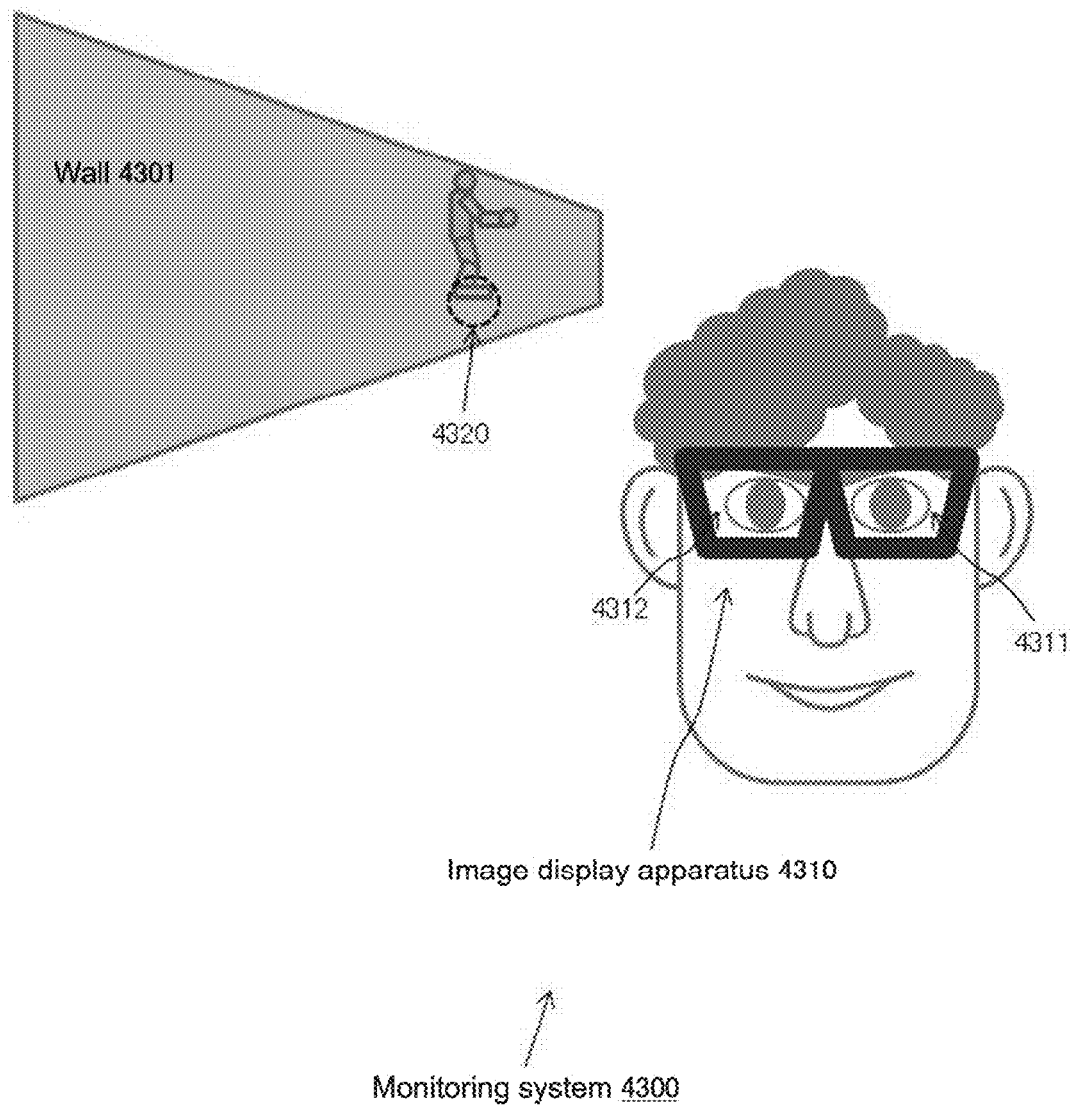
FIG. 43 is a diagram schematically showing a configuration of a monitoring system 4300 according to Example 7.

FIG. 43 schematically shows a configuration of a monitoring system 4300 according to Example 7. The monitoring system 4300 shown in the figure is formed of an image display apparatus (head-mounted display) 4310 that is used by being mounted on the head or face of the user and a power generation apparatus 4320 that performs both of sunlight power generation and mechanical-vibration power generation. The power generation apparatus 4320 is used by being installed on, for example, a moving object that moves in a street, such as a person and car. In the example shown in the figure, the power generation apparatus 4320 is installed on a person in a location that cannot be seen by the user because a wall 4301 (or another obstacle) blocks the field of view of the user, for example. Although only one power generation apparatus 4320 is shown in FIG. 43, it is also conceivable that a plurality of power generation apparatuses are dispersedly arranged in the real world. The monitoring system 4300 basically has the functional configuration shown in FIG. 6. However, in FIG. 43, the system 4300 is shown in an abstract manner as it is operated.

The image display apparatus 4310 includes two display units 4311 and 4312 that present the left eye image and the right eye image to the left and right eyes of the user, respectively.

The power generation apparatus 4320 includes a power generation unit, a storage element, and a communication unit (not shown). The power generation unit is formed of a combination of a solar-cell power generation element that generates electrical power using sunlight (including an ultraviolet-ray power generation element that generates electrical power using ultraviolet rays and an infrared-ray power generation element that generates electrical power using infrared rays) and a power generation element that generates electrical power using vibrations (electrostatic type, electromagnetic type, inverse-magnetostrictive type, or piezoelectric type).

The communication unit uses, for example, wireless communication such as Wi-Fi to exchange data with the image display apparatus 4310. The communication unit may be constantly operated and transfer the first information such as the power generation amount of the power generation unit in real time or may be intermittently operated and transfer the first information. Alternatively, the communication unit may communicate and directly exchange the data with other power generation apparatuses.

The image display apparatus 4310 can convert the power generation amount of the power generation apparatus 4320 into the second information such as sunlight intensity and generated mechanical vibrations in the installation location thereof. Further, the image display apparatus 4310 displays the second information obtained by converting the first information such as the power generation amount received from the power generation apparatus 4320 and the third information derived from the second information on the left and right display units 4311 and 4312.

Figure 44:
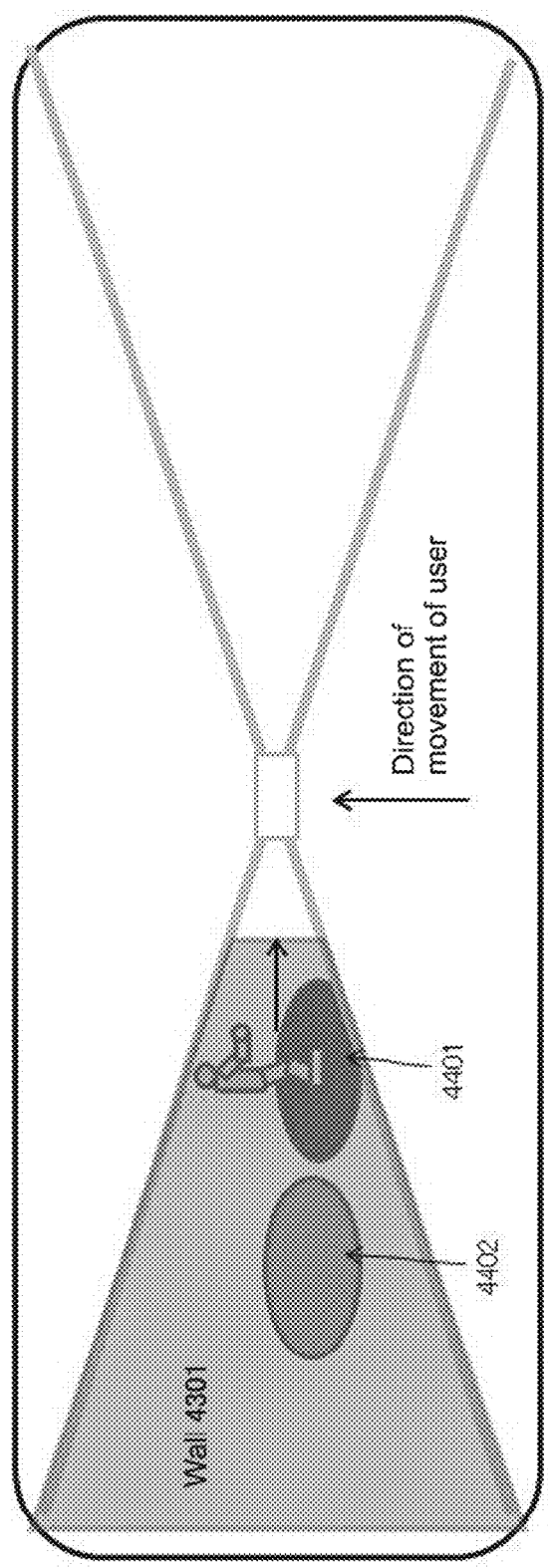
FIG. 44 is a diagram showing a display example in Example 7.

FIG. 44 shows an example in which a quantity of sunlight light 4401 and mechanical vibrations 4402 that are obtained by converting the power generation amount of the power generation apparatus 4320 beyond the wall 4310 are visualized. For example, the image display apparatus 4310 displays the power generation amount of the power generation apparatus 4320 on the left and right display units 4311 and 4312. If the image display apparatus 4310 is a see-through type head-mounted display, the power generation amount thereof is subjected to space mapping and displayed on the location where the power generation apparatus 4320 is installed. Thus, distribution of the secondary batteries charged in the real world can be visualized. Through such a displayed image, the user can know at a glance where the sufficiently charged secondary battery is.

If the power generation apparatus 4320 performs not sunlight power generation but vibration power generation, it indicates that the moving object moving in a location too dark to see is present. For example, if such a power generation apparatus 4320 is being moved to the user from the back of the wall 4301, the moving object on which the power generation apparatus 4320 is installed approaches, which is dangerous. Thus, from the displayed image of the second information as shown in FIG. 44, the user can perceive the approach of danger.

The image display apparatus 4310 can derive, from the second information as shown in FIG. 44, the third information such as the control information for controlling the image display apparatus 4310 itself or the external device.

The image display apparatus 4310 may upload the second information as shown in FIG. 44 into the server on the Internet (not shown) (including posting to an information providing site) or transmit it to information terminals of other users through direct communication such that it can be shared between the users. By the server collecting the second information pieces, it is possible to further derive and use the third information such as traffic information or a log of accidents.

By displaying the displayed image shown in FIG. 44 also on the external display unit 515, the image display apparatus 4310 can present the information also to people around the user.

Example 8

By analyzing a log of power generation amounts for all the day or a log of power generation amounts for each predetermined period of the power generation apparatus installed on the body of the user or the power generation apparatus installed in the surrounding environment of the user, the image display apparatus can provide the action-inducing information for inducing the user to take an action, for example, alarming based on a transition of the power generation amount at each time. As the method of providing the information, a method of displaying an image such as an alarming image on the display unit 509 and a presentation using sounds are exemplified.

Figure 45:
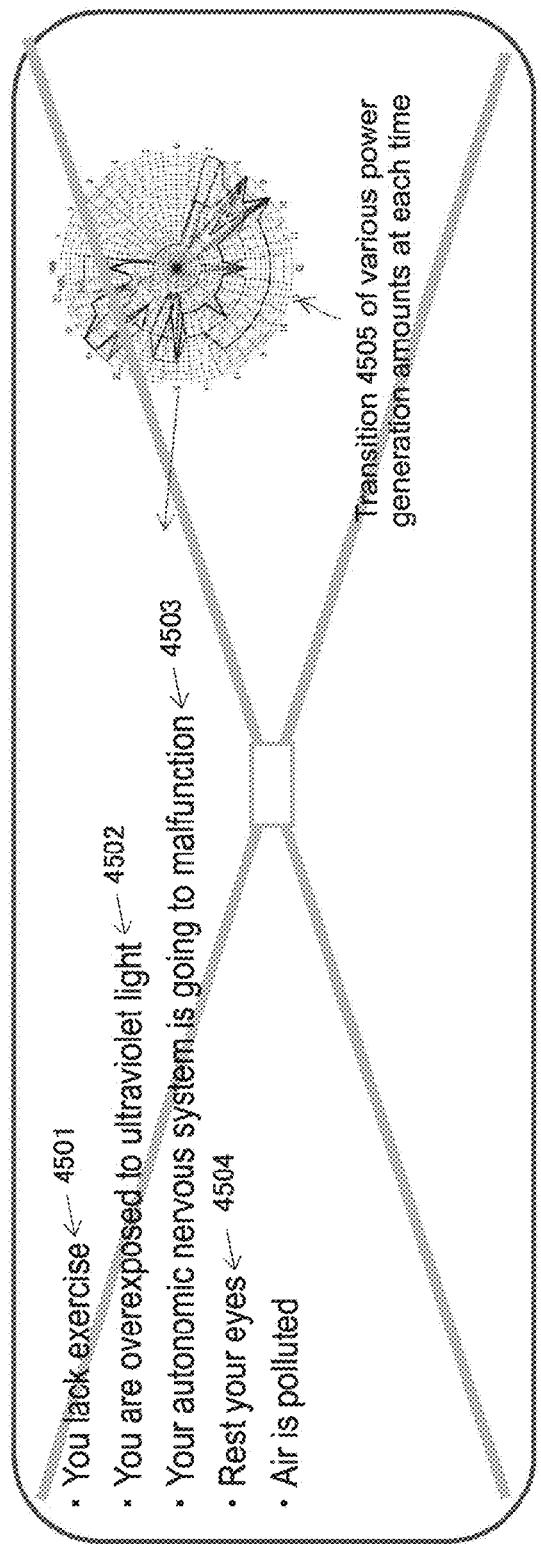
FIG. 45 is a diagram showing a configuration example of a screen that presents action-inducing information to the user.

Depending on the type of the power generation element used as the power generation unit, the second information that can be obtained by converting the first information such as the power generation amount on the side of the image display apparatus 710 and the third information such as the action-inducing information that is derived from the second information vary. Relationships between types of the power generation element and derived action-inducing information are shown in Table 1 below. In addition, a configuration example of the screen that presents the action-inducing information to the user is shown in FIG. 45.

TABLE 1

| Power generation element | Action-inducing information | Display example |
| --- | --- | --- |
| Vibration power generation | Lack of exercise | You lack exercise |
| Ultraviolet-ray power generation | Skin care | You are overexposed to ultraviolet light |
| Temperature-difference power generation | Autonomic nervous system | Your autonomic nervous system is going to malfunction |
| Radio-wave power generation | VDT work | Rest your eyes |

With a vibration power generation element that generates electrical power using vibrations, the first information such as the power generation amount can be converted into the second information such as the amount of exercise of the user and the health state of the user can be monitored. When the power generation amount is lowered, it can be judged that the amount of exercise of the user is insufficient. Therefore, action-inducing information that encourages the user to perform an exercise, for example, saying "You lack exercise." indicated by a reference number 4501 as the third information, can be generated as the third information.

With a thermoelectric conversion element that induces electrical power using a temperature difference or an enzymatic cell that generates electrical power using sweat of the user, the health state of the user can be monitored by converting the first information such as its power generation amount into the second information such as a body temperature of the user. When the power generation amount increases, there is a fear that it affects the health of the user. Therefore, action-inducing information for attracting the attention of the user to an autonomic nervous system or chronic disease (backache, etc.), for example, saying "Your autonomic nervous system is going to malfunction" indicated by a reference number 4503 as the third information, can be generated as the third information.

With a power generation element that induces electrical power by mainly using environmental energy such as a solar-cell power generation element, an ultraviolet-ray power generation element, an infrared-ray power generation element, a radio-wave power generation element, a power generation element using an ion concentration difference, and a power generation element that generates electrical power using radial rays, an environment in a location where the user is located can be monitored by converting the first information such as its power generation amount into the second information such as sunlight (ultraviolet rays) and radio waves with which the user is irradiated. When the power generation amount increases, there is a fear that it affects the health of the user. Therefore, action-inducing information for attracting the attention to the environment can be generated as the third information. For example, when the power generation amount based on sunlight (ultraviolet rays) increases, action-inducing information for attracting the attention to skin care, for example, saying "You are overexposed to ultraviolet light" indicated by a reference number 4502 can be generated by the third information. When the power generation amount based on radio waves increases, it is likely that the user is performing a work with a heavy load, for example, the user is located near an electronic apparatus while facing a VDT (Video Display Terminal). Therefore, action-inducing information for urging the user to rest his/her eyes, for example, saying "Rest your eyes" indicated by a reference number 4504 can be generated as the third information.

The image display apparatus 710 can upload the second information available for health care or medicine or pathology as described above into the server on the Internet (not shown) (including posting to an information providing site) or transmit it to information terminals of other users through direct communication such that it can be shared between the users. The image display apparatus 710 can also generate, based on the second information, control information for controlling the image display apparatus 710 itself or the external device (control information for sunscreen, air conditioner, display device, or the like).

Figure 46:
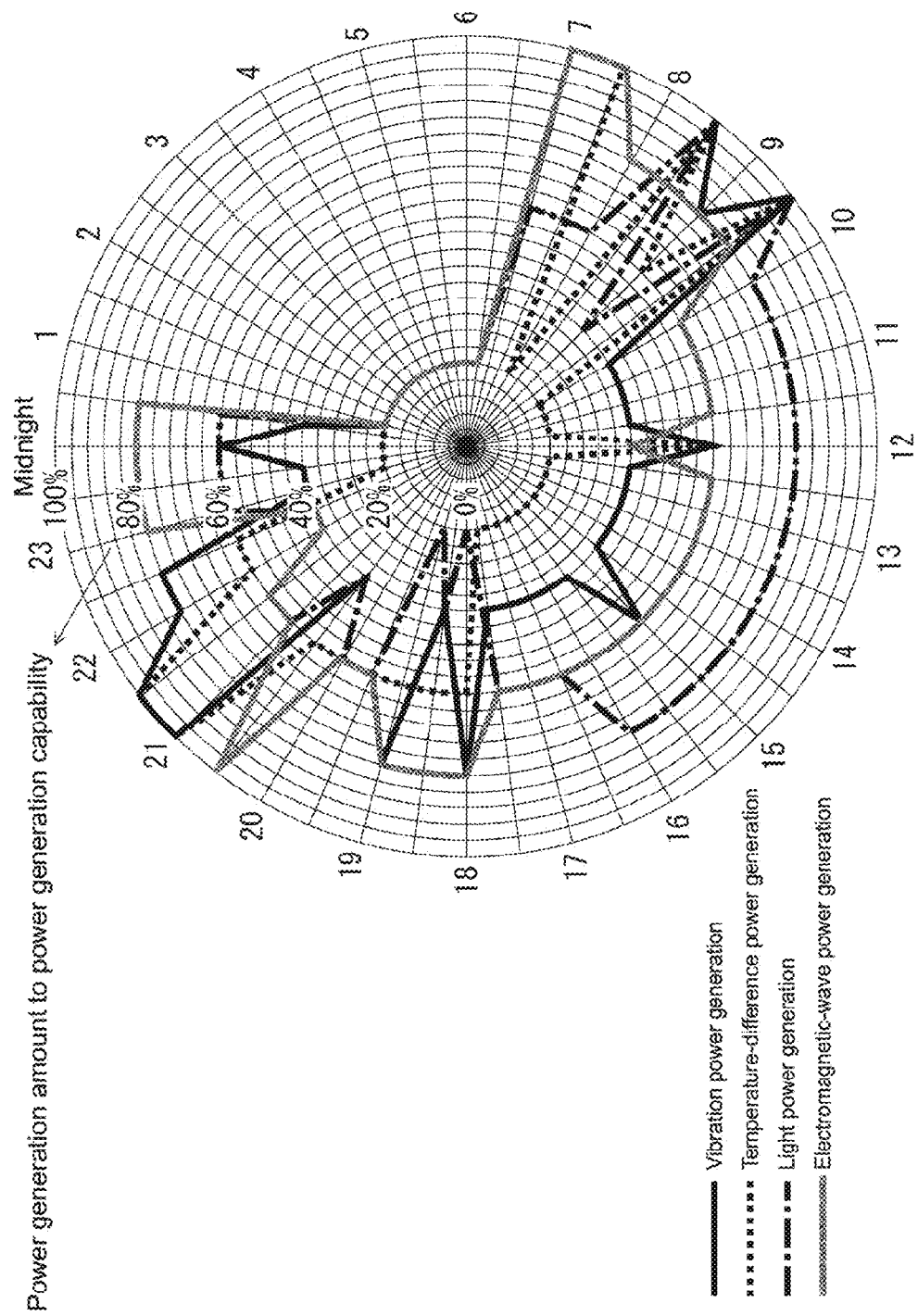
FIG. 46 is a diagram showing a transition 4505 of a power generation amount of each of various power generation elements at each time, which is first information, in an enlarged state.
Figure 47:
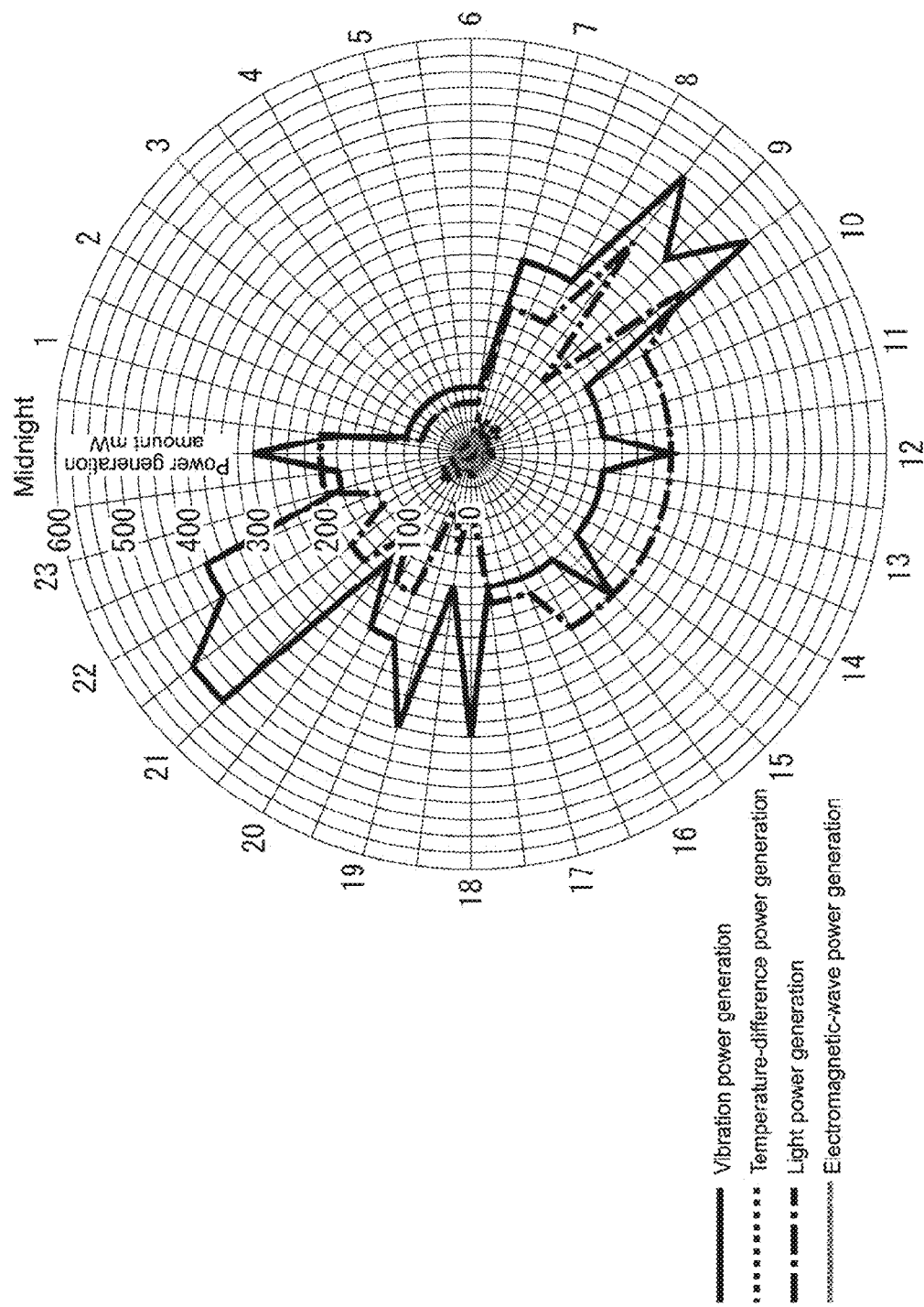
FIG. 47 is a diagram showing the transition 4505 of the power generation amount of each of the various power generation elements at each time, which is the first information, in an enlarged state.

Note that, in the screen that presents the action-inducing information to the user, which is shown in FIG. 45, the first information 4505 such as a transition of power generation amounts at each time of the various power generation elements may be displayed together with the action-inducing information 4501 to 4504 derived from power generation amounts or the like of various power generation elements. In FIG. 45, the transition 4505 of the power generation amounts at each time of the various power generation elements is small and difficult to see, and hence shown in FIGS. 46 and 47 in an enlarged state. Both the graphs shown in FIGS. 46 and 47 indicate the power generation amount in a radial direction and a time in a circumferential direction. It should be noted that FIG. 46 indicates the power generation amount by a ratio of each power generation element to a capability and FIG. 47 indicates the power generation amount by an absolute value [mW].

In addition to presenting these action-inducing information pieces to the user of the image display apparatus, the action-inducing information pieces of the image display apparatuses may be computerized by the server or the like and shared among a plurality of users. In the server, a result of collecting alarming information pieces can also be used for health care or medicine or pathology.

Example 9

A monitoring system according to Example 9 includes power generation apparatuses that are installed on a user, a player, judge, or spectator other than the user, and an environment such as a playing field especially in a competition such as a sport, and monitors the user, the player other than the user, and the environment where the competition takes places.

The monitoring system according to this example is formed of an image display apparatus (head-mounted display) that is used by being mounted on the head or face of the user who mainly performs or views the competition such as the sport and one or more power generation apparatuses.

In this example, the installation location of the power generation apparatus is various. An example of the installation location of the power generation apparatus is a body of a person such as the user or the player, judge, and spectator other than the user. The power generation apparatus is installed in a wrist, neck, ankle, or the like. Another example of the installation location of the power generation apparatus is a tool used in the competition. Specifically, examples thereof can include a shoe, a ball, a racket, a bat, a golf club, a bicycle, a ski, a snow board, various protectors, a bamboo sword, a weapon used in fencing (fleuret, epee, saber), an oar, a kayak, a surfboard, and a sailing board. Still another example of the installation location of the power generation apparatus is a building such as a playing field or an installation in the building. Specifically, examples thereof can include a wall of a tennis court, a goal or goal net of a soccer, a basketball hoop, a golf tee pin, cup, or flag, and a field in a court of each competition.

The power generation apparatus includes a power generation unit, a storage element, and a communication unit. The power generation unit is formed of a vibration power generation element that generates electrical power using vibrations (electrostatic type, electromagnetic type, inverse-magnetostrictive type, or piezoelectric type), a thermoelectric conversion element that generates electrical power using a temperature difference, an enzymatic cell that generates electrical power using sweat, a power generation element using an ion concentration difference, a solar-cell power generation element, an ultraviolet-ray power generation element, an infrared-ray power generation element, and the like. Depending on the installation location of the power generation apparatus, one or a combination of two or more of them are used. The storage element is formed of, for example, a capacitor, a secondary battery, a spring, and a heat storage material. The storage element stores electrical power generated by the power generation unit or stores it as energy. The communication unit transmits the first information including the power generation amount and the power storage amount of the power generation unit to the image display apparatus. The communication unit can use a communication means such as wireless communication such as Wi-Fi and human body communication through the medium of the body of the user or the wired communication (including signal transmission through an electroconductive fiber). The communication unit may be constantly operated and transfer the first information in real time or may be intermittently operated and transfer the first information.

When the image display apparatus receives the first information such as the power generation amount from the power generation apparatus, based on the principle of the power generation unit for inducing electrical power, the first information is converted into the second information on the sport being played and presented to the user. The above-mentioned first information received from the power generation apparatus can be converted into the second information such as an amount of exercise of the user or person other than the user, force acting on the user or other matter, an acceleration, a frequency, an environmental temperature, a basal metabolism rate, a stress (mental strain), and an amount of solar radiation. By viewing or listening to the converted second information, the user can monitor a person such as the user itself that is the player, a player other than the user, the judge, and the spectator and the environment in which the competition takes place.

The power generation apparatus installed on the user or person other than the user uses a vibration power generation element that generates electrical power using vibrations, a thermoelectric conversion element that generates electrical power using a temperature difference, an enzymatic cell that generates electrical power using sweat, or the like as the power generation unit.

For example, if the user on which the power generation apparatus is installed is the player or the person other than the user is a member of the same team or an opponent, on the side of the image display apparatus, from the first information such as the power generation amount that is received from such an power generation apparatus and the second information obtained by converting the first information, the state of the player such as condition and tension of the player and a gravity balance of the body in the competition can be derived as the third information.

If the user or person other than the user on which the power generation apparatus is installed is the spectator of the competition, on the side of the image display apparatus, from the first information such as the power generation amount that is received from such an power generation apparatus and the second information obtained by converting the first information, the state of the competition such as a degree of excitement of the competition can be derived as the third information.

If the user or person other than the user on which the power generation apparatus is installed is the judge of the competition, on the side of the image display apparatus, from the first information such as the power generation amount that is received from such an power generation apparatus and the second information obtained by converting the first information, information on the player having a health problem, problems of tool and facility used for the competition, fact-checking information on the proceeding of the competition (scores, for example, the ball in the goal, against rules, for example, the ball over the touchline, etc.), or the environment of the playing field, such as weather, wind velocity, and water velocity, can be derived as the third information.

If the user is a spectator, the image display apparatus converts the first information such as the power generation amount that is received from the power generation apparatus installed on the player or judge into the above-mentioned second information and displays it. With this, the user can monitor the player and the environment such as the playing field in the sport competition. Further, the image display apparatus can derive, based on a difference from past second information or current second information on the player, control information for controlling the image display apparatus itself or the external device as the third information. For example, in the image display apparatus or game console, the control information for controlling a character or the like of the player when a game of the same event as the viewed competition may be derived as the third information and information obtained from a real competition may be reflected on the game.

The power generation apparatus installed in the tool used in the competition uses a vibration power generation element that generates electrical power using vibrations (electrostatic type, electromagnetic type, inverse-magnetostrictive type, or piezoelectric type), a thermoelectric conversion element that generates electrical power using a temperature difference, a power generation element using an ion concentration difference, a solar-cell power generation element, an ultraviolet-ray power generation element, an infrared-ray power generation element, or the like as the power generation unit. On the side of the image display apparatus, the first information such as the power generation amount that is received from such a power generation apparatus, a gravity balance of the body of the player, an amount of exercise of the user using the tool, force acting on the user or tool, an acceleration, a frequency, an environmental temperature, a basal metabolism rate, a sweat rate, a stress (mental strain), an impact force or acceleration added to the tool used for the competition, a ball speed, an impact force in the impact, or a physical quantity such as an amount of solar radiation can be converted as the second information. Further, from the second information obtained by converting the first information, condition and tension of the player, problems of tool used for the competition, fact-checking information on the proceeding of the competition, and the like can be derived as the third information.

The power generation apparatus installed in a building such as the playing field or the facility in the building uses a vibration power generation element that generates electrical power using vibrations (electrostatic type, electromagnetic type, inverse-magnetostrictive type, or piezoelectric type), a thermoelectric conversion element that generates electrical power using a temperature difference, a power generation element using an ion concentration difference, a solar-cell power generation element, an ultraviolet-ray power generation element, an infrared-ray power generation element, or the like as the power generation unit. On the side of the image display apparatus, from the first information such as the power generation amount that is received from such an power generation apparatus and the second information obtained by converting the first information, fact-checking information on the proceeding of the competition (scores, for example, the ball in the goal, against rules, for example, the ball over the touchline, etc.), problems of the competition facility, a degree of excitement of the competition, or the environment of the playing field, such as weather, wind velocity, and water velocity, can be derived as the third information.

Figure 48:
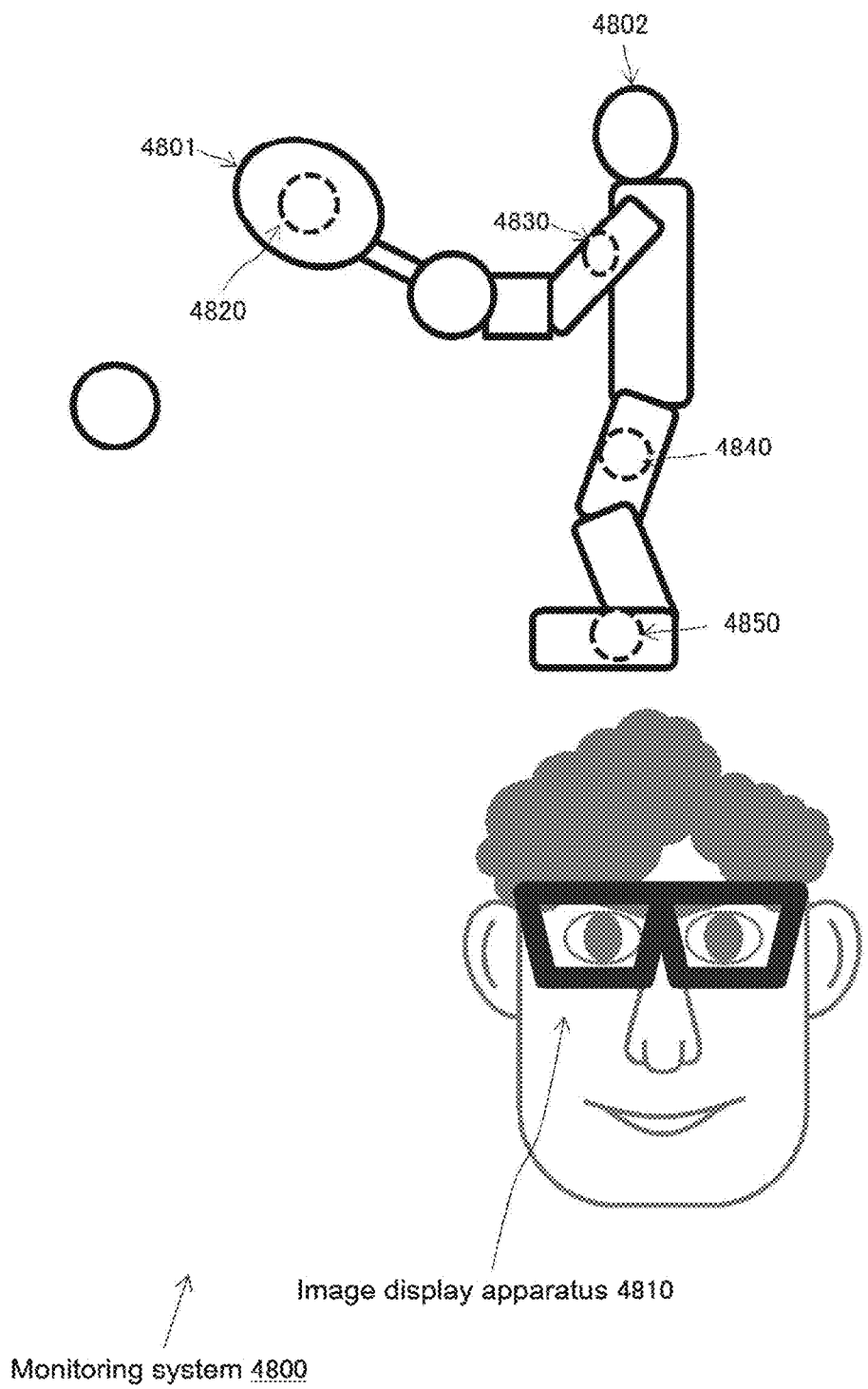
FIG. 48 is a diagram schematically showing a configuration of a monitoring system 4800 according to Example 9.

FIG. 48 schematically shows a configuration of a monitoring system 4800 according to Example 9. The monitoring system 4800 shown in the figure assumes a case where the user is viewing a tennis game. The monitoring system 4800 is formed of an image display apparatus (head-mounted display) 4810 that is used by being mounted on the head or face of the user, a power generation apparatus 4820 installed in a tennis racket 4801, and power generation apparatuses 4830, 4840, 4850 . . . installed in a plurality of points of the body of a tennis player 4802. Although not shown in the figure, each of the power generation apparatuses 4820, 4830, 4840, 4850 . . . includes a power generation unit, a power storage unit, and a communication unit. The monitoring system 4800 basically has the functional configuration shown in FIG. 6. However, in FIG. 48, the system 4800 is shown in an abstract manner as it is operated.

The power generation apparatus 4820 installed in the tennis racket 4801 uses, for example, a vibration power generation element that generates electrical power using vibrations (electrostatic type, electromagnetic type, inverse-magnetostrictive type, or piezoelectric type) as the power generation unit. The power generation apparatuses 4830, 4840, 4850 . . . installed on the body of the tennis player 4802 use a vibration power generation element that generates electrical power using vibrations (electrostatic type, electromagnetic type, inverse-magnetostrictive type, or piezoelectric type), a thermoelectric conversion element that generates electrical power using a temperature difference, an enzymatic cell that generates electrical power using sweat, an solar-cell power generation element, an ultraviolet-ray power generation element, an infrared-ray power generation element, or the like as the power generation unit. Each of the power generation apparatuses 4820, 4830, 4840, 4850 . . . transmits the first information such as the power generation amount and the power storage amount to an image display apparatus 4810.

On the side of the image display apparatus 4810, the first information such as the power generation amount that is received from the power generation apparatus 4820 installed in the tennis racket 4801 is converted into the second information formed of a counterforce, acceleration, or frequency acting on a racket 4801 hitting back the ball and a physical quantity such as a ball speed of the hit-back ball and an impact force in the impact. If the obtained second information is subjected to space mapping and displayed on the screen so as to be superimposed on the location where the power generation apparatus 4820 is installed, the user can monitor it. Additionally, the third information indicating a problem such as breakage of the tennis racket 4801 may be derived from the second information and displayed on the screen.

On the side of the image display apparatus 4810, based on the first information such as the power generation amount that is received from the power generation apparatuses 4830, 4840, 4850 . . . installed on the body of the tennis player 4802, conversion into the second information such as an amount of exercise of the tennis player 4802 or a change thereof, a weight balance of the body or a change thereof, a basal metabolism rate or a change thereof, and a sweat rate or a change thereof is performed. If the obtained second information is subjected to space mapping and displayed on the screen so as to be superimposed on the location where the power generation apparatus 4820 is installed, the user can monitor it. Additionally, the condition or stress (mental strain) of the tennis player 4802 or the like may be derived from the second information as the third information and displayed on the screen.

For example, if the power generation apparatuses 4820, 4830, 4840, 4850 . . . include a vibration power generation element that generates electrical power using vibrations as the power generation unit, the power generation amount increases when a strong force is applied. Thus, on the side of the image display apparatus 4810, based on the received power generation amount, force acting on the location where each of the power generation apparatuses 4820, 4830, 4840, 4850 . . . is installed can be converted as the second information. In particular, the power generation amount of the power generation apparatus 4820 installed in the racket 4801 can be converted into an impact force applied on the racket 4801 or the ball as the second information. A power storage amount for all the day of the power storage unit is proportional to an amount of exercise after the tennis player 4802 wakes up, and can be converted into a calorie consumption as the second information.

Figure 49:
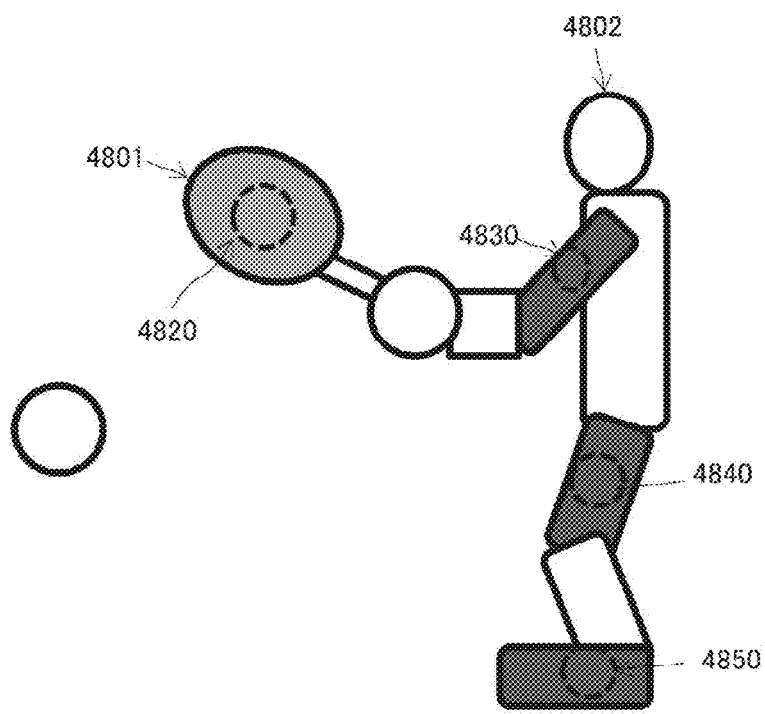
FIG. 49 is a diagram showing a display example of a screen of an image display apparatus 4810 in the monitoring system 4800 according to Example 9.

FIG. 49 shows an example in which, in the monitoring system 4800 according to this example, the image display apparatus 4800 performs space mapping on the second information obtained by converting the first information of the power generation amount, the power storage amount, and the like of each of the power generation apparatuses 4820, 4830, 4840, 4850 . . . and displays it. In the example shown in the figure, by indicating the installation location of the power generation apparatus having a larger power generation amount or power storage amount by darker shading, application of a larger force (converted as the second information) is expressed.

The power storage amount in the power storage unit is a power storage amount stored up to this point (e.g., a period after the power generation apparatus is installed) and can also indicate how much the corresponding site on which the power generation apparatus is installed has been used for the play. A site on which the power generation apparatus is installed, which has a large power storage amount, can be estimated as a site used many times, in other words, an exhausted site. If force above a certain level is applied on the exhausted site, injury occurs easily. In view of this, by using a combination of the power storage amount and the power generation amount, the image display apparatus 4810 may derive the easiness of occurrence of injury in each site of the body of the tennis player 4802, as the third information. If the power generation amount increases and a strong force is applied on the exhausted site having a large power storage amount, warning for avoiding injury may be performed by blinking a light at this site.

After presenting the displayed image as shown in FIG. 49 to the user, the image display apparatus 4810 can upload it into the server on the Internet (not shown) (including posting to an information providing site) or transmit it to information terminals of other users through direct communication such that the amount of exercise and fatigue of the tennis player 4802 and other information for monitoring the game can be shared between the users and used as a log of sport data.

According to the monitoring system 4800 of this example, the second information such as the amount of exercise and gravity balance of the player of the sport that is out of a perception range for the user wearing the image display apparatus 4810 or difficult to perceive can be converted based on the first information such as the power generation amount that is obtained on the side of each of the power generation apparatuses 4820 to 4850. In addition, the third information such as the degree of fatigue can be derived and presented to the user. On the side of the image display apparatus 4810, the perception range of the user can be extended by arranging and presenting information pieces obtained from the power generation apparatuses 4820 to 4850.

Note that a method of additionally providing each of the power generation apparatuses 4820 to 4850 with a pressure sensor, a temperature sensor, or the like, to thereby directly measure the second information such as the impact added to the racket 4801 and the amount of exercise of the tennis player 4802 is also conceivable. However, with such sensors, the component cost of the power generation apparatuses 4820 to 4850 increases and the power consumption of the power generation apparatuses 4820 to 4850 also increases. As a result, the continuous use time is inevitably shortened. In contrast, as in this example, according to the method of transmitting the first information such as the power generation amounts from the power generation apparatuses 4820 to 4850 and converting the first information received on the side of the image display apparatus 4810 into the second information on the viewed game, such as the impact force added to the racket 4801 and the amount of exercise of the tennis player 4802, the apparatus cost can be reduced. In addition, the power generation unit itself in each of the power generation apparatuses 4820 to 4850 serves as the sensing device and a power-supply does not have to be provided. Therefore, the power consumption of the entire system 4800 is reduced. The limitation on the continuous use time is overcome and the power generation apparatuses 4820 to 4850 do not have to be increased in size for the batteries.

Example 10

A monitoring system according to Example 10 monitors the user and the environment based on the information from the power generation apparatus and positively uses it for controlling the image display apparatus itself or the external device. Specifically, based on the first information such as the power generation amount transmitted from the power generation apparatus or the second information converted from the first information, control information for a character that appears in a game program executed by the image display apparatus itself or game console is derived.

The monitoring system according to this example is formed of an image display apparatus (head-mounted display) that is used by being mounted on the head or face of the user and one or more power generation apparatuses. The power generation apparatus is installed on, for example, a user or target viewed by the user, a tool used by the user or target viewed by the user, or a building that is a place for the user or target viewed by the user.

The power generation apparatus includes a power generation unit, a storage element, and a communication unit. The power generation unit includes a vibration power generation element that generates electrical power using vibrations (electrostatic type, electromagnetic type, inverse-magnetostrictive type, or piezoelectric type), a thermoelectric conversion element that generates electrical power using a temperature difference, an enzymatic cell that generates electrical power using sweat, a power generation element using an ion concentration difference, a solar-cell power generation element, an ultraviolet-ray power generation element, an infrared-ray power generation element, and the like. Depending on the installation location of the power generation apparatus, one or a combination of two or more of them are used. The storage element is formed of, for example, a capacitor, a secondary battery, a spring, and a heat storage material. The storage element stores electrical power generated by the power generation unit or stores it as energy. The communication unit transmits the first information including the power generation amount and the power storage amount of the power generation unit to the image display apparatus. The communication unit can use a communication means such as wireless communication such as Wi-Fi and human body communication through the medium of the body of the user or the wired communication (including signal transmission through an electroconductive fiber). The communication unit may be constantly operated and transfer the first information in real time or may be intermittently operated and transfer the first information.

When the image display apparatus receives the first information such as the power generation amount from the power generation apparatus, based on the principle of the power generation unit for inducing electrical power, the first information is converted into the second information for monitoring the user or target viewed by the user, the tool used by the user or target viewed by the user, the building that is the place for the user or target viewed by the user, or the like, in which the power generation apparatus is installed.

In addition, based on the second information, control information for controlling status and attribute of the game character, a feature amount of an item or the like possessed by the character, and the like is derived. Processing of calculating the control information may be performed by the image display apparatus itself or may be performed in the game console or server connected to the image display apparatus over a network.

According to the control information for the character, the condition of the real world that the user monitors can be reflected on the status and attribute of the character or the feature amount of the item possessed by the character and the thus obtained virtual world can be displayed. The character generated on the side of the game console may be displayed on the image display apparatus. For example, if the image display apparatus is a see-through type head-mounted display, the virtual image may be combined with the real image observed in a see-through manner and it may be displayed in an exaggerated manner according to the derived status and attribute or feature amount. If the target viewed by the user is a player of a sport viewed by the user, an image or an attribute image derived in the above-mentioned manner may be added to the real image and the reality may be displayed in an exaggerated manner like an animation or game.

For example, if the power generation apparatus is installed on the user or target viewed by the user, a power generation unit such as a vibration power generation element that generates electrical power using vibrations, a radio-wave power generation element that induces electrical power using radio waves (far electromagnetic field), a thermoelectric conversion element that generates electrical power using a temperature difference, or an enzymatic cell that generates electrical power using sweat is used as the power generation unit. The first information such as the power generation amount can be converted into the second information such as an amount of exercise, a basal metabolism rate, and a stress (mental strain) of that person.

If the power generation apparatus is installed in the tool used by the user or target viewed by the user, a vibration power generation element that generates electrical power using vibrations (electrostatic type, electromagnetic type, inverse-magnetostrictive type, or piezoelectric type), a thermoelectric conversion element that generates electrical power using a temperature difference, a power generation element using an ion concentration difference, a solar-cell power generation element, an ultraviolet-ray power generation element, an infrared-ray power generation element, a radio-wave power generation element that induces electrical power using radio waves (far electromagnetic field), or the like is used as the power generation unit. The first information such as the power generation amount can be converted into the second information such as an amount of exercise, force acting on a tool, an acceleration, a frequency, an environmental temperature, a basal metabolism rate, a sweat rate, a stress (mental strain), an impact force or acceleration added to a tool used for a competition, and an amount of solar radiation.

If the power generation apparatus is installed in the building that is the place for the user or target viewed by the user, a vibration power generation element that generates electrical power using vibrations (electrostatic type, electromagnetic type, inverse-magnetostrictive type, or piezoelectric type), a thermoelectric conversion element that generates electrical power using a temperature difference, a power generation element using an ion concentration difference, a solar-cell power generation element, an ultraviolet-ray power generation element, an infrared-ray power generation element, a radio-wave power generation element that induces electrical power using radio waves (far electromagnetic field), or the like is used as the power generation unit. On the side of the image display apparatus, the first information such as the power generation amount can be converted into the second information such as the impact added to the building and the amount of solar radiation.

For example, when the amount of exercise or the basal metabolism rate converted from the power generation amount of the power generation apparatus installed on the user or target viewed by the user or the tool used by the user or target viewed by the user is large, control information for adding a strong image or physical attribute image to the corresponding character is derived. Based on such control information, the image display apparatus displays the character in a muscular state or displays the character as a soldier. A virtual image for showing a person viewed by the user in the real image in a muscular state or providing the person with a tool such as arms may be combined.

When a heat generation amount or sweat rate converted from the power generation amount of the power generation apparatus installed on the user or target viewed by the user or the tool used by the user or target viewed by the user is high, control information for adding a mental image or water attribute image to the corresponding character is derived.

If the amount of solar radiation converted from the power generation amount of the power generation apparatus installed in the tool used by the user or target viewed by the user or the building that is the place for the user or target viewed by the user is large, control information for adding a holy attribute image to the corresponding character is derived.

If the radio-wave intensity converted from the power generation amount of the power generation apparatus installed on the user or target viewed by the user, the tool used by the user or target viewed by the user, or the building that is the place for the user or target viewed by the user is high, control information for adding a light image to the corresponding character is derived.

When the speed, acceleration, or impact force converted from the power generation amount of the power generation apparatus installed in the tool used by the user or target viewed by the user is high, control information for adding an image expressing that the tool in the real world or the corresponding character moves quickly or a strong force is added or an attribute image to the corresponding character is derived.

Figure 50:
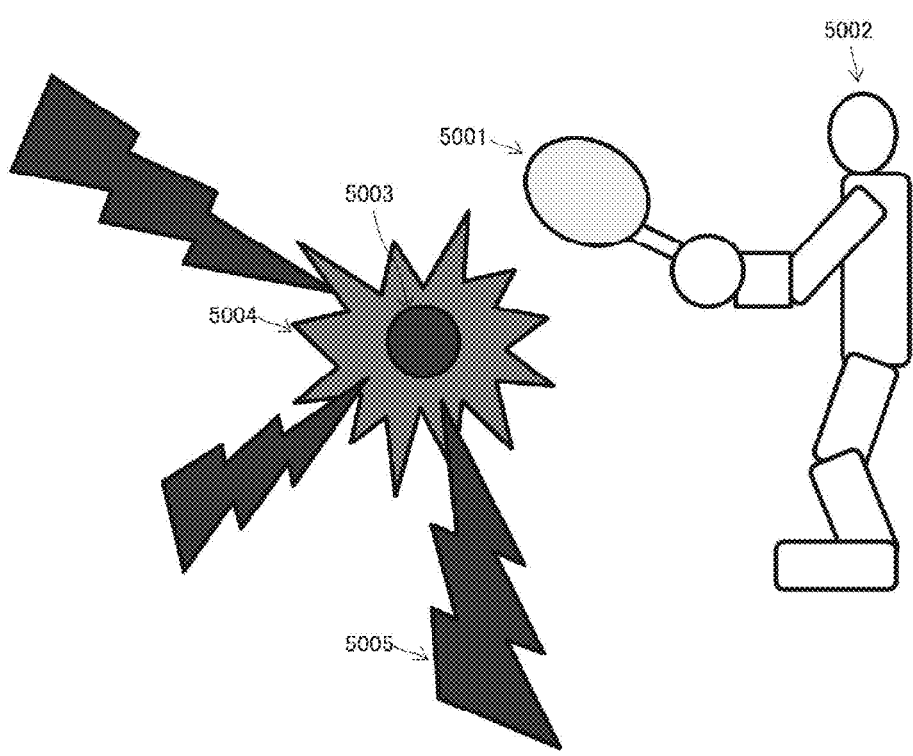
FIG. 50 is a diagram showing a display example of a screen of an image display apparatus in Example 10.

FIG. 50 shows a display example in which the virtual image expressing an image obtained based on the power generation amount is combined with the real image. In the example shown in the figure, it is assumed that the user is viewing a tennis game and a power generation apparatus is installed in a racket 5001 gripped by a tennis player 5002. The image display apparatus can convert the first information such as the power generation amount transmitted from the power generation apparatus into the second information such as the speed or acceleration when the tennis player 5002 swings the racket 5001 and the impact force added when hitting back a ball 5003. The image display apparatus derives, from the second information, control information for adding an image expressing the speed at which the tennis player 5002 swings the racket 5001, the impact force added to the racket 5001 in the impact when hitting back the ball 5003, or the speed of the hit back ball 5003. In the example shown in FIG. 50, a virtual image with a fireball 5004 or lighting 5005 is combined with the real image of the tennis game viewed by the user according to the speed of the hit back ball 5003.

The image display apparatus can upload the control information for adding an image to the character in the game or the observed real image into the server on the Internet (not shown) (including posting to an information providing site) or transmit it to information terminals of other users through direct communication such that it can be shared between the users and used as the log of sport data.

As discussed above, according to the technology disclosed herein, the image display apparatus includes means for obtaining information on a power storage amount, a power generation amount, and the like of a secondary battery in one or more power generation apparatuses provided outside this apparatus. Thus, the user of the image display apparatus can check the power storage amount of the secondary battery in the power generation apparatus without stopping the use of the image display apparatus. For example, when a power storage amount of a battery in use is lowered, the user can properly judge with which of the power generation apparatuses the user should replace the battery.

According to the technology disclosed herein, the image display apparatus displays the image in combination with the information generated from the power generation amounts of the power generation apparatuses, and hence the user can know at a glance various types of information in the real world.

Patent Document 1: Japanese Patent Application Laid-open No. 2008-301606

Patent Document 2: Japanese Patent Application Laid-open No. 2007-330034

Patent Document 3: Japanese Patent Application Laid-open No. 2011-2753

Patent Document 4: Japanese Patent Application Laid-open No. 2010-15886

Patent Document 5: Japanese Patent Application Laid-open No. 2008-304268

INDUSTRIAL APPLICABILITY

Hereinabove, the technology disclosed in this specification has been described in detail with reference to the specific embodiments. However, it is obvious that the embodiments can be modified or substituted by a person having ordinary skill in the art without departing from the gist of the technology disclosed herein.

The image display apparatuses each used by being mounted on the head or face of a user can be classified into a light-shielding type and a transmissive type. The technology disclosed herein can be applied to either one of those types. Additionally, the image display apparatuses of those types can be classified into a binocular type including display units for the left and right eyes and a monocular type including a display unit for either one of the left and right eyes. The technology disclosed herein can be applied to either one of the types. As a matter of course, also if the technology disclosed herein is applied to an image display apparatus of a type that is not mounted on the head or face of the user (e.g., cellular phone such as smart phone, tablet terminal, electronic book, or portable music player), the user can similarly monitor the power storage amount of the secondary battery and the power generation amount of the power generation apparatus.

In short, the technology disclosed herein has been described as an example, and the content described in this specification should not be construed in a limited way. In order to determine the gist of the technology disclosed herein, the scope of claims should be considered.

Note that the technology disclosed in this specification may also take the following configurations.

(1) A image display apparatus that is mounted on a head or face, including:

an image display unit that displays an image;

an information input unit that inputs information from a power generation apparatus; and a control unit that controls the image display unit based on a result of processing the input information.

(2) The image display apparatus according to (1), in which the image display unit displays an image in a see-through manner, and the control unit causes the image display unit to display the result of processing the input information so as to be superimposed on the power generation apparatus in a field of view of a user.

(3) The image display apparatus according to (1), further including
a storage unit that stores a displayed image of the image display unit based on the input information or the result of processing the input image.
(4) The image display apparatus according to (1), further including
a communication unit that transmits a displayed image of the image display unit based on the input information or the result of processing the input image to an external device.
(5) The image display apparatus according to (1), in which
the control unit further controls an external device based on the result of processing the input information.
(6) The image display apparatus according to (1), further including
a second image display unit that displays an image to be visible also to a person not wearing the image display apparatus on a head or face in a location different from that of the image display unit, in which
the control unit controls the second image display unit based on the result of processing the input information.
(7) The image display apparatus according to (1), in which
the information input unit inputs, from a power generation apparatus installed in a mounting unit mounted on a site of a body of a user, information on a power generation amount depending on a physical exercise in the site, and
the control unit causes the image display unit to display a power generation amount obtained from the power generation apparatus or information on an amount of exercise or acceleration in the site that is converted from the power generation amount.
(8) The image display apparatus according to claim 1, in which
the information input unit inputs, from a power generation apparatus installed in a shoe worn on at least either one of left and right feet of a user, information on a power generation amount depending on an exercise of the foot.
(9) The image display apparatus according to (7) or (8), in which
the information input unit inputs information from each power generation apparatus through any of wireless signal transmission, signal transmission using human body communication, or signal transmission using an electroconductive fiber.
(10) The image display apparatus according to (8), in which
the control unit causes the image display unit to display information obtained from the power generation apparatus of the shoe of the left foot on a left-hand side thereof and causes the image display unit to display information obtained from the power generation apparatus of the shoe of the right foot on a right-hand side thereof.
(11) The image display apparatus according to (8), in which
the control unit converts information on the power generation amount that is input from the power generation apparatus into an amount of exercise or acceleration of the foot and causes the image display unit to display it.
(12) The image display apparatus according to (8), in which
the control unit converts information on the power generation amount that is input from the power generation apparatus into a deterioration state of the shoe and causes the image display unit to display it.
(13) The image display apparatus according to (8), in which
the control unit obtains a posture of a body of the user based on a difference between left and right power generation amounts input from the power generation apparatuses or results of converting information on the power generation amounts that are input from the power generation apparatuses into accelerations of the left and right feet.
(14) The image display apparatus according to (13), further including
an acceleration sensor, in which
the control unit obtains the posture of the body of the user based on a relative acceleration of the left and right feet to an acceleration of the head of the user that is detected by the acceleration sensor.
(15) The image display apparatus according to (13), in which
the control unit causes the image display unit to display an image expressing a deviation of the posture of the body of the user.
(16) The image display apparatus according to (13), in which
the power generation apparatus includes an actuator, and
the control unit controls the actuator of the power generation apparatus based on the obtained posture of the body of the user.
(17) The image display apparatus according to (16), in which
the power generation apparatus takes a power generation mode to perform power generation and an actuator mode to be operated as the actuator by power supply.
(18) The image display apparatus according to (17), in which
the control unit switches the modes of the power generation apparatus based on the obtained posture of the body of the user.
(19) The image display apparatus according to (17), in which
the power generation apparatus includes an electromagnetic induction power generation element that performs electromagnetic induction power generation and operates as an electromagnetic induction actuator by power supply, and
the control unit performs, based on the obtained posture of the body of the user, switching of duties of a period in which the electromagnetic induction power generation element performs electromagnetic induction power generation and a period in which the electromagnetic induction power generation element is operated as the electromagnetic induction actuator or switching of loads connected to the electromagnetic induction power generation element.
(20) The image display apparatus according to (17), in which
the power generation apparatus includes an electrostatic induction power generation element that performs electrostatic induction power generation and is operated as an electrostatic induction actuator by power supply, and
the control unit performs, based on the obtained posture of the body of the user, switching of duties of a period in which the electrostatic induction power generation element performs electrostatic induction power generation and a period in which the electrostatic induction power generation element is operated as the electrostatic induction actuator or switching of loads connected to the electrostatic induction power generation element.
(21) The image display apparatus according to (17), in which
the power generation apparatus includes a piezoelectric power generation element that performs piezoelectric power generation and is operated as a piezoelectric actuator by power supply, and
the control unit performs, based on the obtained posture of the body of the user, switching of duties of a period in which the piezoelectric power generation element performs piezoelectric power generation and a period in which the piezoelectric power generation element is operated as the piezoelectric actuator or switching of loads connected to the piezoelectric power generation element.

(22) The image display apparatus according to (17), in which the power generation apparatus includes an inverse-magnetostrictive power generation element that performs inverse-magnetostrictive power generation and is operated as a magnetostrictive actuator by power supply, and the control unit performs, based on the obtained posture of the body of the user, switching of duties of a period in which the inverse-magnetostrictive power generation element performs inverse-magnetostrictive power generation and a period in which the inverse-magnetostrictive power generation element is operated as the magnetostrictive actuator or switching of loads connected to the inverse-magnetostrictive power generation element.

(23) The image display apparatus according to (1), in which the information input unit inputs information on a power generation amount from each of a first power generation apparatus attached to a collar of a companion animal and a second power generation apparatus attached to a lead with which a user pulls the companion animal.

(24) The image display apparatus according to (23), in which the control unit converts information on the power generation amount input from the first power generation apparatus into an acceleration or metabolic rate of the companion animal and converts information on the power generation amount input from the second power generation apparatus into an acceleration or metabolic rate of the user, and converts results of conversion on the image display unit.

(25) The image display apparatus according to (23), in which the control unit controls an automatic feeder of the companion animal based on an amount of exercise or metabolic rate of the companion animal that is converted from the information on the power generation amount input from the first power generation apparatus.

(26) The image display apparatus according to (1), in which the information input unit inputs, from each of a plurality of power generation apparatuses installed in a surrounding environment of a user, information on a power generation amount depending on electromagnetic waves, radioactivity, or other environmental energy.

(27) The image display apparatus according to (26), in which the control unit causes the image display unit to display information on a power generation amount of each power generation apparatus or information on a physical quantity converted from the power generation amount in association with an installation location of the corresponding power generation apparatus.

(28) The image display apparatus according to (26), in which the image display unit displays an image in a see-through manner, and the control unit causes the image display unit to display information on a power generation amount of each power generation apparatus or information on a physical quantity converted from the power generation amount so as to be superimposed on an installation location of the corresponding power generation apparatus in a field of view of the user.

(29) The image display apparatus according to (26), in which each power generation apparatus generates electrical power using radio waves having a particular frequency, and the control unit controls, based on a power generation amount of each power generation apparatus, an external device such as a re-transmitting apparatus for radio waves.

(30) The image display apparatus according to (26), in which each power generation apparatus generates electrical power using hazardous electromagnetic waves (ultraviolet rays) or radial rays, and the control unit controls, based on a power generation amount of each power generation apparatus, an external device in operation of a sunshade of an arcade or a light-shielding facility of a building or house or the like.

(31) The image display apparatus according to (1), in which the information input unit inputs, from a power generation apparatus installed in a foot fin mounted on at least either one of left and right feet of a user during diving, information on a power generation amount depending on an amount of kick of the foot, and the control unit causes the image display unit to display information on the power generation amount of the power generation apparatus or an amount of exercise, acceleration, or water flow of the foot that is converted from the power generation amount.

(32) The image display apparatus according to (31), in which the information input unit inputs information from each power generation apparatus through wireless signal transmission, signal transmission using human body communication, or signal transmission using an electroconductive fiber.

(33) The image display apparatus according to (31), further including a water flow sensor, in which the control unit estimates a direction of movement of the user under water based on a water flow velocity detected by the water flow sensor and an amount of exercise of each of the left and right feet that is converted from the power generation amount of each power generation apparatus.

(34) The image display apparatus according to (33), in which the control unit calculates an amount of kick of each of left and right feet for modifying a direction of movement of the user who is swimming to an aiming direction and causes the image display unit to display the result of calculation.

(35) The image display apparatus according to (31), further including a water flow sensor, in which the control unit estimates flow strength and direction of the water flow based on a water flow velocity detected by the water flow sensor and a water flow amount converted from a power generation amount of each power generation apparatus.

(36) The image display apparatus according to (35), in which the image display unit displays an image in a see-through manner, and the control unit causes the image display unit to display the estimated flow strength and direction of the water flow so as to be superimposed on a field of view of the user.

(37) The image display apparatus according to (35), in which the control unit controls a rigidity of the foot fin based on the estimated flow strength and direction of the water flow.

(38) The image display apparatus according to (35), further including a second image display unit that is visible also to a person not wearing the image display apparatus on a head or face, in which the control unit causes the second image display unit to display the estimated flow strength and direction of the water flow.

(39) The image display apparatus according to (1), in which the information input unit inputs, from each of a plurality of power generation apparatuses installed in a surrounding environment of a user, information on a power generation amount depending on sunlight.

(40) The image display apparatus according to (39), in which the control unit causes the image display unit to display information on a power generation amount of each power generation apparatus, an amount of solar radiation that is converted from the power generation amount or information on a growth level of farm products that corresponds to an amount of solar radiation or a harvest period or harvest order of the farm products in association with an installation location of the corresponding power generation apparatus.

(41) The image display apparatus according to (40), in which the image display unit displays an image in a see-through manner, and the control unit causes the image display unit to display the amount of solar radiation, or the information on the growth level of the farm products that corresponds to the amount of solar radiation or a harvest period or harvest order of the farm products so as to be superimposed on an installation location of the corresponding power generation apparatus in a field of view of a user.

(42) The image display apparatus according to (40), in which the control unit controls, based on the amount of solar radiation, the growth level of the farm products that corresponds to the amount of solar radiation, an external device in control of time and frequency of sprinkling by a sprinkler and time and time and frequency of sprinkling of agrochemicals and fertilization, operation of a harvesting machine, and operation of a weeding/insecticidal machine, or the like.

(43) The image display apparatus according to (40), further including an imaging unit, in which the control unit compares the growth level of the farm products that is converted from the power generation amount with a real growth level obtained by performing image analysis on a captured image of the imaging unit to thereby diagnose a health state of the farm products.

(44) The image display apparatus according to (43), in which the control unit controls, based on the diagnosed health state, an external device in control of time and frequency of sprinkling by a sprinkler and time and frequency of sprinkling of agrochemicals and fertilization, operation of a harvesting machine, and operation of a weeding/insecticidal machine, or the like.

(45) The image display apparatus according to (1), in which the information input unit inputs, from each of a plurality of power generation apparatuses installed in a manufacturing line within a factory, information on a power generation amount corresponding to a temperature, information on a power generation amount corresponding to an impact (further, for example, information on a power generation amount corresponding to a pressure fluctuation), or information on a power generation amount corresponding to electromagnetic waves.

(46) The image display apparatus according to (45), in which the control unit causes the image display unit to display information on a power generation amount of each power generation apparatus or at least any of the temperature, vibrations (also including a pressure fluctuation), and electromagnetic waves converted from the power generation amount in association with an installation location of the corresponding power generation apparatus.

(47) The image display apparatus according to (46), in which the image display unit displays an image in a see-through manner, and the control unit causes the image display unit to display information on a power generation amount of each power generation apparatus or at least any of the temperature, vibrations (also including the pressure fluctuation), and electromagnetic waves converted from the power generation amount so as to be superimposed on the installation location of the corresponding power generation apparatus in a field of view of a user.

(48) The image display apparatus according to (45), in which the control unit detects a dangerous point based on at least any of the temperature, vibrations (also including the pressure fluctuation), and electromagnetic waves converted from the power generation amount or checks a point where energy loss is generated.

(49) An image display method in which an image is displayed by an image display apparatus of a type mounted on a head or face, the method including:

an information input step of inputting information from a power generation apparatus; and a control step of controlling an image to be displayed based on a result of processing the input information.

(50) A storage medium that stores a computer program described in a computer readable format to cause a computer to function as:

an image display unit that displays an image; an information input that inputs information from a power generation apparatus; and a control unit that controls the image display unit based on a result of processing the input information.

(51) A monitoring system, including:

a power generation apparatus that generates electrical power and transmits information on a power generation amount; and an image display apparatus that displays a result of processing information received from the power generation apparatus that is of a type mounted on a head or face.

(101) An image display apparatus, including:

an image display unit that displays an image; a communication unit that communicates with a power generation apparatus; and a control unit that obtains first information on power generation from the power generation apparatus via the communication unit, converts the first information into second information based on a principle of the power generation apparatus for inducing electrical power, and controls the image display unit.

(102) The image display apparatus according to 101, in which the image display unit is mounted on a head or face.

(103) The image display apparatus according to 101, in which the control unit controls the image display unit to combine a virtual image expressing at least either the first information or the second information with a real image showing the power generation apparatus and display the combined image.

(104) The image display apparatus according to 101, in which the control unit converts a power generation amount of the power generation apparatus included in the first information into the second information including a physical quantity used by the power generation apparatus for inducing electrical power.

(104-1) The image display apparatus according to 104, in which the power generation apparatus generates electrical power using a vibration power generation element that is installed on a person or animal other than the person and generates electrical power using vibrations (electrostatic type, electromagnetic type, inverse-magnetostrictive type, or piezoelectric type), and the control unit converts the power generation amount of the power generation apparatus into acceleration, force, and amount of exercise of the person or animal, which serves as the second information.

(104-2) The image display apparatus according to 104, in which the power generation apparatus generates electrical power using a solar-cell power generation element that generates electrical power using sunlight, an ultraviolet-ray power generation element that generates electrical power using ultraviolet rays, or an infrared-ray power generation element that generates electrical power infrared rays or an integrated amount thereof, and the control unit converts the power generation amount of the power generation apparatus into sunlight intensity, ultraviolet intensity, or infrared ray intensity in an installation location of the power generation apparatus, which serves as the second information.

(104-3) The image display apparatus according to 104, in which the power generation apparatus generates electrical power using a thermoelectric conversion element that generates electrical power using a temperature difference (including power generation using the Seebeck effect, the Thomson effect, or the like, power generation using a thermoelectric element or pyroelectric effect, thermomagnetic power generation, and the like), and the control unit converts the power generation amount of the power generation apparatus into temperature, heat flow rate, and heat amount in an installation location of the power generation apparatus, which serves as the second information.

(104-4) The image display apparatus according to 104, in which the power generation apparatus generates electrical power using an enzymatic cell that is installed on a person or animal other than the person and generates electrical power using sweat (power generation element that generates electrical power using enzyme reaction), and the control unit converts the power generation amount of the power generation apparatus into secretion composition concentration and amount of exercise of the person or animal, which serves as the second information.

(104-5) The image display apparatus according to 104, in which the power generation apparatus generates electrical power using a power generation element that generates electrical power using radial rays, a radio-wave power generation element that induces electrical power using radio waves (far electromagnetic field), or a near electromagnetic field-used power generation element that induces electrical power using an electromagnetic field in a neighboring region, which includes electromagnetic induction and electrostatic induction, and the control unit converts the power generation amount of the power generation apparatus into intensity of radiation, electromagnetic-wave intensity, and an integrated amount thereof in an installation location of the power generation apparatus (meaning an exposure amount in an installation target), which serves as the second information.

(105) The image display apparatus according to 104, in which the control unit causes the image display unit to display the physical quantity.

(106) The image display apparatus according to 104, in which the power generation apparatus is installed on a human body or another animal and generates electrical power using a physical quantity generated in the human body or animal, and the control unit causes the image display unit to display an image for monitoring the human body or animal, using the physical quantity obtained converted from the first information as the second information.

(107) The image display apparatus according to 104, in which the power generation apparatus is installed in a tool used by a person and generates electrical power using a physical quantity generated in the tool, and the control unit causes the image display unit to display an image for monitoring a motion of the tool or person using the tool, using the physical quantity converted from the first information.

(108) The image display apparatus according to 104, in which the communication unit obtains the first information from one or more power generation apparatuses that generate electrical power using a physical quantity generated in an installation location, and the control unit causes the image display unit to display an image for monitoring an environment in which on which the power generation apparatus is installed, using the physical quantity converted from the first information.

(109) The image display apparatus according to 101, in which the control unit derives, based on at least either the first information or the second information, third information including control information for controlling the image display apparatus itself or an external device.

(110) The image display apparatus according to 101, in which the control unit derives, based on at least either the first information or the second information, third information including action-inducing information for inducing a user to take a predetermined action.

(110-1) The image display apparatus according to 110, in which the power generation apparatus generates electrical power according to an amount of exercise of a person or animal other than the person, and the control unit derives, based on the amount of exercise of the person or animal that is converted from the power generation amount of the power generation apparatus, action-inducing information for inducing an action associated with the amount of exercise of the person or animal as the third information.

(110-2) The image display apparatus according to 110, in which the power generation apparatus generates electrical power according to ultraviolet rays, and the control unit derives, based on ultraviolet intensity converted from the power generation amount of the power generation apparatus, action-inducing information for inducing an action associated with skin care as the third information.

(110-3) The image display apparatus according to 110, in which the power generation apparatus generates electrical power according to a temperature difference, and the control unit derives, based on a temperature difference converted from the power generation amount of the power generation apparatus, action-inducing information for inducing an action associated with an autonomic nervous system or chronic disease as the third information.

(110-4) The image display apparatus according to 110, in which the power generation apparatus generates electrical power according to radio-wave intensity, and the control unit derives, based on radio-wave intensity converted from the power generation amount of the power generation apparatus, action-inducing information for inducing an action associated with a VDT work as the third information.

(111) The image display apparatus according to 104, in which the power generation apparatus generates electrical power that is installed on a human body or another animal and generates electrical power using a physical quantity generated according to a physical exercise of the human body or animal, and the control unit converts the power generation amount of the power generation apparatus into the amount of exercise of the person or animal, which serves as the second information, and causes the image display unit to display the amount of exercise or third information further derived from the amount of exercise.

(112) The image display apparatus according to 101, in which the power generation apparatus is installed in a shoe worn on at least either one of left and right feet of a human body and generates electrical power according to an amount of exercise of the foot, and the control unit converts a power generation amount of the power generation apparatus into the amount of exercise of the foot as the second information.

(113) The image display apparatus according to 104, in which the power generation apparatus generates electrical power to a shoe worn on each of left and right feet of a human body according to an amount of exercise of each of the feet, and the control unit displays, on a left-hand side of a screen, information on the amount of exercise of the left foot that is converted from a power generation amount of the power generation apparatus for the shoe of the left foot and displays, on a left-hand side of the screen, information on the amount of exercise of the right foot that is converted from a power generation amount of the power generation apparatus for the shoe of the right foot.

(114) The image display apparatus according to 104, in which the power generation apparatus generates electrical power to a shoe worn on each of left and right feet of a human body according to an amount of exercise of each of the feet, and the control unit estimates a posture of the human body based on a difference between power generation amounts of the left and right power generation apparatuses or an acceleration of each of the feet that is obtained by converting each of the power generation amounts of the left and right power generation apparatuses as the second information, derives action-inducing information for inducing an action to correct a deviation of the posture of the human body as third information, and causes the image display unit to display the third information.

(115) The image display apparatus according to 114, in which the control unit derives, based on a deviation of the estimated posture of the human body, control information for driving a posture-correcting actuator to correct the deviation of the posture as the third information.

(116) The image display apparatus according to 114, further including an acceleration sensor that measures an acceleration that generates a head or another particular site of the human body, in which the control unit obtains the posture of the human body based on an acceleration of the particular site that is measured by the acceleration sensor and an acceleration of each of the feet that is converted as the second information.

(117) The image display apparatus according to 101, in which the control unit converts a power generation amount of a first power generation apparatus attached to a collar of a companion animal, which serves as the first information, into an acceleration or a metabolic rate of the companion animal, which serves as the second information and converts a power generation amount of a second power generation apparatus attached to a lead with which a person pulls the companion animal, which serves as the first information, into an acceleration or a metabolic rate of the person, which serves as the second information, and causes the image display unit to display the second information.

(118) The image display apparatus according to 101, in which the control unit converts a power generation amount of each of the power generation apparatuses that are installed in a plurality of locations and generate electrical power using electromagnetic waves, radioactivity, or other environmental energy, which serves as the first information, into environmental-energy intensity in each of the locations, which serves as the second information, and causes the image display unit to display the environmental-energy intensity obtained from each of the power generation apparatuses in association with the corresponding location.

(119) The image display apparatus according to 101, in which the power generation apparatus is installed in a foot fin mounted on at least one of left and right feet of a person who is diving and generates electrical power according to the number of kicks of the foot, and the control unit converts a power generation amount of the power generation apparatus into an amount of exercise of the foot, an acceleration, or a water flow, which serves as the second information, and causes the image display unit to display the second information.

(120) The image display apparatus according to 119, further including a water flow sensor that measures a water flow sensor that measures a flow of water flowing around the head or other site of the person, in which the control unit estimates, based on a water flow velocity detected by the water flow sensor and the amount of exercise of the foot that is converted from the power generation amount of the power generation apparatus, a direction of movement of the person under water or strength and direction of the water flow, and causes the image display unit to display it.

(121) The image display apparatus according to 120, in which the control unit calculates the number of kicks of the foot for correcting the direction of movement of the person to an aiming direction and causes the image display unit to display it.

(122) The image display apparatus according to 101, in which the control unit converts a power generation amount of each of the power generation apparatuses that are installed in a plurality of locations within a farm and generate electrical power according to sunlight intensity, which serves as the first information, into an amount of solar radiation in each of the locations, which serves as the second information, derives a growth level, a harvest period, or a harvest order of a farm product in each of the locations from the amount of solar radiation as third information, and causes the image display unit to display the second information or the third information in association with the corresponding location.

(123) The image display apparatus according to 122, further including an imaging unit, in which the control unit compares the growth level of the farm products that is converted from the power generation amount with a real growth level of obtained by analyzing a captured image of the imaging unit to thereby estimate a health state of the farm products.

(124) The image display apparatus according to 101, in which the control unit converts a power generation amount of each of the power generation apparatuses that are installed in a plurality of locations in a manufacturing line within a factory and generate electrical power according to at least one of a temperature difference, mechanical vibrations, pressure fluctuation, or radio waves, which serves as the first information, into temperature, heat flow rate, and heat amount, acceleration, momentum, and pressure, or electromagnetic-wave intensity and electromagnetic-wave intensity integrated amount in each of the locations, which serves as the second information, derives, from the second information, a dangerous point in the manufacturing line as third information, and causes the image display unit to display the second information or the third information in association with the corresponding location.

(125) The image display apparatus according to 101, in which the control unit converts a power generation amount of each of the power generation apparatuses that are installed in a moving object present in a location difficult for the user to see and generate electrical power according to at least either sunlight or mechanical vibrations, which serves as the first information, into sunlight intensity or a vibration amount in each of the locations, which serves as the second information, and causes the image display unit to display the second information in association with the corresponding location.

(126) The image display apparatus according to 101, in which the power generation apparatus is installed on a body of any of a player who is playing a competition, a judge, and a spectator, and generates electrical power using a physical quantity generated in the body, and the control unit derives a state of the player, the competition, or a playing field from a physical quantity obtained by converting a power generation amount of the power generation apparatus.

(127) The image display apparatus according to 101, in which the power generation apparatus is installed in a tool used for a competition and generates electrical power using a physical quantity generated in the tool, and the control unit derives, from the physical quantity obtained by converting the power generation amount of the power generation apparatus, a state of the player or competition.

(128) The image display apparatus according to 101, in which the power generation apparatus is installed in a playing field or a facility within the playing field and generates electrical power using a physical quantity generated in the tool, and the control unit derives a state of the playing field or competition from the physical quantity obtained by converting the power generation amount of the power generation apparatus.

(129) The image display apparatus according to 101, in which the control unit derives, based on at least either the first information or the second information, third information including an image that is added to an image displayed on the image display unit.

(130) An image display method, including the steps of:

communicating with a power generation apparatus and obtaining first information on power generation in the power generation apparatus;

converting the first information into second information based on a principle of the power generation apparatus for inducing electrical power; and displaying the first image or second image.

(131) A storage medium that stores a computer program described in a computer readable format to cause a computer to function as:

an image display unit that displays an image;

a communication unit that communicates with a power generation apparatus; and a control unit that obtains first information on power generation from the power generation apparatus via the communication unit, converts the first information into second information based on a principle of the power generation apparatus for inducing electrical power, and controls the image display unit.

(132) A monitoring system, including:

a power generation apparatus that generates electrical power using a physical quantity generated in a location where the power generation apparatus is installed and transmits first information on power generation; and an image display apparatus that receives the first information, converts the first information into second information including the physical quantity, and displays an image for monitoring the location where the power generation apparatus is installed, using the physical quantity.

DESCRIPTION OF SYMBOLS

100 image display apparatus (transmissive type)
101L, 101R virtual image optical unit 102 support body
103L, 103R microphone
104L, 104R display panel
300 image display apparatus (immersive type)
301L, 301R virtual image optical unit
303L, 303R microphone
304L, 304R display panel
305 pupillary distance adjustment mechanism
501 control unit
501A ROM
501B RAM
502 input operation unit
503 remote-controller reception unit
504 posture/position detection unit
505 communication unit
506 storage unit
507 image processing unit
508 display drive unit
509 display unit
510 virtual image optical unit
511 state detection unit
512 external camera
513 sound processing unit
514 sound input and output unit
515 external display unit
516 environmental sensor
600 monitoring system
611 power generation unit
612 rectifier circuit unit
613 regulator
615 power-supply plug unit
616 arithmetic unit
617 communication unit
618 state detection unit
620 storage element
631 power-supply unit
632 power-supply management unit
633 arithmetic unit
700 monitoring system (Example 1)
701, 702 shoe
710 image display apparatus
711, 712 display unit
713 acceleration sensor
720, 730 power generation apparatus
1600 electromagnetic induction power generation device
1601 shoe
1801 rotor
1802 magnet
1803 stator coil
1900 electret power generation device
2112 substrate
2120 electrode
2121 fixed guide
2122 substrate
2200 piezoelectric power generation device
2201 shoe
2301 piezoelectric element
2302 substrate
2400 inverse-magnetostrictive power generation device
2401 shoe
2501 magnetostrictive element
2502 coil
2503, 2504 fixed end
2600 monitoring system (Example 2)
2601 collar
2602 lead
2610 image display apparatus
2611, 2612 display unit
2613 acceleration sensor
2620, 2630 power generation apparatus
2800 monitoring system (Example 3)
2801 to 2804 wall
2810 image display apparatus
2811, 2812 display unit
2813 environmental sensor
2820 to 2850 power generation apparatus
3200 monitoring system (Example 4)
3210 image display apparatus
3220, 3230 power generation apparatus
3311, 3312 display unit
3313 water flow sensor
3600 monitoring system (Example 4)
3601 aircraft
3602, 3603 power generation apparatus
3604 airflow sensor
3800 monitoring system (Example 5)
3801 to 3804 farm product (cultivation place)
3810 image display apparatus
3811, 3812 display unit
3813 optical sensor
3820 to 3850 power generation apparatus
4100 monitoring system (Example 6)
4110 image display apparatus
4111, 4112 display unit
4120 to 4150 power generation apparatus
4300 monitoring system (Example 7)
4310 image display apparatus
4311, 4312 display unit

The invention claimed is:

1. An image display apparatus, comprising:
circuitry configured to:
control display of an image on a display screen;
communicate with a left power generation apparatus and a right power generation apparatus installed in a shoe worn on a left foot and a shoe worn on a right foot of a human body, respectively,
wherein each of the left power generation apparatus and the right power generation apparatus generates electrical power based on an amount of exercise of each of the left foot and the right foot;
obtain first information on power generation from the left power generation apparatus and the right power generation apparatus;
convert the first information into second information based on a principle of the left power generation apparatus and the right power generation apparatus to induce the electrical power;
determine a posture of the human body based on a difference between a power generation amount of each of the left power generation apparatus and the right power generation apparatus or an acceleration of each of the left foot and the right foot that is obtained based on the conversion of the power generation amount of each of the left power generation apparatus and the right power generation apparatus as the second information;
derive action-inducing information to induce an action to correct a deviation of the posture of the human body as third information; and
control the display screen to display the third information.

2. The image display apparatus according to claim 1, wherein the display screen is mounted on a head or face.

3. The image display apparatus according to claim 1, wherein the circuitry is further configured to control the display screen to combine a virtual image that expresses at least one of the first information or the second information with a real image that shows the left power generation apparatus and the right power generation apparatus and display the combined image.

4. The image display apparatus according to claim 1, wherein
the circuitry is further configured to convert the power generation amount of the left power generation apparatus and the right power generation apparatus included in the first information into the second information including a physical quantity utilized by the let power generation apparatus and the right power generation apparatus to induce the electrical power.

5. The image display apparatus according to claim 1, wherein
the circuitry is further configured to derive, based on at least one of the first information or the second information, the third information including control information to control the display screen or an external device.

6. The image display apparatus according to claim 1, wherein
the circuitry is further configured to derive, based on at least one of the first information or the second information, the third information including the action-inducing information to induce a user to take a particular action.

7. The image display apparatus according to claim 1, wherein
the circuitry is further configured to control the display screen to display, on a left-hand side of the display screen, information on the amount of exercise of the left foot that is converted from the power generation amount of the left power generation apparatus for the shoe of the left foot and display, on a right-hand side of the display screen, information on the amount of exercise of the right foot that is converted from the power generation amount of the right power generation apparatus for the shoe of the right foot.

8. The image display apparatus according to claim 1, wherein
the left power generation apparatus and the right power generation apparatus are installed in a foot fin mounted on each of the left foot or the right foot of a person who dives and generate electrical power based on a number of kicks of each of the left foot and the right foot, and
the circuitry is further configured to:
convert the power generation amount of each of the left power generation apparatus and the right power generation apparatus into a water flow, which serves as the second information, and
control the display screen to display the second information.

9. The image display apparatus according to claim 1, wherein
the left power generation apparatus and the right power generation apparatus are installed on a body of a player who plays a competition, a judge, and a spectator, and generate electrical power based on a physical quantity generated in the body, and
the circuitry is further configured to derive one of a state of the player, the competition, or a playing field from a physical quantity obtained based on the conversion of the power generation amount of each of the left power generation apparatus and the right power generation apparatus.

10. The image display apparatus according to claim 1, wherein
the circuitry is further configured to derive, based on at least one of the first information or the second information, the third information including an image that is added to the image displayed on the display screen.

11. An image display method, comprising:
communicating with a left power generation apparatus and a right power generation apparatus installed in a shoe worn on a left foot and a shoe worn on a right foot of a human body, respectively,
wherein each of the left power generation apparatus and the right power generation apparatus generates electrical power based on an amount of exercise of each of the left foot and the right foot,
obtaining first information on power generation in the left power generation apparatus and the right power generation apparatus;
converting the first information into second information based on a principle of the left power generation apparatus and the right power generation apparatus for inducing the electrical power;
determining a posture of the human body based on a difference between a power generation amount of each of the left power generation apparatus and the right power generation apparatus or an acceleration of each of the left foot and the right foot that is obtained based on the conversion the power generation amount of each of the left power generation apparatus and the right power generation apparatus as the second information;
deriving action-inducing information to induce an action to correct a deviation of the posture of the human body as third information; and
displaying the third information.

12. A non-transitory computer-readable medium having stored thereon computer-readable instructions, which when executed by a computer, cause the computer to execute operations, the operations comprising:
displaying an image;
communicating with a left power generation apparatus and a right power generation apparatus installed in a shoe worn on a left foot and a shoe worn on a right foot of a human body, respectively,
wherein each of the left power generation apparatus and the right power generation apparatus generates electrical power based on an amount of exercise of each of the left foot and the right foot;
obtaining first information on power generation from the left power generation apparatus and the right power generation apparatus;
converting the first information into second information based on a principle of the left power generation apparatus and the right power generation apparatus for inducing the electrical power;
determining a posture of the human body based on a difference between a power generation amount of each of the left power generation apparatus and the right power generation apparatus or an acceleration of each of the left foot and the right foot that is obtained based on the conversion the power generation amount of each of the left power generation apparatus and the right power generation apparatus as the second information;

deriving action-inducing information to induce an action to correct a deviation of the posture of the human body as third information; and displaying the third information.

13. A monitoring system, comprising:

a left power generation apparatus and a right power generation apparatus configured to generate electrical power based on a physical quantity generated in a location where the left power generation apparatus and the right power generation apparatus are installed in a shoe worn on a left foot and a shoe worn on a right foot of a human body, respectively, wherein each of the left power generation apparatus and the right power generation apparatus generates electrical power based on an amount of exercise of each of the left foot and the right foot; and transmit first information on power generation to an image display apparatus; and the image display apparatus configured to:

receive the first information, convert the first information into second information including the physical quantity, determine a posture of the human body based on a difference between a power generation amount of each of the left power generation apparatus and the right power generation apparatus or an acceleration of each of the left foot and the right foot that is obtained based on the conversion the power generation amount of each of the left power generation apparatus and the right power generation apparatus as the second information, derive action-inducing information to induce an action to correct a deviation of the posture of the human body as third information, and display an image to monitor the location where the left power generation apparatus and the right power generation apparatus are installed, based on the physical quantity.

* * * * *